US009804159B2

(12) United States Patent
Messick et al.

(10) Patent No.: US 9,804,159 B2
(45) Date of Patent: Oct. 31, 2017

(54) **IMMUNOREACTIVE ANTIGENS OF *MYCOPLASMA HAEMOFELIS* AND DIAGNOSTIC IMMUNOASSAY**

(75) Inventors: Joanne Belle Messick, Lafayette, IN (US); Andrea Pires Santos, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 755 days.

(21) Appl. No.: 13/879,292

(22) PCT Filed: Oct. 13, 2011

(86) PCT No.: PCT/US2011/056066

§ 371 (c)(1), (2), (4) Date: Apr. 12, 2013

(87) PCT Pub. No.: WO2012/051372

PCT Pub. Date: Apr. 19, 2012

(65) Prior Publication Data

US 2013/0210671 A1 Aug. 15, 2013

Related U.S. Application Data

(60) Provisional application No. 61/393,670, filed on Oct. 15, 2010, provisional application No. 61/408,296, filed on Oct. 29, 2010, provisional application No. 61/408,902, filed on Nov. 1, 2010.

(51) Int. Cl.

| | |
|---|---|
| ***C40B 40/10*** | (2006.01) |
| ***G01N 33/569*** | (2006.01) |
| ***A61K 39/02*** | (2006.01) |
| ***C07K 14/30*** | (2006.01) |
| *A61K 39/00* | (2006.01) |

(52) U.S. Cl.

CPC ... *G01N 33/56933* (2013.01); *A61K 39/0241* (2013.01); *C07K 14/30* (2013.01); *A61K 2039/552* (2013.01); *C40B 40/10* (2013.01)

(58) Field of Classification Search

None

See application file for complete search history.

(56) References Cited

U.S. PATENT DOCUMENTS

| | | | |
|---|---|---|---|
| 5,183,740 | A | 2/1993 | Ligler et al. |
| 5,565,335 | A | 10/1996 | Capon et al. |
| 5,643,570 | A | 7/1997 | Theofan et al. |
| 5,712,170 | A | 1/1998 | Kouvonen et al. |
| 6,277,375 | B1 | 8/2001 | Ward |
| 6,319,691 | B1 | 11/2001 | Pang et al. |

(Continued)

OTHER PUBLICATIONS

PCT International Search Report for PCT US11/56066, dated Apr. 20, 2012.

(Continued)

*Primary Examiner* — Christian Boesen

(74) *Attorney, Agent, or Firm* — Barnes & Thornburg LLP

(57) ABSTRACT

Compositions for use in diagnostic screens for *Mycoplasma haemofelis* are provided. In one embodiment an immunogenic peptide selected from SEQ ID NO: 1 to SEQ ID NO: 60, or a fragment thereof, is immobilized on a solid support and is used to detect the presence of *Mycoplasma haemofelis* antibodies in a patient bodily fluid. In accordance with one embodiment a method for detecting a *Mycoplasma haemofelis* infection in a feline species, is provided.

21 Claims, 1 Drawing Sheet

(56) References Cited

U.S. PATENT DOCUMENTS

2003/0233675 A1 12/2003 Cao et al.
2007/0237794 A1 10/2007 Goto et al.

OTHER PUBLICATIONS

Darmon et al., 2006, "A Disulfide Bond-Containing Alkaline Phospatase Triggers a BdbC-Dependent Secretion Stress Response in Bacillus subtilis," Applied and Enrionmental Microbiology, 72(11): pp. 6876-6885.

Kerrien et al., 2007, "IntAct-open source resource for molecular interaction data," Nucleic Acids Research, 35: pp. D561-D565.

Forlani et al, 2006, Assessing the Nitrogen and Carbon Nucleophilicities of 2-Aminothiazoles through Coupling with Superelectrophilic 4,6-Dinitrogenzofuroxan, J Org. Chem., 71:5527-5537.

Sellman et al., 2005, "Identification of Immunogenic and Serum Binding Proteins of *Staphylococcus epidermidis*," Ifenction and Immunity, 73(10): pp. 6591-6600.

Jacobsen et al, 2005, "Enzymes Involved in Anaerobic Respiration Appear to play a role in *Actinobacillus pleuropneumoniae* Virulence," Infection and Immunity, 73(1): pp. 226-234.

Kusterbeck et al., 1990, "A Continuous Flow Immunoassay for Rapid and Sensitive Detection of Small Molecules," 135: pp. 191-197.

Kusterbeck et al., 1990, "Antibody-Based Biosensor for Continuous Monitoring", in Biosensor Technology, R. P. Buck et al., eds., Marcel Dekker, N.Y. pp. 345-350.

Ligler et al., 1992, "Drug Detection Using the Flow Immunosensor", in Biosensor Design and Application, J. Findley et al., eds., American Chemical Society Press, pp. 73-80.

Ogert et al., 1992, "Detection of Cocaine Using the Flow Immunosensor", Analytical Letters, vol. 25, pp. 1999-2019.

Kohler et al., 1975, Practical Immunology, Nature, 256: pp. 256:495.

Altschul et al, 1990, "Basic Alignment Search Tool," J. Mol. Biol., 215: pp. 403-410.

Altschul, 1997, "Gapped BLAST and PSI-BLAST: A new generation of protein database search programs" Nucleic Acids Res, 25(17): pp. 3389-3402.

Cserzo et al., 1997, "Prediction of transmembrane α-helices in prokaryotic membrane proteins: the dense alignment surface method," Protein Engineering, 10: pp. 673-676.

Alleman et al., Western Immunoblot Analysis of the Antigens of Haemobartonells felis with Sera from Experimentally Infected Cats, J. Clin. Microbiol., 1999, vol. 37, pp. 1474-1479.

Barker et al., "Detection of Humoral Response using a Recombinant heat Shock Protein 70, DnaK, of Mycoplasma haemofelis in Experimentally and Naturally Hemoplasma-Infected Cats," Clinical and Vaccine Immunology, vol. 17, No. 12, Oct. 6, 2010, pp. 1923-1932.

Berent et al., "Physical Map and Genome Sequencing Survey of Mycoplasma haemofelis (Haemobartonella felis)," Infect. Immun. 2003, vol. 71, pp. 3657-3662.

GenBank BH793052, MH0128 Sub-clone library of Mycoplasma haemofelis BAC clones Mycoplasma haemofelis genomic, genomic survey sequence, Mar. 31, 2003 [Retrieved from the internet Apr. 12, 2012 <http.//www.ncbi.nlm.nih.gov/nucgss/BH793052.1>.

Messick et al., "Identification, Bioinformatics Analyses, and expression of Immunoreactive Antigens of Mycoplasma haemofelis," clinical and Vaccine Immunology, vol. 18, No. 8, Jun. 8, 2011, pp. 1275-1281.

Tasker et al., "Use of Real-Time PCR to Detect and Quantify Mycoplasma haemofelis and "Candidatus Mycoplasma haemominutum" DNA," J. of Clin. Microbiology, 2003, vol. 41, pp. 439-441.

IMMUNOREACTIVE ANTIGENS OF *MYCOPLASMA HAEMOFELIS* AND DIAGNOSTIC IMMUNOASSAY

CROSS REFERENCE TO RELATED APPLICATIONS

This application is a national stage entry under 35 USC §371(b) of International Application No. PCT/US2011/056066, filed Oct. 13, 2011, which claims priority under 35 USC §119(e) to U.S. Provisional Application Nos. 61/393,670, 61/408,296 and 61/408,902 filed on Oct. 15, 2010, Oct. 29, 2010, and Nov. 1, 2010, respectively. The disclosures of which are hereby expressly incorporated by reference in their entirety.

BACKGROUND

*Mycoplasma haemofelis* (*Haemobartonella felis*) is a hemotropic pathogen that causes acute and chronic diseases in cats. Distributed worldwide, the parasite has a significant impact on the health and well being of this species. The disease in cats was first reported in the United States in 1953. Acute infection with *M. haemofelis* is associated with a massive parasitemia of red blood cells that leads to a severe and sometimes fatal hemolytic anemia. The parasite is also notorious for its ability to evade the immune response of the host and successfully establish chronic infection. Furthermore, despite an intense immune response and/or antibiotic treatment, cats often remain asymptomatic carriers following infection. *M. haemofelis* is recognized as a secondary pathogen in conjunction with retroviruses, including Feline Leukemia Virus (FeL V) and Feline Immunodeficiency Virus (FIV), and might promote neoplastic transformation of hematopoietic cells in these cats. Recent studies based on polymerase chain reaction testing (PCR) have shown that about 25% of all cats that are anemic and/or acutely ill have a *M. haemofelis* infection.

To provide a commercially viable immunoassay for the diagnosis of *M. haemofelis*, a convenient and renewable source of antigen is needed for developing an immunoassay, as well as one that can be standardized. Since *M. haemofelis* cannot be grown in culture, the only source of antigen for an immunoassay is whole parasites harvested from an infected cat. This is not a convenient source and preparations of whole cell or membrane antigens are difficult to standardize.

The identification of immunogenic proteins of pathogens is important for the development of serologic diagnostic assays. Two-dimensional polyacrylamide gel electrophoresis (SDS¬P AGE), followed by mass spectrometry and microsequencing is a commonly used method for identifying candidate proteins (Meens et al. 20006; Huntley et al., 2007, Delvecchio et al., 2006, Sellman et al., 2005; Jacobsen et al. 2005). However, low and differentially expressed antigens cannot be identified using this technique. Several groups have used Phage lambda vectors to construct genomic expression libraries of mycoplasmal pathogens. To overcome the uncommon usage of the opal stop codon (UGA) by some *Mycoplasma* spp. to encode tryptophan, expression libraries constructed in *E. coli* harboring an inducible opal suppressor may be used to improve the results achieved. Following induction, clones that are immunodominant can be identified by screening the library with convalescent-phase or immune sera. Recombinant antigens are convenient, renewable, and once purified, can be standardized for use in an immunoassay.

SUMMARY

Compositions for use in diagnostic screens for *M. haemofelis* are provided. In one embodiment a composition comprising two or more isolated immunogenic peptides is provided wherein the peptides comprise an amino acid sequence selected from SEQ ID NO: 1 to SEQ ID NO: 60, or a contiguous 8 amino acid fragment of an amino acid sequence selected from SEQ ID NO: 1 to SEQ ID NO: 60. In a further embodiment the isolated peptides are recombinantly produced fusion peptides, wherein *M. haemofelis* sequences selected from SEQ ID NO: 1 to SEQ ID NO: 60 further comprise an amino acid sequence at the carboxy or amino terminus that is not native to the peptide sequence. In one embodiment an immunogenic peptide selected from SEQ ID NO: 1 to SEQ ID NO: 60, or a fragment thereof, is immobilized on a solid support. Typically the peptide is immobilized by a covalent bond linking the peptide to the solid support either directly to the surface of the solid support or through a linking moiety. In one embodiment the solid support comprises a bead or chip comprising an array of peptides.

In accordance with one embodiment a method for detecting a *Mycoplasma haemofelis* infection in a warm blooded vertebrate is provided. In one embodiment the warm blooded vertebrate is a feline species, including for example a domesticated cat. In one embodiment the method comprises analyzing a bodily fluid isolated from said vertebrate for the presence of antibodies that specifically bind to a peptide comprising a sequence selected from SEQ ID NO: 1 to SEQ ID NO: 60, or a contiguous 8 amino acid fragment of an amino acid sequence selected from SEQ ID NO: 1 to SEQ ID NO: 60. In one embodiment the biological sample recovered from the warm blooded vertebrate species is screened for anti-*Mycoplasma haemofelis* antibodies through the use of an immunoassay. In one embodiment the immunoassay is selected from the group consisting of enzyme linked immunosorbent assays (ELISAs), radioimmunoassays (RIAs), and Western blots.

BRIEF DESCRIPTION OF THE DRAWINGS

FIG. 1A is a photo of an SDS-PAGE gel of the fusion proteins recovered before ($T_0$) and after ($T_F$) induction of expression. FIG. 1B is a photo of Western blot results of the fusion proteins against convalescent serum from a experimentally infected cat. M=molecular weight marker (PRECISION PLUS PROTEIN KALEIDOSCOPE, BioRad).

DETAILED DESCRIPTION

Definitions

Figure 1A:
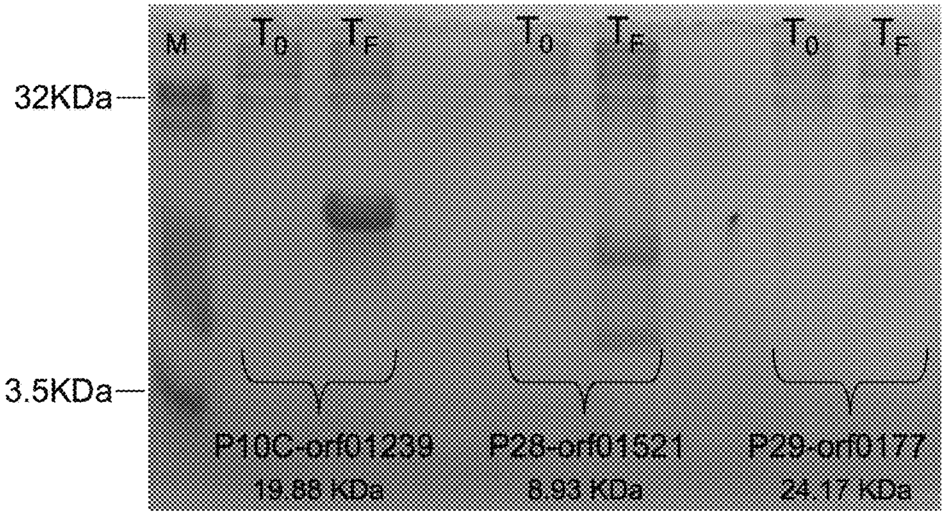
FIGS. 1A and 1B are photographs showing the expression and reactivity of proteins P 10C-orf01239 (SEQ ID NO: 20), P28-orf01521 (SEQ ID NO: 52), and P29-orf0177 (SEQ ID NO: 57) with serum from a *Mycoplasma haemofelis* infected cat.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "patient" without further designation is intended to encompass any warm blooded vertebrate domesticated animal (including for example, but not limited to livestock, horses, cats, dogs and other pets) and humans.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —$CH_2$-carbamate linkage (—$CH_2$OC(O)NR—), a phosphonate linkage, a —$CH_2$-sulfonamide (—$CH_2$—$S(O)_2$NR—) linkage, a urea (—NHC(O)NH—) linkage, a—$CH_2$-secondary amine linkage, or with an alkylated peptidyl linkage (—C(O)NR—) wherein R is $C_1$-$C_4$ alkyl;

2. peptides wherein the N-terminus is derivatized to a —$NRR_1$ group, to a —NRC(O)R group, to a —NRC(O)OR group, to a —$NRS(O)_2R$ group, to a —NHC(O)NHR group where R and $R_1$ are hydrogen or $C_1$-$C_4$ alkyl with the proviso that R and $R_1$ are not both hydrogen;

3. peptides wherein the C terminus is derivatized to —$C(O)R_2$ where $R_2$ is selected from the group consisting of $C_1$-$C_4$ alkoxy, and —$NR_3R_4$ where $R_3$ and $R_4$ are independently selected from the group consisting of hydrogen and $C_1$-$C_4$ alkyl.

As used herein the term "solid support" relates to a solvent insoluble substrate that is capable of forming linkages (preferably covalent bonds) with soluble molecules. Typically the support is composed of synthetic materials, such as, without limitation, an acrylamide derivative, glass, plastic, agarose, cellulose, nylon, silica, or magnetized particles. The support can be in particulate form or a monolythic strip or sheet. The surface of such supports may be solid or porous and of any convenient shape.

An "array" refers a device consisting of a substrate, typically a solid support having a surface adapted to receive and immobilize a plurality of different protein, peptide, and/or nucleic acid species (i.e., capture or detection reagents) that can used to determine the presence and/or amount of other molecules (i.e., analytes) in biological samples such as blood. Examples of arrays include functionalized solid surfaces (biochips) with peptides linked thereto as well as peptides linked to a solid matrix through electrostatic and/or affinity interactions (e.g., Western Blot).

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified polypeptide" is used herein to describe a polypeptide which has been separated from other compounds including, but not limited to nucleic acid molecules, lipids and carbohydrates. A "highly purified" compound as used herein refers to a compound that is greater than 95% pure.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "antibody" refers to a polyclonal or monoclonal antibody or a binding fragment thereof such as Fab, $F(ab')_2$ and Fv fragments.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have nucleic acid/amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein, the term "primer" refers to an oligonucleotide, whether occurring naturally as in a purified restriction digest product, or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids. High stringency conditions (low salt, high temperature) are well known in the art. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

Embodiments

Prior to applicant's invention, the preparation of *Mycoplasma haemofelis* antigen was contingent upon infection of a cat since this parasite cannot be grown in culture. The process of isolating the organisms from whole blood is cumbersome and involves lengthy detachment and selective centrifugations and filtration procedures, however this was previously the only method for obtaining potential immunoreactive antigens of *M. haemofelis*. The isolation of immunoreactive antigens of *M. haemofelis* is desirable to provide an antigen source for development of 1) serologic assays and 2) vaccine production. As disclosed herein applicants have prepared a *M. haemofelis* expression library to enhance the production and characterization of *Mycoplasma haemofelis* proteins to allow identification of suitable antigenic peptides.

Applicants have successfully identified immunodominant antigens of *M. haemofelis*, including for example those listed in Table 1 of Example 1. Such immunogenic antigens can be used in vaccine formulations as well as in assays designed to identify animals infected with *M. haemofelis* that previously would not be detected. For example, the polypeptide antigens disclosed herein can provide the basis of a diagnostic assay for detecting antibodies present in infected animals, thus identifying animals exposed to *Mycoplasma haemofelis* antigen. Such a method allows for a sensitive, rapid, in-house, laboratory diagnosis of *M. haemofelis* infection of warm blooded vertebrates, including feline species such as domesticated cats. In one embodiment, the assay is conducted using a biological sample (e.g., serum, plasma, or whole blood) from a warm blooded vertebrate. In a further embodiment methods are provided for detecting the presence and/or degree of *M. haemofelis* in biological or environmental samples through the use of the isolated immunogenic *M. haemofelis* peptides disclosed herein to detect the presence of anti-*M. haemofelis* antibodies in the sample.

In accordance with one embodiment an isolated or purified *M. haemofelis* peptide is provided comprising an amino acid sequence selected from the group consisting of SEQ ID NO: 1 through SEQ ID NO: 60. In another embodiment the peptide comprises a sequence selected from the group consisting of P3-orf1165 (SEQ ID NO: 1), P6D-orf00908 (SEQ ID NO: 3), P7-orf0262 (SEQ ID NO: 8), P7-orf0263 (SEQ ID NO: 9), P10B-orf01747 (SEQ ID NO: 15), P10B-orf1749 (SEQ ID NO: 17, P10C-orf01238 (SEQ ID NO: 19), P10C-orf01239 (SEQ ID NO: 20), P10E-orf00279 (SEQ ID NO: 21), P15-orf00945 (SEQ ID NO: 27, P15-orf00946 (SEQ ID NO: 28), P15-orf00947 (SEQ ID NO: 29), P18-orf00128 (SEQ ID NO: 37), P21A-orf00675 (SEQ ID NO: 39), P21B-orf01544 (SEQ ID NO: 40), P24-orf01679 (SEQ ID NO: 45), P28-orf01521 (SEQ ID NO: 52) and P29-orf0177 SEQ ID NO: 57). Each of these peptides have been identified as being immunogenic and thus useful as a diagnostic test antigens or as the antigenic component of a vaccine formulation. In one embodiment an isolated or purified *M. haemofelis* peptide is provided comprising an amino acid sequence selected from the group consisting of SEQ ID NO: 3, SEQ ID NO: 19, SEQ ID NO: 20 and SEQ ID NO: 21. In one embodiment an isolated or purified *M. haemofelis* peptide is provided comprising a fragment of P6D-orf00908 (position 1-65; SEQ ID NO: 122), P10C-orf01238 (position 85-255; SEQ ID NO: 123), P10C-orf01239 (position 538-687; SEQ ID NO: 124), and P10E-orf00279 (position 1-159; SEQ ID NO: 125). In one embodiment the peptide comprises the sequence of SEQ ID NO: 20 or SEQ ID NO: 124.

Also encompassed by the present invention are antigenic fragments of an amino acid sequence selected from SEQ ID NO: 1 through SEQ ID NO: 60. In one embodiment the peptide fragment comprises a contiguous amino acid sequence of at least 6, 7, 8, 9, 10, 11, 12, 13, 14, 15, 16, 17, 18, 19, 20, 21 22, 23, 24, 25, 26, 27, 28, 29, or 30 amino acids that is identical in sequence to a contiguous amino acid sequence contained within a sequence selected from SEQ ID NO: 1 through SEQ ID NO: 60. In one embodiment the fragment comprises at least an 8 contiguous amino acid sequence identical to a sequence contained within SEQ ID NO: 1, SEQ ID NO: 3, SEQ ID NO: 8, SEQ ID NO: 9, SEQ ID NO: 15, SEQ ID NO: 17, SEQ ID NO: 19, SEQ ID NO: 20, SEQ ID NO: 21, SEQ ID NO: 27, SEQ ID NO: 28, SEQ ID NO: 29, SEQ ID NO: 37, SEQ ID NO: 39, SEQ ID NO: 40, SEQ ID NO: 45, SEQ ID NO: 52 or SEQ ID NO: 57. In one embodiment an antigenic peptide is provided that comprises at least an eight amino acid sequence that is identical to a contiguous eight amino acid sequence contained in a sequences selected from SEQ ID NO: 1 through SEQ ID NO: 60. In one embodiment the fragment comprises at least an 8 contiguous amino acid sequence identical to a sequence contained within SEQ ID NO: 3, SEQ ID NO: 19, SEQ ID NO: 20 or SEQ ID NO: 21.

In one embodiment a peptide is provided that comprises a contiguous span of at least 6, 7, 8, 9, 10, 11, 12, 13, 14, 15, 16, 17, 18, 19, 20, 21 22, 23, 24, 25, 26, 27, 28, 29, 30 amino acids that shares at least 80% sequence identity (e.g., 80%, 85%, 90%, 95% or 99%) with a contiguous sequence of the same length contained within a sequence selected from the group consisting of SEQ ID NO: 1 through SEQ ID NO: 60. In one embodiment a peptide is provided that comprises a contiguous span of at least 8, 9, 10, 11, 12, 13, 14, 15, 16, 17, 18, 19, 20, 21 22, 23, 24, 25, 26, 27, 28, 29, 30 amino acids that shares at least 95% sequence identity with a contiguous sequence of the same length contained within a sequence selected from the group consisting of SEQ ID NO: 1 through SEQ ID NO: 60. In one embodiment a peptide is provided that comprises a contiguous span of at least 8, 9, 10, 11, 12, 13, 14, 15, 16, 17, 18, 19, 20, 21 22, 23, 24, 25, 26, 27, 28, 29, 30 amino acids that shares at least 95% sequence identity with a contiguous sequence of the same length contained within a sequence selected from the group consisting of SEQ ID NO: 3, SEQ ID NO: 19, SEQ ID NO: 20, SEQ ID NO: 21, SEQ ID NO: 122, SEQ ID NO: 123, SEQ ID NO: 124, and SEQ ID NO: 125.

In one embodiment a peptide is provided that comprises a contiguous span of at least 6, 7, 8, 9, 10, 11, 12, 13, 14, 15, 16, 17, 18, 19, 20, 21 22, 23, 24, 25, 26, 27, 28, 29, 30 amino acids that differs from a sequence selected from the group consisting of SEQ ID NO: 1 through SEQ ID NO: 60 by 1, 2 or 3 amino acids. In one embodiment a peptide is provided that comprises a contiguous span of at least 8 amino acids that differs from a contiguous 8 amino acid sequence selected from the group consisting of SEQ ID NO: 1 through SEQ ID NO: 60 by 1 amino acid. In one embodiment the 1, 2 or 3 different amino acids represent conservative amino acid substitutions.

Immunogenic fragments of the peptides of SEQ ID NOs: 1-60 can also be described in terms of the N-terminal and C-terminal positions of the original protein. For example, the N terminus and C terminus of an 8 amino acid fragment of a sequence selected from SEQ ID NO: 1 through 60 can be assigned numbers relative to the position of the amino acids in the corresponding parent protein. More specifically, an 8 amino acid sequence fragment of SEQ ID NO: 1 that has the first three amino acids deleted and comprises the next eight amino acids can be designated fragment N4-C11 of SEQ ID NO: 1. Accordingly, fragments of any of SEQ ID NO: 1 through SEQ ID NO: 60 having a fragment length starting from 8 contiguous amino acids up to 1 amino acid less than the full length polypeptide are included in the present invention. Thus, an 8 consecutive amino acid fragment could correspond to amino acid fragments selected from the group consisting of 1-8, 2-9, 3-10, 4-11, 5-12, 6-13, 7-14, 8-15, 9-16, 10-17, 11-18, 12-18, 13-20, . . . to (X minus 7 to X), wherein X is an integer representing the total number of amino acids of the parent peptide from which the fragment is derived.

The present disclosure also encompasses conjugates of the antigenic *M. haemofelis* peptides disclosed herein, wherein the *M. haemofelis* peptides are linked, optionally via covalent bonding and optionally via a linker, to a conjugate moiety. Exemplary conjugate moieties that can be linked to any of the *M. haemofelis* peptides peptides described herein include but are not limited to a heterologous peptide or polypeptide (including for example, a plasma protein), a targeting agent, an adjuvant, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. Linkage can be accomplished by covalent chemical bonds, physical forces such electrostatic, hydrogen, ionic, van der Waals, or hydrophobic or hydrophilic interactions. The peptide can be linked to conjugate moieties via direct covalent linkage by reacting targeted amino acid residues of the peptide with an organic derivatizing agent that is capable of reacting with selected side chains or the N- or C-terminal residues of these targeted amino acids.

In accordance with one embodiment an antigenic *M. haemofelis* fusion peptide is provided wherein a peptide sequence selected from SEQ ID NO: 1 through SEQ ID NO: 60 is further modified to comprise a non-native amino acid sequence linked to the carboxy or amino terminus of the peptide selected from SEQ ID NO: 1 through SEQ ID NO: 60. In one embodiment the anitgenic *M. haemofelis* fusion peptide comprises a peptide selected from the group consisting of SEQ ID NO: 19, SEQ ID NO: 20, SEQ ID NO: 21, SEQ ID NO: 122, SEQ ID NO: 123, SEQ ID NO: 124, and SEQ ID NO: 125. In one embodiment the sequence added to the amino or carboxy terminus is a sequence not native to *M. haemofelis*.

In accordance with one embodiment the antigenic *M. haemofelis* peptides disclosed herein are combined with a pharmaceutically acceptable carrier and are administered to a warm blooded vertebrate to induce an immune response, optionally including the production of antibodies against the immunogenic peptides. In one embodiment the composition further comprises an adjuvant. In accordance with one embodiment a composition is provided comprising an antigenic *M. haemofelis* peptide or conjugate thereof as disclosed herein.

In one embodiment one or more of the *M. haemofelis* immunogenic peptides disclosed herein are linked to a solid support. The linkage may comprise a covalent, ionic, or hydrogen bond or other interaction that binds the peptide to the solid support either directly or through an intermediate linking moiety. In one embodiment the peptides are covalently bound to the solid support, either directly or via a linker. The solid support may be comprised of any suitable material (e.g., magnetic or non-magnetic metal, silicon, glass, cellulose, plastics, polyethylene, polypropylene, polyester, nitrocellulose, nylon, and polysulfone plastic) that will allow for the binding of a peptide of SEQ ID NO: 1-60 to the support material either by a direct or indirect linkage. The solid support may be configured into a number of shapes including, for example, a test tube, microtiter well, sheet, bead (e.g., magnetic beads, non-magnetic beads, agarose beads) microparticle, chip, and other configurations known to those of ordinary skill in the art. In one embodiment the solid support represents an array of electrophoretically separated proteins linked to a sheet of nitrocellulose or synthetic material (i.e., a Western blot). In another embodiment the solid support is a bead comprising one or more sequences selected from the group consisting of SEQ ID NO: 1 through SEQ ID NO: 60 linked to its surface. In a further embodiment the solid support is a strip or chip comprising an array of one or more of the peptides of SEQ ID NO: 1 through SEQ ID NO: 60 linked to its surface. In one embodiment an isolated peptide complex is provided comprising an amino acid sequence selected from the group consisting of SEQ ID NO: 1 through SEQ ID NO: 60, or a contiguous 8 amino acid fragment of an amino acid sequence selected from the group consisting of SEQ ID NO: 1 through SEQ ID NO: 60, and a solid support, wherein said peptide is immobilized on said solid support. In one embodiment the immobilized peptide comprises the sequence of P3-orf1165 (SEQ ID NO: 1), P6D-orf00908 (SEQ ID NO: 3), P7-orf0262 (SEQ ID NO: 8), P7-orf0263 (SEQ ID NO: 9), P10B-orf01747 (SEQ ID NO: 15), P10B-orf1749 (SEQ ID NO: 17), P10C-orf01238 (SEQ ID NO: 19), P10C-orf01239 (SEQ ID NO: 20), P10E-orf00279 (SEQ ID NO: 21), P15-orf00945 (SEQ ID NO: 27), P15-orf00946 (SEQ ID NO: 28), P15-orf00947 (SEQ ID NO: 29), P18-orf00128 (SEQ ID NO: 37), P21A-orf00675 (SEQ ID NO: 39), P21B-orf01544 (SEQ ID NO: 40), P24-orf01679 (SEQ ID NO: 45), P28-orf01521 (SEQ ID NO: 52) and P29-orf0177 (SEQ ID NO: 57), or a contiguous 8 amino acid sequence fragment thereof. In another embodiment the immobilized peptide comprises the sequence of SEQ ID NO: 3, SEQ ID NO: 19, SEQ ID NO: 20, SEQ ID NO: 21, or a contiguous 8 amino acid sequence fragment of said sequences. In one embodiment the immobilized peptide comprises a peptide selected from the group consisting of SEQ ID NO: 122, SEQ ID NO: 123, SEQ ID NO: 124, and SEQ ID NO: 125). In one embodiment the immobilized peptide comprises the sequence of SEQ ID NO: 20 or SEQ ID NO: 124. In one embodiment the arrays of the present disclosure comprise at least two peptides comprising a sequence selected from the group consisting of SEQ ID NO: 1 through 60, or an continuous 8 amino acid fragment thereof, linked to its surface.

In accordance with one embodiment a method of detecting anti-*M. haemofelis* antibodies in a sample is provided wherein the method comprises the step of contacting the sample with a peptide comprising a sequence selected from the group consisting of SEQ ID NO: 1 through 60, or an continuous 8 amino acid fragment thereof under conditions that allow for the formation of an antibody-antigen complex. These methods can further comprise the step of detecting the formation of said antibody-antigen complex. In one embodiment a method of detecting a *Mycoplasma haemofelis* infection, and/or determining the degree of infection, in a warm blooded vertebrate is provided. In one embodiment the warm blooded vertebrate is a feline species, including for example, domesticated cats. The method comprises analyzing a bodily fluid from said vertebrate for the presence of antibodies that specifically bind to an amino acid sequence selected from SEQ ID NO: 1 through SEQ ID NO: 60, or a contiguous 8 amino acid fragment of SEQ ID NO: 1 through SEQ ID NO: 60. In one embodiment the method comprises analyzing a bodily fluid from said vertebrate for the presence of antibodies that specifically bind to an amino acid sequence selected from the group consisting of SEQ ID NO: 3, SEQ ID NO: 19, SEQ ID NO: 20, SEQ ID NO: 21, SEQ ID NO: 122, SEQ ID NO: 123, SEQ ID NO: 124, and SEQ ID NO: 125). In one embodiment the bodily fluid represents a biological sample recovered from the patient to be investigated for an *M. haemofelis* infection and may include any bodily fluid where anti-*M. haemofelis* antibodies would be expected to be present. In one embodiment the bodily fluid is blood or a blood derivative such as plasma or serum. The binding of the anti-*M. haemofelis* antibodies with the immunogenic peptides disclosed herein can be detected using any procedure known to those skilled in the art including for example the use of an immunoassay. In one embodiment the immunoassay is selected from the group consisting of enzyme linked immunosorbent assays (ELISAs), radioimmunoassays (RIAs), lateral flow assays, immunochromatographic strip assays, automated flow assays, Western blots, immunoprecipitation assays, reversible flow chromatographic binding assays, agglutination assays, and biosensors. In one embodiment the assay used is either an enzyme linked immunosorbent assay or Western blot analysis.

In one embodiment the detection of the anti-*M. haemofelis* antibodies is conducted using a panel or an array of peptides comprising one or more amino acid sequences selected from SEQ ID NO: 1 through SEQ ID NO: 60, or a contiguous 8 amino acid fragment of an amino acid sequence selected from SEQ ID NO: 1 through SEQ ID NO: 60. In one embodiment the panel or array of peptides comprising one or more amino acid sequences selected from SEQ ID NO: 3, SEQ ID NO: 19, SEQ ID NO: 20, SEQ ID NO: 21, or a contiguous 8 amino acid sequence fragment of said sequences. In one embodiment the array of peptides comprises one or more amino acid sequences selected from the group consisting of SEQ ID NO: 122, SEQ ID NO: 123, SEQ ID NO: 124, and SEQ ID NO: 125. In one embodiment the solid support comprises an array of the same peptide, including any peptide selected from the group consisting of SEQ ID NO: 1 through SEQ ID NO: 60, including for example the peptide of P10C-orf01239 (SEQ ID NO: 20), or a fragment thereof such as SEQ ID NO: 124. Alternatively, the array of peptides may comprises at least two different peptides comprising an amino acid sequence selected from SEQ ID NO: 1 through SEQ ID NO: 60, or a contiguous 8 amino acid sequence fragment of said sequences, or selected from SEQ ID NO: 3, SEQ ID NO: 19, SEQ ID NO: 20, SEQ ID NO: 21 or a contiguous 8 amino acid fragment of said sequences. In one embodiment the immobilized peptides on the array comprise sequences independently selected from the group consisting of P3-orf1165 (SEQ ID NO: 1), P6D-orf00908 (SEQ ID NO: 3), P7-orf0262 (SEQ ID NO: 8), P7-orf0263 (SEQ ID NO: 9), P10B-orf01747 (SEQ ID NO: 15), P10B-orf1749 (SEQ ID NO: 17, P10C-orf01238 (SEQ ID NO: 19, P10C-orf01239 (SEQ ID NO: 20), P10E-orf00279 (SEQ ID NO: 21), P15-orf00945 (SEQ ID NO: 27, P15-orf00946 (SEQ ID NO: 28), P15-orf00947 (SEQ ID NO: 29), P18-orf00128 (SEQ ID NO: 37), P21A-orf00675 (SEQ ID NO: 39), P21B-orf01544 (SEQ ID NO: 40), P24-orf01679 (SEQ ID NO: 45), P28-orf01521 (SEQ ID NO: 52) and P29-orf0177 SEQ ID NO: 57), or a contiguous 8 amino acid sequence fragment of those sequences. In another embodiment the immobilized peptides comprise sequences selected from the group consisting of SEQ ID NO: 3, SEQ ID NO: 19, SEQ ID NO: 20, SEQ ID NO: 21, or a contiguous 8 amino acid sequence fragment of those sequences. In one embodiment the immobilized peptides comprise one or more amino acid sequences selected from the group consisting of SEQ ID NO: 122, SEQ ID NO: 123, SEQ ID NO: 124, and SEQ ID NO: 125. In one embodiment, one of the peptides present on the array is the peptide of SEQ ID NO: 20.

In one embodiment a method of detecting a *Mycoplasma haemofelis* infection in a feline species is provided wherein the method comprises obtaining a bodily fluid from a feline species, and analyzing the bodily fluid for the presence of antibodies that specifically bind to a peptide comprising an amino acid sequence selected from SEQ ID NO: 1 through SEQ ID NO 60, or a contiguous 8 amino acid fragment of an amino acid sequence selected from SEQ ID NO: 1 through SEQ ID NO 60.

In accordance with one embodiment a method of detecting a *Mycoplasma haemofelis* infection in a feline species is provided. The method comprises obtaining a bodily fluid from a feline species, contacting the bodily fluid with a peptide selected from the group consisting of SEQ ID NO: 1, SEQ ID NO: 3, SEQ ID NO: 8, SEQ ID NO: 9, SEQ ID NO: 15, SEQ ID NO: 17, SEQ ID NO: 19, SEQ ID NO: 20, SEQ ID NO: 21, SEQ ID NO: 27, SEQ ID NO: 28, SEQ ID NO: 29, SEQ ID NO: 37, SEQ ID NO: 39, SEQ ID NO: 40, SEQ ID NO: 45, SEQ ID NO: 52 and SEQ ID NO: 57, and detecting antibody peptide complexes formed between an antibody from said bodily fluid that has specifically bound to said peptide, wherein detection of said complexes identifies a feline infected with *Mycoplasma haemofelis*. In one embodiment the *Mycoplasma haemofelis* antigenic peptides are immobilized in a matrix or bound to a solid support and the antigenic peptides are contacted with the bodily fluid under conditions that allow specific binding of any antibodies present in the bodily fluid to the peptides. The bodily fluid is incubated with the immobilized/bound peptides for a time sufficient to allow specific binding and then the immobilized/bound peptides are washed to remove any non-specific bound material. After the washing step the immobilized/bound peptides are analyzed using standard techniques to detect any antibodies that have bound to the immobilized/bound peptides. The detection of such antibody/peptide complexes indicates the subject the bodily fluid was recovered from is infected with *Mycoplasma haemofelis.*

In one embodiment the solid support comprises two or more different peptides and in one embodiment the peptides bound to the solid support are selected from the group consisting of SEQ ID NO: 3, SEQ ID NO: 19, SEQ ID NO: 20 and SEQ ID NO: 21.

Detection of the antibody-peptide complexes in accordance with the present disclosure can be conducted using one of four types of assays: direct binding assays, sandwich assays, competition assays, and displacement assays. In a direct binding assay, either the antibody or the peptide is labeled, and there is a means of measuring the number of complexes formed. In a sandwich assay, the formation of a complex of at least three components (e.g., antibody-antigen-antibody) is measured. In a competition assay, labeled antigen and unlabelled antigen compete for binding to the antibody, and either the bound or the free component is measured. In a displacement assay, labeled antibody is pre-bound to the antigen, and a change in signal is measured as the unlabelled antibody displaces the bound, labeled antibody from the antigen.

Non-limiting examples of immunoassays that can be used for the detection of anti-*M. haemofelis* antibodies include, enzyme linked immunosorbent assays (ELISAs), radioimmunoassays (RIAs), lateral flow assays, immunochromatographic strip assays, automated flow assays, Western blots, immunoprecipitation assays, reversible flow chromatographic binding assays, agglutination assays, and biosensors. In one embodiment the assay used is an ELISA sandwich assay or a Western blot. Additional aspects of the present disclosure encompass the use of an array of polypeptides when conducting the aforementioned methods of detection (the array can comprise polypeptides of the same or different sequence as well as negative and positive control amino acid sequences).

Immunoassays can involve "sandwich" approaches in which the analyte to be detected (e.g., a serum antibody reactive with a peptide of SEQ ID NO: 1 through SEQ ID NO 60) is bound by two other entities, for example, by a capture reagent (e.g., a peptide of SEQ ID NO: 1 through SEQ ID NO 60) immobilized on a solid support and specific for the anti-*M. haemofelis* antibodies present in a sample, and a labeled detection reagent that binds to serum antibodies from the species to which the subject belongs (e.g., a labeled mouse antibody that reacts with feline IgG). In one embodiment the bound anti-*M. haemofelis* antibodies are detected using goat anti-cat antibodies wherein the goat anti-cat antibodies are linked to a detectable label including for example, horseradish peroxidase (HRP). In this way the "sandwich" can be used to measure the amount of anti-*M. haemofelis* antibodies bound between the capture and detection reagents. Sandwich assays are especially valuable to detect analytes present at low concentrations or in complex solutions (e.g., blood, serum, etc.) containing high concentrations of other molecules. As is known, in these sorts of assays a "capture" reagent (e.g., a peptide of SEQ ID NO: 1 through SEQ ID NO 60) is immobilized on a solid support such as a glass slide, plastic strip, or microparticle. A liquefied biological sample (e.g., serum) known or suspected to contain the target antibody is then added and allowed to complex with the immobilized capture reagent. Unbound products are removed and the detection reagent is then added and allowed to bind to antibody species that have been "captured" on the substrate by the capture reagent, thus completing the "sandwich". These interactions are then used to quantitate the amount of anti-*M. haemofelis* antibodies present in the biological sample.

In other embodiments, the subject invention provides for diagnostic assays based upon Western blot formats or other standard immunoassays known to the skilled artisan. For example, antibody-based assays such as radioimmunoassays (RIAs); lateral flow assays, reversible flow chromatographic binding assay (see, for example, U.S. Pat. No. 5,726,010, which is hereby incorporated by reference in its entirety), immunochromatographic strip assays, automated flow assays, and assays utilizing peptide- or antibody-containing biosensors may be employed for the detection of antibodies that bind to the peptides of SEQ ID NO: 1 through SEQ ID NO: 60 or fragments thereof, provided by the subject invention. The assays and methods for conducting the assays are well-known in the art and the methods may test biological samples (e.g., serum, plasma, or blood) qualitatively (presence or absence of polypeptide) or quantitatively (comparison of a sample against a standard curve prepared using a polypeptide of the subject invention) for the presence of antibodies that bind to polypeptides of the subject invention.

Lateral flow assays can be conducted according to the teachings of U.S. Pat. No. 5,712,170 and the references cited therein. U.S. Pat. No. 5,712,170 and the references cited therein are hereby incorporated by reference in their entireties. Displacement assays and flow immunosensors useful for carrying out displacement assays are described in: (1) Kusterbeck et al., "Antibody-Based Biosensor for Continuous Monitoring", in Biosensor Technology, R. P. Buck et al., eds., Marcel Dekker, N.Y. pp. 345-350 (1990); Kusterbeck et al., "A Continuous Flow Immunoassay for Rapid and Sensitive Detection of Small Molecules", Journal of Immunological Methods, vol. 135, pp. 191-197 (1990); Ligler et al., "Drug Detection Using the Flow Immunosensor", in Biosensor Design and Application, J. Findley et al., eds., American Chemical Society Press, pp. 73-80 (1992); and Ogert et al., "Detection of Cocaine Using the Flow Immunosensor", Analytical Letters, vol. 25, pp. 1999-2019 (1992), all of which are incorporated herein by reference in their entireties. Displacement assays and flow immunosensors are also described in U.S. Pat. No. 5,183,740, which is also incorporated herein by reference in its entirety. The displacement immunoassay, unlike most of the competitive immunoassays used to detect small molecules, can generate a positive signal with increasing antigen concentration.

In accordance with the present invention a diagnostic assay for determining presence and/or degree of a *M. haemofelis* infection in a patient depends, in part, on ascertaining the presence of an antibody associated with *M. haemofelis*. According one aspect of the present disclosure is directed to kits for screening bodily fluids recovered from patients for the presence of anti-*M. haemofelis* antibodies. The bodily fluids include any liquid sample obtained or derived from a body, such as blood, saliva, semen, tears, tissue extracts, exudates, body cavity wash, serum, plasma, tissue fluid and the like that is anticipated to contain said antibodies. In one embodiment the bodily fluid is blood or a derivative thereof such as serum or plasma. In one embodiment the kit comprises a panel of immunodominant surface antigens of *M. haemofelis*. As used herein a panel means a compiled set of markers that are measured together in an assay. In one embodiment the panel comprises two or more peptides that comprise an amino acid sequence selected from SEQ ID NO: 1 through SEQ ID NO: 60. In one embodiment the panel comprise ones or more amino acid sequences selected from the group consisting of SEQ ID NO: 122, SEQ ID NO: 123, SEQ ID NO: 124, and SEQ ID NO: 125. Capture proteins compiled on a diagnostic chip can be used to measure the relative amount of anti-*M. haemofelis* antibodies present in a blood sample. This can be accomplished using a variety of platforms, different formulations of the peptide (e.g. phage expressed, cDNA derived, peptide library or purified protein), and different statistical permutations that allow comparison between and among samples. Comparison will require that measurements be standardized, either by external calibration or internal normalization. The assay format can range from standard immunoassays, such as dipstick and lateral flow immunoassays, which generally detect one or a small number of targets simultaneously, at low manufacturing cost, to ELISA-type formats which often are configured to operate in a multiple well culture dish which can process, for example, 96, 384 or more samples simultaneously and are common to clinical laboratory settings and are amenable to automation, to array and microarray formats where many more samples are tested simultaneously in a high throughput fashion. The assay also can be configured to yield a simple, qualitative discrimination (yes vs. no). The kit may further include a variety of containers, e.g., vials, tubes, bottles, and the like. Preferably, the kits will also include instructions for use. In one embodiment the kit may include additional reagents for detecting complexes formed between *M. haemofelis* antigens and anti-*M. haemofelis* antibodies including enzyme substrates, and labeled or unlabeled secondary binding agents. In one embodiment a labeled antibody specific for cat immunoglobins is provided as the secondary binding agent.

Typically the specific binding agent (e.g., *M. haemofelis* antigens) is immobilized on a solid support. After the bodily fluid (e.g., animal serum sample) is placed in contact with the binding agent and allowed to bind, the solid support can optionally be washed to remove material which is not specifically bound to the binding agent. The agent/antibody complex may be detected by using a second binding agent which will bind the complex. Typically the second agent binds the substance at a site which is different from the site which binds the first agent. In one embodiment the second agent is an antibody that is labeled directly or indirectly by a detectable label. In one embodiment the second agent is a labeled anti-cat antibody. Alternatively, the second agent may be detected by a third agent wherein the third agent is labeled directly or indirectly by a detectable label. For example the second agent may comprise a biotin moiety, allowing detection by a third agent which comprises a streptavidin moiety and typically alkaline phosphatase as a detectable label.

In one embodiment a method of detecting the presence or absence of antibodies directed against *M. haemofelis* antigens is provided wherein a sample suspected of containing said antibodies is contacted with at least two peptides (selected from the group consisting of SEQ ID NO: 1 through SEQ ID NO: 60) for a time sufficiently long to allow a complex to be formed between the at least one of said peptides and any antibodies present. After an optional wash step the sample is analyzed to determine the presence or absence of the antibody-peptide complex.

In accordance with one embodiment peptides comprising the sequences selected from SEQ ID NO: 1 through SEQ ID NO 60, or fragments thereof are formulated as vaccine compositions. In one embodiment a composition is provided comprising a sequence selected from SEQ ID NO: 1 through SEQ ID NO 60, or immunogenic fragment thereof, and a pharmaceutically acceptable carrier. In one embodiment the composition further comprises an adjuvant. In another embodiment, a polynucleotide vaccine is administered either alone or in conjunction with a polypeptide antigen. In one embodiment, the antigen is a polynucleotide selected from SEQ ID NO: 61 through SEQ ID NO 121. Methods of introducing DNA vaccines into individuals are well-known to the skilled artisan. For example, DNA can be injected into skeletal muscle or other somatic tissues (e.g., intramuscular injection). Cationic liposomes or biolistic devices, such as a gene gun, can be used to deliver DNA vaccines. Alternatively, iontophoresis and other means for transdermal transmission can be used for the introduction of DNA vaccines into an individual. In one further embodiment, the polypeptide antigen is administered as a booster subsequent to the initial administration of the polynucleotide vaccine. Accordingly, in one embodiment a method is provided for inducing an immune response to the novel immunodominant *M. haemofelis* antigens disclosed herein. The method comprises administering a composition comprising the peptides of SEQ ID NO: 1 through SEQ ID NO 60 and/or the nucleotide sequences of selected from SEQ ID NO: 61 through SEQ ID NO 121. In one embodiment the administered composition comprises one or more amino acid sequences selected from the group consisting of SEQ ID NO: 3, SEQ ID NO: 19, SEQ ID NO: 20, SEQ ID NO: 21, SEQ ID NO: 122, SEQ ID NO: 123, SEQ ID NO: 124, and SEQ ID NO: 125).

The present disclosure also concerns antibodies that bind to peptides comprising a sequences selected from SEQ ID NO: 1 through SEQ ID NO 60. Antibodies that are immunospecific for the polypeptides as set forth herein are specifically contemplated. The antibodies of the subject invention can be prepared using standard materials and methods known in the art (see, for example, Monoclonal Antibodies: Principles and Practice, 1983; Monoclonal Hybridoma Antibodies: Techniques and Applications, 1982; Selected Methods in Cellular Immunology, 1980, Immunological Methods, Vol. II, 1981; Practical Immunology, and Kohler et al. [1975] Nature 256:495). These antibodies can further comprise one or more additional components, such as a solid support, a carrier or pharmaceutically acceptable excipient, or a label.

In accordance with one embodiment an isolated nucleic acid sequence is provided that encodes a sequence selected from SEQ ID NO: 1 through SEQ ID NO 60, or a fragment thereof. In one embodiment an isolated nucleic acid sequence is provided that encodes an amino acid sequence comprising a contiguous 8 amino acid fragment of an amino acid sequence selected from SEQ ID NO: 1 through SEQ ID NO 60. In one embodiment the nucleic acid sequence encodes a peptide fragment comprising a contiguous span of at least 4, 5, 6, 7, 8, 9, 10, 11, 12, 13, 14, 15, 16, 17, 18, 19, 20, 21 22, 23, 24, 25, 26, 27, 28, 29, 30 amino acids of a sequence selected from SEQ ID NO: 1 through SEQ ID NO 60. In a further embodiment the nucleic acid sequence comprises a nucleic acid sequence that encodes a peptide fragment comprises at least an 8 contiguous amino acid sequence of a sequence selected from SEQ ID NO: 1 through SEQ ID NO 60 or a peptide that differs from an amino acid sequence of SEQ ID NO: 1 through SEQ ID NO 60 only by 1, 2 or 3 amino acids.

In accordance with one embodiment a nucleic acid sequence selected from SEQ ID NO: 61 through SEQ ID NO 121 is provided, or a nucleic acid fragment thereof. In accordance with one embodiment a nucleic acid sequence is provided comprising at least 6 nucleotides and having 75, 80, 85, 90, 95, 99 or 100% sequence identity with a contiguous nucleic acid sequence of a nucleic acid sequence selected from SEQ ID NO: 61 through SEQ ID NO 121. In accordance with one embodiment a nucleic acid sequence of 6, 7, 8, 9, 10, 11, 12, 13, 14, 15, 16, 17, 18, 19, 20, 21, 22, 23, 24 or 25 nucleotides is provided wherein the sequence has 75, 80, 85, 90, 95, 99 or 100% sequence identity with a contiguous nucleic acid sequence of a nucleic acid sequence of SEQ ID NO: 61 through SEQ ID NO 121. In one embodiment the nucleic acid sequence comprises a 6, 7, 8, 9, 10, 11, 12, 13, 14, 15, 16, 17, 18, 19, 20, 21, 22, 23, 24 or 25 nucleotide sequence that has 90, 95 or 99% sequence identity with a sequence selected from SEQ ID NO: 61 through SEQ ID NO 121. In one embodiment the nucleic acid sequence comprises a 6, 7, 8, 9, 10, 11, 12, 13, 14, 15, 16, 17, 18, 19, 20, 21, 22, 23, 24 or 25 nucleotide sequence that is identical to a corresponding sequence contained within a sequence selected from SEQ ID NO: 61 through SEQ ID NO 121.

In one embodiment a nucleic acid sequence is provided that can hybridize to a sequence selected from SEQ ID NO: 61 through SEQ ID NO 121 under medium or high stringent conditions. In one embodiment the nucleic sequence is a primer for use in PCR wherein the primer is 6 to 25, 8 to 20, 8 to 15 nucleotides in length. In one embodiment the medium stringent conditions comprise a step of washing the hybridized nucleic acid sequences with 5×SSC, 0.5% SDS at 37° C. for 30 min. In one embodiment the high stringent conditions comprise a step of washing the hybridized nucleic acid sequences with 2×SSC, 0.5% SDS at 45° C. for 30 min. In another embodiment the high stringent conditions comprise a step of washing the hybridized nucleic acid sequences with 0.2×SSC, 0.5% SDS at 50° C. for 30 min. In one embodiment the high stringent conditions include, for example, using a series of washes starting with 6×SSC, 0.5% SDS at room temperature for 15 min, then repeating with 2×SSC, 0.5% SDS at 45° C. for 30 min, and then repeated twice with 0.2×SSC, 0.5% SDS at 50° C. for 30 min. A more stringent set of conditions uses higher temperatures in which the washes are identical to those above except the temperature of the final two 30 min washes in 0.2×SSC, 0.5% SDS is increased to 60° C.

Furthermore, in one embodiment the nucleic acid sequence is inserted into an expression vector wherein a nucleic acid sequence selected from SEQ ID NO: 61 through SEQ ID NO 121, is operably linked to the regulatory sequences of the expression vector to allow expression of the encoded peptide. In a further embodiment a nucleic acid sequence selected from SEQ ID NO: 61 through SEQ ID NO 121, or any of the nucleic acid sequences disclosed herein, is operably linked to regulatory sequences that allow the gene to be expressed and the nucleic acid sequence is transfected into a cell. Accordingly, one embodiment of the present invention is directed to a host cell comprising a recombinant nucleic acid sequence encoding for a peptide comprising a sequence selected from SEQ ID NO: 1 through SEQ ID NO 60, or a fragment thereof. In one embodiment the recombinant nucleic acid sequence comprises an expression vector operably linked to a nucleic acid sequence selected from SEQ ID NO: 61 through SEQ ID 121. In one embodiment the expression vector encodes a peptide selected form the group consisting of P3-orf1165 (SEQ ID NO: 1), P6D-orf00908 (SEQ ID NO: 3), P7-orf0262 (SEQ ID NO: 8), P7-orf0263 (SEQ ID NO: 9), P10B-orf01747 (SEQ ID NO: 15), P10B-orf1749 (SEQ ID NO: 17, P10C-orf01238 (SEQ ID NO: 19, P10C-orf01239 (SEQ ID NO: 20), P10E-orf00279 (SEQ ID NO: 21), P15-orf00945 (SEQ ID NO: 27, P15-orf00946 (SEQ ID NO: 28), P15-orf00947 (SEQ ID NO: 29), P18-orf00128 (SEQ ID NO: 37), P21A-orf00675 (SEQ ID NO: 39), P21B-orf01544 (SEQ ID NO: 40), P24-orf01679 (SEQ ID NO: 45), P28-orf01521 (SEQ ID NO: 52) and P29-orf0177 SEQ ID NO: 57). In one embodiment the nucleic acid sequence encodes a peptide comprising the sequence of SEQ ID NO: 3, SEQ ID NO: 19, SEQ ID NO: 20, SEQ ID NO: 21, SEQ ID NO: 122, SEQ ID NO: 123, SEQ ID NO:124, and SEQ ID NO: 125, and in one embodiment the nucleic acid sequence encodes the peptide of SEQ ID NO: 20 or SEQ ID NO: 124. The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277,375, 5,643,570, or 5,565,335, each of which is incorporated by reference in its entirety, including all references cited within each respective patent.

In accordance with one embodiment a diagnostic assay for detecting a *M. haemofelis* infection in a patient is conducted using standard nucleic acid diagnostic techniques known to those skilled in the art, coupled with the nucleic acid sequences disclosed herein. More particularly, the nucleic acids sequences disclosed herein are used to detect the presence of *Mycoplasma haemofelis* specific DNA or RNA, including for example mRNA, in a biological sample recovered from the patient. In one embodiment a method of detecting the presence and/or degree of a *M. haemofelis* infection in a patient is provided. The method comprises contacting a nucleic acid sequence recovered or derived from a biological sample with a nucleic acid sequence selected from SEQ ID NO: 61 through SEQ ID NO: 121, or a fragment, a complementary sequence, or derivative sequence thereof. Detection of binding between the nucleic acid sequence recovered or derived from the biological sample, if such nucleic acid sequence exists in the biological sample, and a nucleic acid sequence selected from SEQ ID NO: 61 through SEQ ID NO: 121, or a fragment, a complementary sequence, or derivative sequence thereof indicates the presence and/or degree of a *M. haemofelis* infection in the patient. In accordance with one embodiment, the method of detecting *Mycoplasma haemofelis* specific DNA or RNA comprises the use of a standard PCR reaction and the nucleic sequences disclosed herein to specifically amplify any *Mycoplasma haemofelis* specific DNA or RNA present in a biological sample and allow detection of the amplicon using standard techniques. In one embodiment the PCR primer is 6 to 25, 8 to 20, 8 to 15 nucleotides in length and that has 90, 95 or 99% sequence identity with a sequence selected from SEQ ID NO: 61 through SEQ ID NO: 121, or the primer hybridizes with a sequence selected from SEQ ID NO: 61 through SEQ ID NO: 121 under high stringent conditions such as 30 min washes in 2×SSC, 0.5% SDS at 45° C.

In one embodiment the biological sample represents nucleic acid sequences isolated from a patient's tissues, including a blood, plasma or serum sample, and more particularly in one embodiment the patient is a feline species. Absent the presence of *Mycoplasma haemofelis* specific DNA or RNA, the PCR reaction will fail to produce an amplicon through the use of the *Mycoplasma haemofelis* specific PCR primers disclosed herein. In one embodiment a kit is provided comprising one or more of the nucleic acid sequences disclosed herein as well as reagents and a positive control for conducting PCR reactions. In one embodiment the kit further comprises a thermostable DNA polymerase.

In accordance with one embodiment a method of detecting the presence and/or degree of a *M. haemofelis* infection in a patient is provided. In one embodiment, the method comprises the steps of contacting nucleic acid sequences recovered from a biological sample with a nucleic acid sequence selected from SEQ ID NO: 61 through SEQ ID NO: 121, or a fragment or derivative thereof, conducting a PCR amplification reaction on the reaction substrate, and detecting the presence of amplified products, wherein the detection of an amplified product indicates the presence of a *M. haemofelis* infection in the patient.

EXAMPLE 1

*Mycoplasma haemofelis* infection frequently causes anemia in cats. Despite an intense immune response and/or antibiotic treatment, cats that are infected with this parasite often remain asymptomatic carriers. To date, no immunoassay has been developed, due largely to the inability to culture *M. haemofelis* in vitro. As disclosed herein it is anticipated that our screening for antibodies specific for *M. haemofelis* will provide a sensitive approach for identifying infected cats, particularly carriers. As a first step, immunogenic proteins of *Mycoplasma haemofelis* need to be identified that can be used for development of an immunoassay.

To identify *M. haemofelis* proteins recognized by the cat's antibody responses, two whole-genomic libraries were created in EcoRI predigested lambda Zap II. Chromosomes were digested to completion with EcoRI and partially digested Tsp509I restriction enzymes. DNA was size fractionated in an agarose gel and fragments in the range of 5 to 10 kb were excised purified and cloned into the unique EcoRI site of the expression vector. A prokaryotic (Plac) promoter is upstream of the insertion site. After plating on *Escherichia coli* in the presence of isopropyl-β-D-thiogalactopyranoside (IPTG) to induce prokaryotic expression, the *M. haemofelis* expression library was immunoblotted and probed with pre-immune and convalescent-phase antiserum from experimentally infected cats. The analysis of individual phage clones resulted in the identification of several genes (21 immunoreactive clones representing 60 open reading frames, orfs) encoding immunogenic proteins, which had been previously identified. Bacteriophage-mediated immunoscreening using an appropriate vector system offers a rapid and simple technique for identification of putative candidate antigens for development of an immunoassay.

Materials and Methods

Antisera.

*M. haemofelis* immune sera was obtained from random source cats that were inoculated with cryopreserved *M. haemofelis* organisms. Samples were collected immediately before (pre-immune serum) and post-inoculation for a period of several months (immune serum). Polymerase Chain Reaction (PCR) was used to detect the parasite DNA during the course infection.

Construction of Lambda Zap II Genomic Libraries

High-molecular-weight (HMW) *Mycoplasma haemofelis* genomic DNA (gMhf), collected during the peak of parasitemia, was purified using QIAGEN Genomic-tip 100/G kit (QIANGEN Inc., Valencia, Calif., USA) according to the manufacturer's recommendations. Spectrophotometry analysis of recovered DNA revealed that the dialyzed gMhf DNA was free of contaminants such as RNA, protein, and metabolites, and had a A260/A280 ratios between 1.7 and 1.9, making it well suited for use in library construction as well as subsequent use for development of an optical map and for complete genomic sequencing. Two *M. haemofelis* genomic libraries were constructed in Lambda Zap II (Stratagene, La Jolla, Calif., USA) according to the manufacturer's instructions. Briefly, chromosomal DNA from *M. haemofelis* was digested to completion with the 6-bp (GAA TIC) EcoRI and partially digested with the 4-bp (AA TT) Tsp5091 restriction enzymes. The DNA was size fractionated in a 1% agarose gel; 5-10 kb fragments from digests were excised, purified and ligated (Stratagene) directly into EcoRI-digested restriction site of Lambda Zap II DNA followed by packaging according to the manufacturer's protocol. The recombinant phages were plated onto lawns of *E. coli* XLI-Blue MRF' (Strategene) in the presence of IPTG and XgaI to allow for discrimination of non-recombinant plaques. The packaged libraries were stored in 7% DMSO at −80° C.

Screening of Libraries

The resulting libraries were plated and amplified on *E. coli* strain XLI-Blue, in the presence of IPTG to induce prokaryotic expression. Colony blotting is performed using standard techniques. Briefly, the plates containing bacteria infected with recombinant phage are overlaid with nitrocellulose filters previously soaked with IPTG and allowed to incubate overnight at 37° C. IPTG is used to induce and enhance expression of cloned mycoplasma genes by the lac promoter in the phage. Each filter is marked, the plates are cooled to 4° C., and the filters carefully removed. Nitrocellulose lifts were screened for antigen-positive plaques by first blocking the lifts with TBS-Tween (0.01 M Tris-0.14 M NaCl-0.5% Tween 20 [pH 7.4]) containing 5% skim milk and 1% normal goat serum (Santa Cruz Biotech, Santa Cruz, Calif., USA) overnight and then incubating overnight at 4° C. temperature with either diluted pooled cat anti-*M. haemofelis* immune serum, purified cat anti-*M. haemofelis* IgG (Protein A HP Spin Trap, GE Healthcare, Piscataway, N.J., USA), or non-immune cat serum. The lifts are washed 3× with TBS-Tween and then a goat anti-cat antibody conjugated with horseradish peroxidase (Santa Cruz Biotech, Santa Cruz, Calif., USA) was added, incubated for 1 hour and washed as above. Positive signals are visualized applying 3,3',5,5' tetramethylbenzidine (TMB) (Sigma-Aldrich, Saint Louis, Mo., USA) on the membranes for 5 to 15 min or until the signal is visible and the background is still low.

Reactive plaques were isolated and placed in centrifuge tubes containing 500 uL of SM buffer and 20 uL of chloroform and were replaqued using the same methods to ensure clonality.

Phagemid contents were excised and rescued with using ExAssist helper phage and Eschirichia coli SOLR strain (Stratagene). The plasmids were purified using QIAprep Spin Miniprep Kit (QIAGEN), and the insert DNA was sequenced using phagemid T3 and T7 sequencing primers.

The reactive clones were then sub cloned in E-coli SOLR strain using a helper phage (ExAssist helper phage, Stratagene) for rescuing. The ExAssist helper phage together with SOLR cells is designed for the excision of the pBluescript phagemid containing the insert from the Lambda ZAP II vector, while eliminating problems with helper contamination problems. The phagemid contents were excised and rescued according to the ZAP II instruction manual (Stratagene). Colonies appearing on the LB agar plates (with ampicillin) containing the phagemid with the cloned DNA insert were picked and put to grow overnight in LB media for purification. The purification was performed using QIAprep Spin Miniprep Kit (QIAGEN, Valencia, Calif.), and the insert DNA was sequenced using the phagemid T3 and T7 sequencing primers.

Sequence analysis.

After removal of flanking vector sequences, DNA sequences were analyzed using PHPH Web based tool (Togawa & Brigido, 2003). Comparison against GenBank nucleotide and protein databases was performed using BLASTn (Altschul et al, 1990), BLASTx (Stephen et al, 1997) and ORF Finder against the *Mycoplasma* genetic code on the network server at the National Center for Biotechnology Information (NCBI). In addition, Dense Alignment Surface (DAS) method was used to predict protein localization based on transmembrane helices (Cserzo et al., 1997). To determine whether the clone sequences have transmembrane proprieties, transmembrane prediction software as DAS and TMHMM Server were applied. Twenty one positive, immunoreactive plaques were identified; their inserts were analyzed using the software described above and results are summarized in table 1. The products of these genes are putative serologic and vaccine targets based on their reactivity with *M haemofelis* specific immune sera.

Plasmid Construction

Discovered clones from the Lambda Zap II expression library that encode Immunoreactive product were PCR amplified and Gateway cloned (PCR cloning System with Gateway® Technology, Invitrogen Corp., USA Carlsbad, Calif.). PCR products were cloned into pDORN™ 221 and transformed in *E. coli* strain OMNIMAX™ cells (entry clone), grown in LB medium with Kanamycin (100 ug/mL). Plasmids were purified (QIAprep Spin Miniprep Kit, QIAGEN) and sequenced to confirm the inserts were in frame. The inserts from the entry clones were transferred into the expression vectors by performing a LR reaction with pDEST™ 17 containing a His6-tag in the N-terminal end, as a destination vector. The pDEST™ 17-Mhfr recombinant plasmid were transformed into *E. coli* strain DH5α cells with ampicillin and purified as described above (expression clone).

Expression and Purification,

The expression clones were transformed into *E. coli* strain BL21-A1 cells plated on LB-carbenecillin (100 ug/mL) agar plates. Transformants were picked and cultured in LB medium containing carbenecillin, and the expression was induced by adding 2% L-arabinose, at 37° C. with shaking for 12-14 hours. Uninduced cultures were used as negative controls. Expression of recombinants was exanimate with sodium dodecyl sulfate-polycrylamide gel electrophoresis (SDS¬ PAGE, 15%). For isolation, the cells containing the recombinant proteins were harvested, and the proteins were extracted in denaturing conditions using 8M urea and native conditions by applying 4 cycles of freeze at −80° C. and thaw at 42° C. followed by sonication and centrifugation at 10,000×g for 20 minutes. For purification, the pellet was resuspended in extractor buffer (His60 NixTractor Buffer, Clontech Laboratories, Inc., Mountain View, Calif., USA) containing Urea (8M). The sample was sonicated (4 cycles of 5 sec) and centrifuged for 20 minutes at 20,000×g at 4° C. The supernatant was then applied to a His-Select nickel affinity gel column (Clontech Laboratories, Inc.) using the protocol recommended by the manufacturer. The concentration of proteins was determined spectophotometrically and analyzed by SDS-PAGE for determination of purity.

Western Blot Analysis.

In order to confirm the immunoreactivity of recombinants, the proteins from the SDS-PAGE gels were transferred to a nitrocellulose membrane using a TRANS-BOT® SD Semi-dry transfer cell (BioRad Corp., Hercules, Calif., USA) for 1 hour at 10 Volts. Western Blot analysis was carried out using dilutions of the cat immune and non-immune serum against *M. haemofelis*. Goat anti-cat conjugated with horseradish peroxidase (HRP) was used for detection of bound antibodies. Proteins were visualized with TMB (Sigma-Aldrich).

Results

Construction and Screening of Lambda Zap II Genomic Libraries.

The titers of the unamplified EcoRI and Tsp509I libraries for *M. haemofelis* were $1.1\times10^6$ PFU and $1.4\times10^5$ PFU. Following the immunoscreening, the strongest positive clones were grown up, phagemids were excised, and the inserts sequenced. The inserts were given an identification consisting of the letter P (plaque) and a number according to the order of discovery (eg. P5). If more then one insert was selected per plate, letters were added to the clone identification (eg. PlOA and PlOB). The clones selected from the plaque lifts and putative genes (ORFs) are summarized in Table 1. Twenty-two reactive clones were selected containing a total of 60 putative proteins. Sequence analysis shown that 26/60 putative genes discovered coincided with *M. haemofelis* sequences deposited in the GSS database (Berent & Messick, 2003), and the remaining 34 were never described before.

Sequence Analysis and Plasmid Construction.

Most of the inserts, when analyzed using the ORF finder tool contained several possible putative genes. The ORFs were given an identification number following the plaque name. The sequence analyses of each ORF are also included in Table 1. Based on the sequence analysis and protein characteristics such as transmembrane proprieties, sub cellular localization, and presence of signal peptide, 22 sequences were selected for plasmid construction for expression and western blot analysis. The selected sequences are show in Table 1.

TABLE 1

Immunoreactive clones of Mhf in ZAP II libraries

| Clone ID | Accession number | Sequence similarity-BLASTx against the Mollicutes | E value |
|---|---|---|---|
| P3-orf1165 | GS928052 | ACQ84443.1 adhesin [*Mycoplasma hyopneumoniae*] | 0.002 |
| P5-orf01816 | GS928053 | NP_853366.1 thymidine phosphorylase [*M. gallisepticum*] | 0.37 |
| P6D-orf00908 | GS928054 | ZP_06610317.1 hypothetical protein MALL_0643 [*M. alligatoris*] | 0.44 |
| P6D-orf00909 | GS928055 | ZP_06610593.1 hypothetical protein MALL_0515 [*M. alligatoris*] | 0.63 |
| P7-orf00259 | GS928056 | ACU78513.1 triose-phosphate isomerase [*M. mycoides*] | 8.00E−36 |
| P7-orf00260 | GS928057 | NP_073101.2 phospho-glyceromutase [*M. genitalium*] | 9.00E−128 |
| P7-orf00261 | GS928058 | BAH70152.1 hypothetical protein [*M. fermentans*] | 0.026 |
| P7-orf00262 | GS928059 | NA | |
| P7-orf00263 | GS928060 | ABD47695.1 adhesin-like protein P146 [*M. hyopneumoniae*] | 1.4 |
| P7-orf00264 | GS928061 | AAZ44718.2 conserved hypothetical protein [*M. hyopneumoniae*] | 0.22 |
| P9D-orf01202 | GS928062 | ZP_06610215.1 type I restriction modification DNA protein [*M. alligatoris*] | 2.00E−15 |
| P9D-orf01203 | GS928063 | YP_003303059.1 type I restriction enzyme specificity protein [*M. hominis*] | 0.005 |
| P9D-orf01204 | GS928064 | ZP_02931536.1 type I restriction enzyme S protein [*U. parvum*] | 4.00E−10 |
| P9D-orf01205 | GS928065 | YP_003303059.1 type I restriction enzyme specificity protein [*M. hominis*] | 2.00E−12 |
| P10B-orf01747 | GS928066 | YP_002284694.1 putative lipoprotein [*U. urealyticum*] | 3.1 |
| P10B-orf01748 | GS928067 | YP_003515875.1 hypothetical protein MAGa7180 [*M. agalactiae*] | 0.17 |
| P10B-orf1749 | GS928068 | NA | 1.1 |
| P10B-orf01750 | GS928069 | YP_003560289.1 hyalurono-glucosaminidase [*M. crocodyli*] | 1.1 |
| P10C-orf01238 | GS928070 | YP_002000188.1 massive surface protein MspK [*M. arthritidis*] | 0.004 |
| P10C-orf01239 | GS928071 | ZP_04563876.1 transcriptional regulator [Mollicutes bacterium D7] | 0.002 |
| P10E-orf00279 | GS928072 | NP_757929.1 hypothetical protein MYPE5440 [*M. penetrans*] | 3.00E−50 |
| P10E-orf00280 | GS928073 | NP_975564.1 pseudouridylate synthase D [*M. mycoides*] | 1.00E−41 |

TABLE 1-continued

| Immunoreactive clones of Mhf in ZAP II libraries | | | |
|---|---|---|---|
| Clone ID | Accession number | Sequence similarity-BLASTx against the Mollicutes | E value |
| P15-orf00941 | GS928074 | YP_002960937.1 hypothetical protein MCJ_004270 [*M. conjunctivae*] | 0.0024 |
| P15-orf0942 | GS928075 | NA | |
| P15-orf00943 | GS928076 | ACU78785.1conserved hypothetical protein [*M. mycoides*] | 0.28 |
| P15-orf00944 | GS928077 | AAO39838.1 AvgC variable lipoprotein [*M. agalactiae*] | 0.17 |
| P15-orf00945 | GS928078 | YP_002000023.1 massive surface protein MspF [*M. arthritidis*] | 0.63 |
| P15-orf00946 | GS928079 | ZP_02695921.2 hypothetical protein UUR13 [*U. urealyticum*] | 1.8 |
| P15-orf00947 | GS928080 | ZP_06610731.1 conserved hypothetical protein [*M. alligatoris*] | 0.37 |
| P15-orf00948 | GS928081 | YP_279005.1 lysyl-tRNA synthetase [*M. hyopneumoniae*] | 0.63 |
| P15-orf00949 | GS928082 | NP_758309.1 phenylalanyl-tRNA synthetase subunit beta [*M. penetrans*] | 0.48 |
| P17A-orf01526 | GS928083 | CAB62239.1 P75 protein [*M. hominis*] | 0.28 |
| P17A-orf01527 | GS928084 | ZP_04564868.1 conserved hypothetical protein [Mollicutes bacterium D7] | 0.002 |
| P17A-orf01528 | GS928085 | ZP_02971377.1 conserved hypothetical protein [*U. parvum*] | 0.37 |
| P17A-orf01529 | GS928086 | YP_016078.1 hypothetical protein MMOB3810 [*M. mobile*] | 0.37 |
| P18-orf00127 | GS928087 | NP_757967.1 hypoxanthine-guanine phosphoribosyltransferase [*M. penetrans*] | 6.00E−07 |
| P18-orf00128 | GS928088 | YP_002000162.1 hypothetical protein MARTH [*M. arthritidis*] | 0.13 |
| P20-orf00326 | GS928089 | NP_757466.1 DNA-directed RNA polymerase subunit beta' [*M. penetrans*] | 0 |
| P21A-orf00675 | GS928090 | NP_757933.1 translocase [*Mycoplasma penetrans*] | 3.1 |
| P21B-orf01544 | GS928091 | YP_002000128.1 massive surface protein MspH [*M. arthritidis*] | 0.044 |
| P21B-orf01545 | GS928092 | NP_757749.1 hypothetical protein MYPE3620 [*M. penetrans*] | 0.057 |
| P21B-orf1546 | GS928093 | YP_001256183.1 hypothetical protein MAG_0390 [*M. agalactiae*] | 0.097 |
| P21B-orf01547 | GS928094 | NP_975173.1 hypothetical protein MSC_0170 [*M. mycoides*] | 1.1 |
| P21B-orf01548 | GS928095 | YP_001799373.1 hypothetical protein PAa [*C. Phytoplasma australiense*] | 0.13 |
| P24-orf01679 | GS928096 | YP_002000015.1 massive surface protein MspC [*M. arthritidis*] | 1.13 |
| P24-orf1680 | GS928097 | NA | |
| P24-orf01681 | GS928098 | NP_758083.1 hypothetical protein MYPE6950 [*M. penetrans*] | 0.28 |
| P26-orf00285 | GS928099 | NP_853008.2 translation longation factor Tu (EF-Tu) [*M. gallisepticum*] | 8.00E−129 |
| P26-orf00286 | GS928100 | NP_757969.1 adenylosuccinate synthetase [*M. penetrans*] | 4.00E−110 |
| P26-orf00287 | GS928101 | ADC31594.1 ribosomal biogenesis GTPase [*M. gallisepticum*] | 2.00E−31 |
| P27A-orf1350 | GS928102 | YP_002000022.1 massive surface protein MspE [*M. arthritidis*] | 2.00E−03 |
| P28-orf01521 | GS928103 | YP_002961131.1 hypothetical protein MCJ_006330 [*M. conjunctivae*] | 0.130 |
| P28-orf01522 | GS928104 | YP_016010.1 SWF/SNF family helicase [*M. mobile*] | 0.630 |
| P28-orf01523 | GS928105 | ZP_04563267.1 conserved hypothetical protein [Mollicutes bacterium D7] | 0.220 |

TABLE 1-continued

| Immunoreactive clones of Mhf in ZAP II libraries | | | |
|---|---|---|---|
| Clone ID | Accession number | Sequence similarity-BLASTx against the Mollicutes | E value |
| P29-orf00175 | GS928106 | YP_001621362.1 ketose bisphosphate aldolase [*Acholeplasma laidlawii*] | 5.00E−102 |
| P29-orf00176 | GS928107 | NP_072863.1 co-chaperone GrpE [*M. genitalium*] | 4.00E−22 |
| P29-orf0177 | GS928108 | NP_758284.1 heat shock protein DnaJ [*M. penetrans*] | 2.00E−69 |
| P29-orf00178 | GS928109 | NP_109915.1 elongation factor G [*M. pneumoniae*] | 0 |
| P32C-orf00088 | GS928110 | ZP_03079605.1 arginyl-tRNA synthetase [*U. urealyticum*] | 7.00E−75 |
| P33B-orf01097 | GS928111 | YP_002000188.1 massive surface protein MspK [*M. arthritidis*] | 0.057 |

Expression, Purification and Western Blot Analysis.

The selected sequences, except for two, were PCR amplified and successfully gateway cloned. The expression was achieved culturing the recombinant BL-21 cells in 250 mL of LB media with 100 μg/mL of carbenicillin and inducing the expression by adding 20% L-Arabinose. Expression was checked by SDS-PAGE comparing between times before the addition of L-arabinose ($T_0$), and after growing 12-16 hours with L-Arabinose ($T_F$). The fusion proteins were western blotted using a goat anti His-tag (Invitrogen) as primary antibody to ensure the overexpression of the desired proteins.

Figure 1B:
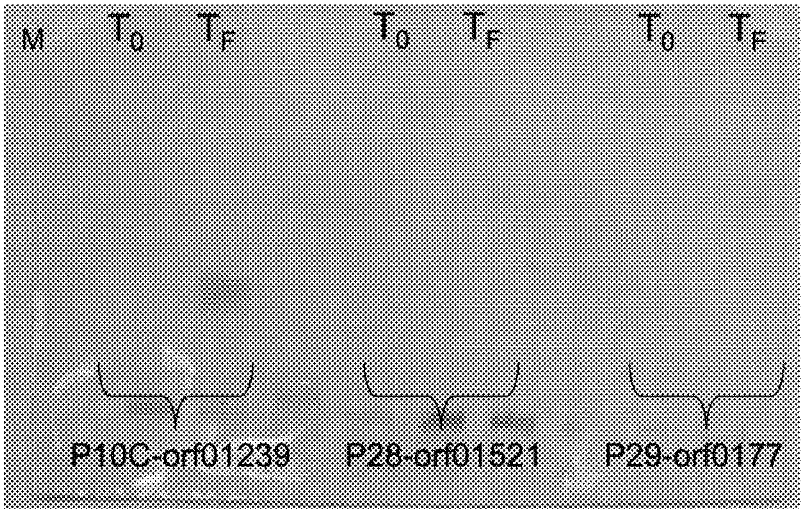

Eight out of 20 clones successfully expressed the fusion proteins and were selected to western blot analysis. Not all of the recombinant proteins were positive for the western blot probed with convalescent-phase antiserum. However, 4 fusion proteins (P6D-orf00908, P10C-orf01238, P10C-orf01239 and P10E-orf00279) were shown to be western blot positives when probed with convalescent-phase antiserum, and negative when probed with serum from SPF cats (See FIG. 1).

The western blot reactive proteins were fragments of the clones P6D-orf00908 (position 1-65), P10C-orf01238 (position 85-255), P10C-orf01239 (position 538-687), and P10E-orf00279 (position 1-159), with calculated sizes, including the 6 histidines (histag), of 18.65, 20.52, 17.49, 19.07 KDa, respectively. The fragment of DnaK (position 319-603), used as a control, was also reactive when blotted against convalescent-pooled serum and negative when blotted against serum from SPF cats, and the calculated size was 31.75 KDa.

Discussion

When *M. haemofelis* infects the cat, it elicits a spectrum of parasite-specific antibodies in the serum. Based on the hypothesis that detection of antibodies to *M. haemofelis* is a sensitive approach for identifying infected cats, particularly carriers, our objective was to identify, sequence and characterize genes encoding antigenic determinants of *M. haemofelis*. In order to achieve this, we used pooled sera from cats, collected at various time points throughout the course of experimental infection to perform immunoscreening of an expression library of *M. haemofelis*. Thus, immunogens expressed early in an infection, during parasitemia and in chronically infected cats could be potentially identified.

It is likely that many of the proteins encoded by the genome of *M. haemofelis* perform routine functions and are conserved across the different species of *hemoplasmas* infecting cat, including '*Candidatus Mycoplasma haemominutum*', '*Candidates Mycoplasma turicensis*' and possibly others. This feature makes them less attractive as targets for a serologic assay to diagnose *M. haemofelis* infection—the specificity of an assay using such antigen(s) would be decreased. To select more suitable candidates for antigen screening, various approaches have been suggested.

Since *M. haemofelis* cannot be grown in culture, only crude antigens preparations from blood of an infected cat can be obtained for electrophoresis-based methods. Several groups have reported contamination of hemoplasma antigen preparations with erythrocyte proteins, immunoglobulins and other host-derived blood proteins. Thus, the construction of expression libraries as a tool for detecting immune reactive proteins of *M. haemofelis* was the approach taken in this study. Once constructed these libraries it also could be used for sequencing and to study other genes, including those that don't encode for proteins that react to immune sera.

Applicants have successfully prepared a library of *M. haemofelis* DNA and have identified potential immunodominant antigens of *M. haemofelis. M. haemofelis* was harvested from blood of an experimentally infected cat using standard detachment, filtration, and centrifugation procedures. High-molecular-weight *M. haemofelis* genomic DNA was extracted and then purified by drop dialysis. Whole-genome sequencing was performed using GS-FLX (454) and Titanium chemistry to sequence a paired end library. First pass annotation was achieved using blast2GO and Manatee annotation tools. Genomic features of *M. haemofelis* were typical of mycoplasmas, including small genome size of 1,156,468 bp, low G+C content (38.8%), as well as the codon usage of the opal stop codon (UGA) for tryptophan. The gene order for rpmH, dnaA, and dnaN was conserved with the origin of replication in an untranscribed AT-rich intergenic region near the dnaA gene. 16S, 23S and 5S ribosomal RNA genes were located within the same operon as single copies. 55 membrane proteins were identified, including 9 lipoproteins as well as proteins involved in transport of biomolecules, DNA and energy metabolism, protein synthesis, and others.

Twenty-one immune reactive clones were identified in the expression libraries of *M. haemofelis* constructed in this study (see Table 1). Once sequenced, the correct open reading frame (ORFs) in the inserts were determined using a mycoplasma condon translation, where UGA is used to incorporate tryptophan rather than a stop codon. These predictions were verified against ORFs in the genome of *M. haemofelis* (data not shown), allowing for more confident translation of genes into their corresponding amino acid sequences. The amino acid sequences of these deduced peptides are represented by SEQ ID NO: 1 through SEQ ID NO: 60.

In this study, genes within inserts encode proteins necessary for diverse cellular functions and adhesion, along with several novel genes of *M. haemofelis*. Since there are often multiple ORFs within a given insert, selecting which gene and specific regions of these gene(s) code for immunogenic proteins is the next step. An array of web-based tools for the prediction of antibody epitopes in protein antigens and T cell epitope mapping of discovered proteins with tools recently developed for the cat will be used to select potentially immunogenic regions for further testing. In addition, analysis of proteasomal cleavage is likely to improve immunoinformatics screening for these epitopes. One of the last steps in this process will be to determine if only immune sera to *M. haemofelis* recognize these epitopes.

Of the 4 antigenic targets discovered herein, BLAST results showed that at least 3 of them are not represented in other organisms in the GenBank databases. Moreover, all the proteins were not find in the *Mycoplasma suis* genome (Accession number ADWK00000000.1; the only hemoplasma that has been sequenced other them *M. hamofelis*), supporting the hypothesis that these proteins might be unique for *M. haemofelis.*

Although UGA in *M. haemofelis* genes serve as a stop codon in *Escherichia coli,* 21 positive clones were identified in the expression libraries we constructed. Nonetheless, every ORF revealed the presence of UGA codons suggesting that truncated proteins are expressed in this system and at least some of these are antigenic. Protein topology analysis revealed that many of the proteins identified herein are located in the membrane, however several were cytoplasmic. It is possible that the latter genes are not coding an antigenic protein. However, several previous studies have reported cytoplasmic proteins were immunogenic. It was postulated that cytoplasmic proteins are exposed to the immune system after destruction of the bacterial cells.

EXAMPLE 2

Immunogenic peptides of *M. haemofelis*

```
>orf1165
                                          (SEQ ID NO: 1)
MSALAPLKLAGLSCLGVGGTCSVVYAGSSWVSGVSSLETDDDNVIQTVAD
KFSNRLIGKGKTSIWNARLQKLRSAGNSKQLDAGLKAIKDDTNKKDTDLQ
TWCEEAKIKPQEGEGSKLIVEGVQDYCTYTIKDQANGTMSKTKTNVSDWK
EVNTAFSKMKRDSLSKDLQAVWDKVKDKTDTSGDLKDWCFKKYDEPFEGR
DSATYKDVVKVCKTVPKPAAAKPAAAKPVASKPSSDSKQVAGTEPTSPAP
TKQAGDI*

>orf1816_1
                                          (SEQ ID NO: 2)
LDMSTLLKGSLGLLGAGSATTAGAIYLGTDIFKSKEDKKVSISKLLKTSN
PEKRLITSSQASDGDWKEAWKNYRVANKGKKLNEDEWKLSGWVTPQDGNI
TNTENASDSFMNTCSINKDKEVSGTDDPLYKAVLVYCTRSTLVSDLISDN
YPNKKILTSANNDDAGWKEAWTQYKTDNSGKSTQNSDAWQLAGWPTSTPD
TVLESFKTKCGEKVKVATFKTDNEDYTNAVKWCTK*

>orf0908
                                          (SEQ ID NO: 3)
VKAASGLGVAAATVGGGIFVAKGMEGSPSTPKSTVQDKLKQNGYSPLDLE
KSDGWSEVLEAYNQHKNNPSIRFDHGDREISEQELKDACSSAFNSDDKYE
NAKRWCVVPYSVSQVLTSKSLKVLNVNDTGDDDQDDQDEWDNLKGQYQEN
AIPGLVLKSTEDWQSLRTKCKELVEKKPWSDGYEDSISHATRWCTHAFVN
NSDS*

>orf0909
                                          (SEQ ID NO: 4)
MEPLKLAFLATGAGATGLGTYGLYSHLSGSQKENVGTRLVSESFELLNDS
HKAQWKTSLEKYNGKKDANASNIDETKLKAICKSLISKDKTSEADYKKAK
LYCVVPQGVSERLSKLGFKVLNTSDTTHQNEWTKLATSYVTNGKGDKQIE
SLTLTTPSGSTDNNWSTLKENCKTILGKSHWEESFDSYFEKSKMWCTEEA
FNSLPKEKQ*

>orf0259
                                          (SEQ ID NO: 5)
MKIVFGNLKMNFLYKDFQDYIENLRMKFLGETPKVHLGLAIPYIYLKSAS
ESIGSKIKVLAQDLHPVDFGAFTSSVSAAQLASLNVPATLIGHSECRQLS
QNSFVISNKIKSALRNGLEIIYCCGEDPEKEISEELFFMTEEEISKVIIA
YEPISSIGTGQAMDPSGADSTLLKIRDLIADKYGRKVADSMKLLYGGSVN
LSNYKGYLEKKNIDGVLVGGASLKVDDLWKMATLE*

>orf0260
                                          (SEQ ID NO: 6)
MDGWGLTSESKGNAPLLAKTPTLDFLYKEYPNSTLSASEEAVGLPAGQMG
NSEVGHINLGAGRVVYTGLSLINKCIKDGALESQPAVVEFFDLVKSRGSK
LHFLSLISEGGVHSNMNHFLAFADICVKRNQPYILHAFTDGRDVSPNAAK
TDFIPIVQKLKDTNGKLGVVSGRYYSMDRDKNWDREEKVFKYLVGSDKSR
TFDDVLVYIEQSYASGVTDEFIEPAICSSSLDSVIGDNDVVVFLNFRPDR
ARQISHMLVGSKGLYDYEPSVKLNNVSLFALMDYEKINLQNTLFPPFDIK
NTLGEFLSNNGISQLRIAETEKYPHVTHFFDGGKTLDYPKMKKILIPSPK
VATYDLQPEMSAPKITEALLPELKNFEVVILNFANPDMVGHTGSLEATIK
```

-continued

Immunogenic peptides of *M. haemofelis*

ACESVDTQIGKIYEEVQKLGGVLVVIADHGNAEVMITADGSPHTAHTTNL
VPFIVCKKGVTLRNDGVLGDIAPTLLSLLG LKQPVEMTGKVLVS*

>orf0261

(SEQ ID NO: 7)

MGKLVIFHKELRPDLSFFESFNHIEGVYFLSSDFKLYRFTDSLLVFFPPY
RVFNNHKIFKAGEVFVDCSQDSKDKYCSFSISPKSLSIPDCYNISTDSLG
ELDALIIDFEGSFIKESSLVRYSQRKLHFIRHTEINVRSYFYIEKVKKYL
VDRDLAINVFDSFSISEGFKSFERMPALRNFKSSGNAELSKFDDLNLDVF
DFCERKPDTSFKEESFFDSDEKIDPYYLEQLFKDPEFFKEIEKAKLSRIE
ETHKNDYLSRIEKAIRRSRALSISVPEYNYPTAPFDSFPENLNYLREIEN
FNEQEESAFKHIDLYTSYVSPMPLGRGVFIFRDLEELFDPYKGTINIPDI
EDEIEIMNAYIDEALDFYFKKEISEPPYFSWEE*

>orf0262

(SEQ ID NO: 8)

LLVLHKLFFSGEVRRFRNLLLEIEVQGFINICIHNLYLILYIRNIYGSFI
WIK*

>orf0263

(SEQ ID NO: 9)

VGGTKTSSSSATGSSCSSNDSSWTISCSSSINYSSQEK*

>orf0264

(SEQ ID NO: 10)

MEDEQEIVQEESLEEQEEPVAEEEEVFVPPTLEEVYDKSLFDNFSNLFYV
RTAPPSHFNWFLSPFVVHVFEFLTSLRRDRAMVFSHEENFDSQPIRDKYL
KDLSFLKSIEKYTHFPRFDYFISPFSYEYEKMFWTFTPYKKTMFTIQDSL
FFLNSEPFGPQGRCMFWESHALNHPEECQAYIRRIEIEVKNKYSALNRAY
EVFNRDLYGEYEDDFSMLDCPDINLGKFDKKARKEASKKVWYESEPPEAE
IERHQEPKK*

>orf1202_1

(SEQ ID NO: 11)

VSFKSFISEDENVRYFRLGDVCKIYAGISFKSSFYRDRGFPIIKTRNIQD
NQIVTGDLNYCDLANHKDAMIIKHGDVVMAKDGSCCGKIGINLTDEEFLF
DSHVLQFIPNEKLLIKRYLYHFLLSCQDKIRELAVGSAIPGIRKSELEKI
KIPVSSLEVQEKVASTLDKFREIEREISLRDKQYEYYRNYLIMGSHDSH*

>orf1203_1

(SEQ ID NO: 12)

LSIQADIASKLGKFQELKEELKEELLLRKKKHNYYRRQIWKTHLNGVQGL
KL*

>orf1204_1

(SEQ ID NO: 13)

VFKGFLKAEVREFLLEDVCNIQNGYSFSSSKYRSTGHPIIRIGNIQGTQF
KVEDLVYFERDDYKEDLSRFIIKPQDLVITARGSCGKVALNKTDSSFYLN
QGVWRLDPNPLFLNREYLFYFLSNSDLSSMVIKGHIPRLNVNSI*

>orf1205_1

(SEQ ID NO: 14)

VSFKSFLSESKDVKHLKLKDVCKIIAGKRFTPYTSEGMPVLRSGNIIDGY
VVDEDFVYCDREKHPRVDTVKYGDILIVRFGSAGVVGMNLINREFFLDAN
LSKFSPDSKILHKQYLYHFLLSRQEEIKGWARGAVIPAIRKSDLEELMIP
VPSLEQQQTIASKLDKLVELKRELILRKEQHSYYRKQIWEACSNGCSK*

>orf1747

(SEQ ID NO: 15)

MSLLTKSALGFAAAGTTAAGAAYAGGLFDGKEKEKTSISKLLQSLNPEKR
LIMASEGSDPLWKEAWKNYKVKYSGKGLDPLKVLSGKALASDESAPADFM
SSCKDLFDVKVVDGKDDSYQLVLNHCTRLTLVSDWIADRGHELVSQTEGD
ATIWKDLWKKYKDAGKNAWSVSEYSSYQDG*

>orf1748

(SEQ ID NO: 16)

MTPLTKAASATAIAGTAATGGIYLGTDLFKDKKVEIASLLKTAYPNKRLI
TSKTVSDDAWKKAYKAYREANKDKTKDIWSLKDWTKPQATVEETNATDDF
ISKCNSNSKLSVVGKDDPLYKQVLAYCTRDTLVSDLISEYGKGKKLLSKD
GSDQDAAWKAAWNVYKTRNKDKGENLDPWKLNNWNTKKSGDELPDNYKDK
CVEYSKKAAYQLEDENYKNVLDWCTA*

>orf1749

(SEQ ID NO: 17)

MTSLSKAALGFSAAGTTAAGALYMGGAFKGEEEKPVKTAISKLLKELNPK
KRLIESSVQASDAIWKAAWKAYRTKNKDSKVGEDTWKLKGWTTRSNEAQI
TEEEAPPHFIQACSDNGKEEVIGINDDLYKEVLEFCTRDVSIKDWISDAG

-continued

Immunogenic peptides of *M. haemofelis*

RSAIGKEDTEGWKKTWKLYRAKNKDIAAGQDTWKVSSWDPKTTSDDNVVE
DFKTKCTSKLDLKSSDSSFDEEYPRVLEWCTK*

>orf1750

(SEQ ID NO: 18)

LRDSWGDMTALTKAASATAVAGTAAGGGIYFGTDLLKSKKVDISSLMKEV
DPQKRFITATSTGDDSWKAAYKSYRESGKDVWGLGVKTASPETLIDATTE
FLAKCKSNGKVKVSGKDDPLYKQVLAYCTRDTTVRDLIEEGKTGRKLLDS
SDTGNDKESGWEDAWTAYRTKNHVEGGTSQNTWEVEGWDNKKTGNTLPTD
YKTKCAEKAKQPAYRLEDENYKNVLAWCTK*

>orf1238

(SEQ ID NO: 19)

MINKGIAFTTIFLSGSLYSFGSFIHDWQDYQFQQVEGSGILQDKRRGSFL
RGELPFTPSFRDRLAPSHIQKTSFQQHKHLFAPEMQKYLTEVNEEDIKEG
HYSSKKKELLDLIHYKKEWILTSDKEISYKSGYFQEKLNNFGDNKLVQDI
LWSLVEESQVNATLIRPESITINFKREKVGYQKNPLLDKSDVIKNLHIKF
RIFNPNRQKTFVFKSIEIDPTSETDVEITLREGELKPVSTALAALAAHKL
SASSWSIFPIEEGFKVTKEVVYPNKVKTQEHKDSLFLLYNSSRFFEKWVG
NPRSRSVSTHTHSLVDYEYVRKSLSAKLVNITTDQVKKDIERWYGSFTAF
ILRTKIEDMINLINLLQKNTFFDKRGNKVSVVDNAINDFTFRHNLYNHFQ
FDSNLRKVLDTLFLQNKNKPELKITVKEAKALLNSWVYQLEQIKDSIRIE
LKWEKEPQKTNADLGYENIYPAFSYKFTQKFVFTKEVKIPLKGTYNTTEN
KFEEATTETENKHKFDLSNRLKNVKVFLTPISFLFNSMNGGSIGGVSIMD
VLIPDVANFVDLESLTIDANQEIKNTYESKNSPITLAIGGEEDMQKIHFP
GTNIGWKSLDVTHSQDLSKFTKLFYKLYEKFDTYKDKSNQALGALQLLKE
NSRLKADPISFIAHAINSLFDKNYLQSKVSEESKRPWPVFFNSLLGKPLD
FKSRQLLTGLSSLFFEWDKEWDSKSEEDKCDGQGQGQGQEKYYCTKFSLK
NSRKKQILPNSEETKNVTQKFFPTYSSYFPEKPVVFGTTDDTTAYDAFLA
KEGKSSIGLVNNYTKLKEVFKSRFEKDPNFFPSNKEINWNNAKVSYVRLD
LEKAIKSVLALENTAYGGLGLMVSAVGIEFHKILGEALVRDGFWINMNLM
DEKGSFWTIEHPIKHMFYSPFSESWLFVKPDLDHTKLELGTFSTKRK*

>orf1239

(SEQ ID NO: 20)

VFFILPSRRKLAIGAGGIFFASGFIYFRVAEKEPFEKIEGSLPLRNKNKL
NFQDKQLSLQGFLKQDHLYSQNYQVFDPSIRKYLEIPISPRRVEESGNLF
KAFNSLKGWNRTASTISDRDLSYRDNPFIGGVNSLKKEEIIRDILESILD
ESEYLSTLIRADSIKIEFKKEEGFSLVKDFNLRLRILNPRKRKAYLFKSI
EIDPLSENDIHISLSQSEIKPTTVSVNLGHSKQISWSLFPKDSAWKITKI
THSPNHRKTEETKFSLPLIYGTSAALKDLQELLPRKEVDHPFPIASSLDY
GYVREKLTPLLVNISENQMEKDIEAWFGAHKAHQIRVYISDLQNLIEMFK
KRSFLDKNGRKASLIEMVMKSHTFKDGLYNHMKLSSSYRKVLDSLLTSEG
KELKLTEEECYALLDSWSYQLKQMQDSIKISITWDEKPKRVIQPLGYTSP
YPAVSFKFKQKISFEKAVKIPLNGSWDSSQKKYDASSGDQKFDITKRLSS
LGTILAPIRSVFKEMGNGGSFMGADIFDVLMPDVSQFLGIDGLEIDANEY
IENIYEASNSPIGIAIGDSEDYQGINIKGKNIGWKALDVSSSINLANFSK
FFYKLYEKIDTYKDPSNSALGVSQLWNFTTLLQQRPISFIIHAIHSTFDH
QYLKSGNSTSEDKRPWPVFFKSLFQDPITLKHKQVFVGYSGAFFDVKEWF
RSETKSSEQYSTSWDISTKKQRDEWEILSPKNEDVALINQKFALNYSSFS
PEQPIIINSEENKSQYDAFLAKEGSTSIGLVNHYDRLKSVFRDNNKSNIY
YPNIDWENMKVSYAQLNLEKAIKSVLAIRHTFQGFSSLTLTALGIEIHKI
LGEALIRNPFWINMNFMKEIGSWSKNEIPFKYMSYSVYSEESLYITPQLD
KTKLNLGRFIKL*

>orf0279

(SEQ ID NO: 21)

MDGQEKGKKDIANDPEVRKELEAYEKYILQQKHEIFNRIILNAIHTLKIQ
QPIISCCKRIDLSSLPGFNEETIGQLLGKDGQHKQHFINLTKVDLQVDQK
CPNHGIVLSKYNSVNVEKAVELVKKLLELKSWNLEKMKSLYEKVNKEFED
KCNKIGGQWLEQFLGYENYPDFLATHVGTLQFVYSFSQNILEHSIEVAQL
SANIAFQLGLDPLKAKRAGFFHDIGKAKANLGDHVDEGLKIGQEANFEEY
ILNAIESHHGRVPPNNPYSIIVKAADKLSAGREGARPRQIELIDKRRKMI
EDKIMSIPWIEKTIIKNAGNLIQIFIKPAEFHGDKILEMKEEVRAKLKEL
KAEYSYNYQI EFHLVFKEEFKFSE*

>orf0280

(SEQ ID NO: 22)

VSSYSIIFENKNFLIVNKASGIAVHKNIYDREFNLINEVNKDQKANYSLV
HRIDKYTSGAVLIAKNKETLLLLQNLFLNNEVEKHYLALTSKELPAKKLK
ITLSLGRSKNDKLRFTNRNAKNYKPACTEVEVIDRYFLKILLKTGRTHQI
RAHLFSINCPVLNDPIYGNRCFNPEFGQYLHAYKLEFTCPITNEFISVTA
PLPQEFKDKLSELNIEYTE*

-continued

Immunogenic peptides of *M. haemofelis*

>orf0941
(SEQ ID NO: 23)
MALAGATGAAGGGVLVHKLINKGEDTKSNTISNHIKPEYLLTNTHASQWT
HRLNLLGKAQETDLSEALLSFKKGKSSLTTEDLKGWCESSLKSEFKSKED
KKFLNTRLYCGLNMGDSIQENKVSSTTENGNTGLKSQFEKLKTKKVTELV
SALFAIKDKNNADSSWEGNVALKDWCTKALDMPMEEGLTYDNAKEYCVLT
AS*

>orf0942
(SEQ ID NO: 24)
VAAVPVAANAPNPFKSDVFMTKRVDKYKTPKLPCKPFHLY*

>orf0943
(SEQ ID NO: 25)
MKTSLLKGLGAFAATGTAATGGFVAWKQATKPTDVKSRLVWEGLTVADVN
GKGVWGAIYLAKKDVSGFLDFATTKDNKETASAQLKKKCSELFNVSAGDE
KYEESYEKAKKWCLNPELTTIEIQFEFEDREFASGDDDFKNLFTLYKGTS
SFVDVVKTSARDFTAQTALETAKGNVQTWCNSMKSKSPKGDDLKNAISWC
TKPESNFKSFMEKKGFRLLADGEWGNHFSSLKSKGGDTALDGDIKSETGS
DDGSKLKSWCDKKNVGTVQIHTLSADLEKIEGRCFVRK*

>orf0944
(SEQ ID NO: 26)
LIWDGLSVADSKSLGVYKAIYLANSDKAGFSSFVSASDKEKAAPLLKTKC
DDLLGISASSDKYAQSLEEAKKWCLVPKKTTIEISLLVDGMELSSADDDY
KNTFALSRSSQDFINAIKKGSDGLTTSSDVNTGFSKVKEWCAEVIKKSAF
DKDAQNAKLWCVKPDSKLGDFMDKQGFKPVESTGWDSHFTSLSSDNTLTS
DMSSVSGTEGNGNKLKSWCEGKNLANVQIHTLLTDLEKIKSRCFVRK*

>orf0945
(SEQ ID NO: 27)
MSSALVKGLAGVSAVGGVSAGGFFAYKNFQSQNIRDVLVGKGLTVANVNS
VGAWKVIAMGNKDNDAFFTFLGITKTSDRKVAGSKLQERCGSILNASIKD
ENYSSLLSKAESWCIQPTPKNLEEQLLMDELETDLSDDDFKNVHKILAQD
KAFTDAIEVTKGTESDGYKKVKKWCEVELKKPANSPKDAAKSRCATPFKN
LREALNSGGLSLISSAEDWSSRYSSIKGTDTSLSSDQITDSDGKGGTSLS
TWCSTEVDKKIHELTSNYTEHLDKVKKRCVTVKL*

>orf0946
(SEQ ID NO: 28)
LNLNLEGKASKLAWGLGIVGSLVLIISSIYWISPTVQDSLEDQELQLISK
SNESIDLYKRSFKRHKNTLISIGVDDFINENTVEDEGSVALHIWCDANLR
SKRWLVNLDGYKRFCALSMGDVLWLDKKDEGIINSHRFFILEEEDKRFSS
RLFSKFGLTWKNDKHIDNYEIWKSRCESELSEPYSYLNKHLKTDIKDNC
F*

>orf0947
(SEQ ID NO: 29)
MNTLAKGAIALTGAGGAAGGGFLISQNLGKTDTIANHIKKEYLLTSEQTD
KWNHRVGLLKKAQEGGLDSSLLPLKKEGLTNSELQTWCANQLKEKFEGLG
SNKFLNVRLYCGLNMGNKIAGNKVSSSTSDSENKLATNFGKLNGKTEQEL
GSALLEIGKKTNQSSGWEGNKALKEWCLKTFDLAFEETSKDYANAKTYCV
LV*

>orf0948
(SEQ ID NO: 30)
MEISGLFKAFLALAGVTGAAGGGVLLHKVINKDTISKHIDPKNLLTSAQQ
DKWTHRLGLLNKAADTDLSKDLLSAKKSKTTLTIDDLKSWCASNLESEFL
GTKDKKFKNIKLYCGLNMGDKIQGTKVASTTGGDNSSLKTNFGKLKNKTS
SELVSQLFSIRNADNTNSPWSGSTSLRDWCLSAFDMPFESGLTYDNAKDY
CVITD*

>orf0949
(SEQ ID NO: 31)
MSAKTTLLKGLGASATAGTVATGGFFAWKGLSQTSDITSRLTGEGLSVAD
VNKKGPWRVIYLTKKDVEGFSDFVDASDQENAVSQLQKKCSELLSASPQD
ENYEKSYEQVKKWCVNPELKTIEMQFVFDEREWAAAGDDFKSLFTLHQND
GNFINAVQSSTGFFNASMVLDEAKTEVETWCNSLKSKTPEGDDLQNAVSW
CTKPESNFKSFMDKKGFRMLNESEWASRFSSLKGGQDSDLSTDVSDDDSD
GSKLKGWCEGKKLDTVQIHTLGSDLNKIEARCFVKKE*

>orf1526
(SEQ ID NO: 32)
MELSFAAKMSTGAIGAGSIAGGGAFAAYKFLNQETIEKYLNSLHRELATS
NEDWELIKNNYAADKEDNPIPNIPKASIGDKLNDLKKWCSDHLNEEFSQE
KASKGDYNLIQSWCTKQVKISSYLKHLKLEALETIGTKDNERWTKLKDSY
PNGSLKVHEINTSGNTKSEGNAVDNLSGSDQKIKDWCSWASDQYFRYKED
TLFKRYEYFCTKPA*

>orf1527
(SEQ ID NO: 33)
MVSKAGVAAVGALGAGTASYMGYEYVFNSKEEVKKTTIRERLGDLLLDTS
SSDKWAARKTKLSQAEDTSLVEELKSLKNGVSEDQVKGWCSGAATKTYED
VSALYFENVRTYCTFYIEDKLPEGYITKDSQDWSKASDRLKNVQTGVALS
DQMKAIKDKLTTQGSSGTNDDLKNWCVGVYEKPFLGEDNQDFVDAKVYCA
KIETTSTGSVSPAAA*

>orf1528
(SEQ ID NO: 34)
MLMLGVAGTTGTAGLGFLIAKNQKDESQKLRSKYPHALLTLDSDSSWSDK
FNLLKTKTPSHPILKQAKTQFSNTQQSQSLYKKGCNAIYDSEGTQYLEDF
KTFCAKTNKDGITGTWIKGGADVNTKWDEKLTNLKKSTDKLSSRFLEVQQ
SLSSDSFNDEMRTNIQKACDNANSEIYLGSESVETRNIKNFCLTSES*

>orf1529
(SEQ ID NO: 35)
MNPEMMKGAYALGAASAIGGGAFTAKYIYDRSSSISIESHLKSKNLTVIS
SLNSTSQWEEEYKLDKDAIKAEIQITNDNEGGTKLKEWCSQQLSKPFKEG
EDLSKIERWCTVGKISQRIPKGKELLQDGAESSEWEKLYNKNTDQSERSK
LSLASSKEDGTKNSDLTAIKKFCSDNKDKPFLADRKATEYDLVILWCIK
Q*

>orf0127
(SEQ ID NO: 36)
MSCSCEKPSVSNVHLDLGYWFQVYSAYFRYFLIKGRIGEDTFESFIKKFE
SLGLKFGCEASLDFKSLNRELDSELSPEERDLLSQINEVEATEAAEKLAI
KDICDYQVRDFYDHLNNFKKLAFDFRYLSENSDSSNPLGIQFSIYFKDLQ
LLVDKFQSNRRFVESFNFETDINGSDSFEILNFLTRELDLFPVQFQSYSS
CNWFFLAIRELARFAREVAGFVQLHGFSLSLGDMDEYLLSNVIEACDRVE
KNSENVSCSLESFKIMMIDISNLFSNLNKVCLNIKPDEEFWKPCESNEHL
DSLYLKIFSPHLLEENLNYIFLNEPEIRNIVNKLSSKINEGCAHHGDPVC
LIFEQRESIPFIGQLLPYLDFPCTLVPLEDLSKESVERCEGVLDGRKAIF
LGTLLREASYIDKIKESIMKEDLKIGFLFVFDSLASTPIDIDFLGECIPD
EDWVGFGLGSKHKCCNLNAIGVLRE*

>orf0128
(SEQ ID NO: 37)
MHNDIRVHLKYLAEILKDTLNKMVFMGKIEFPKKLEAYANLWKEEFKDPF
TIPLTEAEWQDIKGIAPQFRGNRELQSSIKNVKRTLERQQFRNLSILNLM
DEKLNLYMHILETNRQLSLLTRSSQDEVAYISKDFKKRRLMGCQYIHREV
KNVTKLTKKHVIVNDIGSYINMFVDFSVKELEHLTHFIKIIRGIVDETIV
GEKLALLKTRIREGSFDLPSFRQYMKLESSVNKK*

>orf0326
(SEQ ID NO: 38)
MARRSSSAFKSQSSPNDFTIKALQISLASPEYVRSLSKGEVTSFETINYK
SLRPEKGGLFCESIFGPIKDYECSCGKYKQVKYKGKKCEKCKVYITQSLV
RRDWMGHIELACPVAHIWMIKELPLPAKISLILGIKYKHVEEVVYFVNYI
VLDPGHLQVEGKTLFDPLEIIDVSNSKSSIASLAKLRTLLRTIYETIQKE
NPESYLTDLNYQQGRAYYKALSNSNLPFSIMDMFEYIEKHTGLKVGIGAE
AIYELLKKVDLESLEYKLTQELNVNFPSGLNYADPKVRKILSRLQVIRWF
KESKNRPEWMILKVIPVIPPNLRPIIQLSGGRFTSSDINTFYRRIIVRND
RLARILNFNVAHIISNNEKRMLQEAVDSLIDNSSRKKPLTARDRHPLKSI
TDHLKGKQGLFRQNLLGKRVDYSGRSVIVVGSELKMYQVGLPILMILSLF
KPFIIRDLIRKVDDNGVECVPIAANIKTASKMIMEQSDEIWPVVHKVIKE
RPVLLNRAPTLHRLSIQAFEPILVEGKAICLHPLVTTAFNADFDGDQMAV
HLPLSAEAVHEARSMLLAPWQILGPKDGKPIVTPSQDMVLGIYHLTTEDK
EAIGFGSLFATPDEVVHAYQLGKVDLSSIIAIGTSGFPKKRFPKSGILIT
TVGKIIFNSRLPEDYKFINQSEGMWVSENDILDYGVSRLDYINAYQEKEP
FAKSVIGRLIEDLYDNYSCQDLAPVLDSIKDMGFEYSTKSCTTISAFDVP
KFSDKQSLLEEADKLVEQQKSFFRKGLVTDDEKYKNVIAIWSSVKDKVSD
HIKNALKSKEFQSNPIVIMARSGARGNVSNFIQLSGMRGLMNKSYNYDQN
TNTKVVRDIIEVPIKHSFIEGLTVIEYFNSSYGARKGMTDTAMKTAKSGY
TTRKLVDAAQEVIVKVEDCGSNKGLIVEELRDKEHSMPIKTLKDRIVFKC
AHIDILHPETGEVIVGANEVITKEAADKIVAAGITKVQVRSVLHCRLKQG
ICQKCFGYDLTTKQMIDVGTTIGVIAAQSIGEPAVQLTMRTFHSGGVAGE
SNISQGFERLRQLFEIVAPKKWETSVISEITGTVENIEIRDDERVVTVSS
DINRREYNCDLNLPILVKKGQKINFGDRICDGSVDLKKLLEVSGVEAVRQ
YIVQEIWKVYWIQGIDVSEKYIEIIVRQLTSRLKVLSPNDSKWAMGEVVD
YSSFVDECAKLLLDGKTPPIATSIIFGLEEVPEKTNSFLAAASFQDTKKI
LTDACVRGQIDYLNSLKENIMVGNLIPAGTGLKSADEVISDERSNRNVFN
Y*

-continued

Immunogenic peptides of *M. haemofelis*

>orf0675
(SEQ ID NO: 39)
MTTAVKTSLLAGGAAAASGIGAIAYGDLLSFQTQKEAISSLLSKDPAKRA
IGTTEEEEWKKTWARYRDSKEDIWKLGDLSGDAPTEFKNACKSKLDLEVS
GSDSKEYKDFLLYCSRDTLISDLIKENSKGRVLLEGTDVSSTDWQNAWKA
YSEDSRNQKGESETNIWNLSDWKTQNSQQNAPQSFITKCSSNIKHPSHDI
HDPLYIDTVKFCTKDKTTAPASTNNG*

>orf1544
(SEQ ID NO: 40)
MAVSSLYKGAALLGGAGSVAGGYALATHLSSDKKQENKVTSTEDRLRSEG
YTPLDFTNTNGDGWSKIKEAYKLENSEDKRFSGVEKEGNNTLSGIRDSCL
RYLKEDSTNESNYKMSRRWCVVPISVKDKLGASNLLKSGTNESDDHSKWD
EVVKKNDKDANKFVTFSESGKSSDDKRAEIKKQCEAKAAIETTKEEFEES
LNQVNLWCTQAAGTAG*

>orf1545
(SEQ ID NO: 41)
MKGGVAAATVGTTATGAYVGSRYLTNTTSVSKHLTSSGYKLISSIKNPDH
LKLQWKEEFKSDKASIKSLLNLKEDDESKGGEALGKWCTSKLAEEYSDKV
DGLESVKKYCVIKTIKDWLIRNGNKAILTENQDDNSKWEATYNKRKQAKT
PRTQTGLTETWPADSGTDKKDTDLPIIKRWCKEKNDSDFLAYEDTYSHVK
DWCTESANA*

>orf1546
(SEQ ID NO: 42)
MPTLKTLVTFPIVGVSGAFIVSNLDLIFHDEPVNIRSKLIRDGFRLLSSD
SSYWELLLSKHEEESSLKEKLPILVNNLESFKVACEEVIQFTDLNTYYSQ
ASRWCVVPQGFEDRLKFIGNKEILESDGIWGDLVSKYEKDSNNSFVSSLG
SQSTQELKIKELQKFCKDTKEKELKTYDKD FSKDFPLFLMWCTKR*

>orf1547
(SEQ ID NO: 43)
MSIIPKIAMGTLGLGGVAGGGILLARNLGNKNTLASKLESEGFTLMGEGH
DQWSKTLAEYNKVKGTAEEAFKIASIDLTVDQLKEQCLSILKSESYSETD
KNKASRWCTIPITIQSRIEKQGRRVLNDVDDNQDDKDTWVSLVRKHLTSP
ESSRMSVSITDLQNDTVDDERIKAMKGGCRSLKSKTSLEKTYLNDYSKFQ
DWCSAPK*

>orf1548
(SEQ ID NO: 44)
MALSTLTKGSILLGGVGSSVGGYFLVNNLTSGDKKEAKAITSIRDKLTQE
GYTPLNFENTAGSDWEKIKTEYKKENTDTKRFSGVNKDDDATVLEGIKNS
CLQYLLGDSSNEDNYQLSRRWCVVPVSVQNKLKGRTFLNTEAGQPNNDGE
WDKIVTKHDSHPNKWIIFEASKSKEEKRTKIKEKCSAQAKLETTHTDFED
ALRNVDLWCTKESV*

>orf1679
(SEQ ID NO: 45)
MSKLIPASLGAMGVSGAGVGSYIYLTSSENKKEEKVMTFKEKYSHAPLDL
EGNTNDTIWSSKLTALKTGSPHHPDLISAKNAITPQGEDKAKPLHKEACR
KIYGSSSDNQDYFHDFKKYCSKLLGDLVTGTWISSDSNSNSSWDGKLNDL
ISKKSELVSQTLKSFAESLKTGSLTEEQRKTIKDWCSTQKDQLFSGEGDN
VIQEIKSYCTSN*

>orf1680
(SEQ ID NO: 46)
LTSPSKFNNAEGYLDLMEVIGASSGVDCHGLRAINPPAPKPPAPAVPSAA
KAPFPMLIRSAITLDLLYYVISFSRK*

>orf1681
(SEQ ID NO: 47)
MGKGAFAALGTAGAGGLGAGGLIALKPWQSTPDEAPITSIRSKYPSALLN
LEGDVNIWEKKYKALETKTPHHPTLQKALSTGKGTGANLTEAKSLLKSGC
RAIYESDSDNSNNFQDFKSFCSKTNEDATKSGKQWIADATSKADGNKWDT
VLTSLKGHNTWSLDSVLETLKKGVQGDSSSFPEARRKELKDWCDKAKLEV
FVGESSSEFQSQEAFCKAD*

>orf0285
(SEQ ID NO: 48)
MITGAAQIDAAILVVSATDGTMPQTREHILLARQVGVERMVVFLNKCDMV
EDVEMQDLVEMEVRDLLTSYGYDGSATPVVRGSALKALEGDEKYVQSIKD
LLGNLDEYVPLPVREVDKPFLLSIEDVLTITGRGTVVTGRCERGTLKVNE
EVEIVGLKETSKAVVTGIEMFRKPLDEVLAGDNAGVLLRGVNKDEVSRGQ
VLAKPKSITPHKKFHAQIYALKKEEGGRHTAFTKGYKPQFYFRTTDVTGT
IDLPEGSEMVMPGDNAKILVELINVVAIEKGSKFSIREGGKTIGAGTVVD
IVE*

-continued

Immunogenic peptides of *M. haemofelis*

>orf0286
(SEQ ID NO: 49)
VSCGEGQIVSVLGVFFGDEGKAKIVDYISKDFDYVVRYQGGDNAGHTVCI
GDRKYIFQLIPCGILQTKAFIAHGVVLNPESLLKEIQDLSECVEIKDRLF
ISDHAHVICDWNIAYDKFLENLRGSQAIGTTNRGIGPTYSNKALRLGIRV
KDLLDYDSLREKIDLNLKIYNVLFKSYGHPTFDLEVETKKYFEYGQKIKP
YLVDSYHWIYGELSKGKRFLFEGSQGLMLDLDLGTYPFVTSSNITGSLIS
GTSLSFRHFKRIVGVVKTYSSRVGNGEFITEIHDQDLSGYIRKVGNEFGS
VTGRPRKIGWLDLVALKYVVTISGITEIVLTLVDVLNNLGEVKVCNSYEY
SSKEPIPVYKSFKGWKEDYSSIKRYSDFSDEFKNFVKYIEDFVGVPVTII
SYGRSREDTLVRMNEN*

>orf0287
(SEQ ID NO: 50)
MKIKLELPSHVKHSISNLNRFKKEVDLVINVVDARASKTSNLNLYISRIF
SKSKILDIFSKSDLASSEGLENSFNFKIQSNRNRILHLIKKALQEERNRL
QESGYLNPHFKILVVGMPNTGKSTLINLLKNKKISKAANTPGITRKITQY
YLGDNLWLFDSPGIFFYQDISPELLWKLIVINAVPSNFKEYSEILEITFW
YLKDKYPNSMDELSADSYLSFIELLAKRYNFKNRGGTFDLERAEEKFLFL
LRNGGIRDVSWD*

>orf1350
(SEQ ID NO: 51)
LSNSSQNWLSLNLKTSLLVGAASISAAGTTSSVLSNASGGVLEAVKNSSQ
PIIDPFQKGYSKLSEQLDSFSKQGYNAGVDAKSWVTENLSKSKIKTGETN
IYQNLSDWYRAVKGFADSARTTISEFFQKWSEHRETMHVVFKALGNSFSL
LGGLMGSFESDGESGLKILFEVIGKPKFKDFMTQVSSLVSKNPNLMSSLE
GNDVMDVLSAFRQDEDTVVDTLKGLSEKDAGTVDKATLMNALKLYSLMDK
ARNLMSKARTILESKDKEKAKQLIQEITEAHKQMEALIKANEGQATE*

>orf1521_1
(SEQ ID NO: 52)
LGSMSLSLASKATAGIAGTGAVAGGGAFAAYKFLNQETIEKYLNSLHREL
AVSNEDWELIKNNYAADKAENPIPNIPKSTIKDKLNDLKKWCSDRLNEEF
SQEKASKGDYNLIQAWCTKQVKISDYLKHLKLASLDTSGTKDDTTWNKLK
DEYSTSGGLKVNEITGQEGSKTEGGEVSTLSDNTKLKTWCSWSVSQYFKH
QEDSLFKRYKHFCTKQAN*

>orf1522_1
(SEQ ID NO: 53)
MLSKAGVAAVGALGAGTASYMGYEYVFNAKEEVKKVTIGEALEPFLLNTE
SSDKWASRKDKLSKANEDSLVEELKSLKSGVTEDQVKNWCSVASTKVYSE
VSGLYLENVRSYCTFHIEDKLPSGYIKDTEDWEKANSRLKEVNPDTGLSS
HMKEVKDKLSKQDSPDTNALKDWCMGAYGKPYLGDDNQDFVDARTYCSKV
AEASPSGSTQAASLPA*

>orf1523_1
(SEQ ID NO: 54)
MSKLAALILGIAGTAGTAGLGFLIAKNQKDETKKIKNNYPHAILTFSNNE
GWNSKFQLLNSKETTHPTLKKAKAQFSNTSQSQELYKKGCNEIYDSEGTQ
YLDDFKTFCSKTNKDAITGSWISDAASVNTNWDKKLTSLKERNSGLSSEF
LEVQSSLGSGSFDETARGKIKKACDDSHSEIYLGPNDIKTQSIKDFCLSE
QT*

>orf0175
(SEQ ID NO: 55)
MALVSAREILLKAYKEGYAVAQINTNNLEWTKAILLTVQELKSPVIIGAS
EGAIKYMGGFRTVASLVKAMIEDLGITVPIILHLDHGSYEGCKKAMDAGF
SSVMFDGSHFPIDENFQKSKEIVDLANSRGISVELEVGTIGGEEDGVIGA
GENASVDECVKIGGLDLSMLAAGIGNIHGPYPDNWKGLNFPLLKEISDAV
KKPMVLHGGTGIPEDQIKKAISLGISKINVNTELQLAFAAATRKYIEEKN
DLNMSKKGFDPRKLLKYGYDGICQVIKDKLTMFGSVGKA*

>orf0176
(SEQ ID NO: 56)
MSKDNKEQKEEEIVEEVSELDQLKAKLKEWEDKFSELEKESNQRLLEFVE
KKSKEASDIIAKKEEEISQRYKKELEEAKDYLYEKPLASLVGVISQFEAV
IKMTVDPNISQYLVGFRMFLTQFNDLLREFSISIIEPKDGDEFDSSFMEA
TVVEKVSDDSLNNKVISVFSKGYRLKDRIIRLASVKVGKI*

>orf0177
(SEQ ID NO: 57)
MASKDYYSILGISRNATEDDIKKAYRKLAKKYHPDINKEAGAEAKFKDIN
EAYETLGDPQKRSNYDNFGTSGDGMGGAGGANPFDIWNSFFSGQASGGFS
EFDIFGGSDSHQSQPQYENYQDRIVISFLASIKGVNHSFTYESEKRCEVC
KGNKALDGDSKYIITCDNCRGTGWEMLRKQTIFGVVNTKASCRRCNGQGK -continued Immunogenic peptides of *M. haemofelis*

MISKPCKECGGRGYKKFHKTQNFSIPAGVQDKDVLVAWDKTGIVDKKISI
HVSVRPSEIFSRKGNDLYTRIVINPFVAIFGGTASIPTISGIKSIKIAAG
TNSGEKLKLKGLGVKSSAGRGDLIGEVCFAPVPKLTKEQKEVLKSLSDLE
VPEVTRWVSKAKKAVVSD*

>orf0178

(SEQ ID NO: 58)

MAHIDAGKTTTSERILFHTGKTYKIGEVHDGAATMDWMEQEKEKGITITA
AATSVSWKNHQLNLIDTPGHVDFTVEVERSLRVLDGAVAVLDSQMGVEPQ
TETVWRQATKYSVPRIVYCNKMDKIGADFFKSVQSLRDKLKVKAVLVQLN
IGKESEFTGIIDLIAKKAYSFDGKQEEEYKEIPIPDNLKGEVDRLHQELL
DEVLVFDEKIMEKYLGGEEVTIDEIKRCIRIGTIQTKLFPVFCGSSFKNK
GVKFLLDAIIDYLPSPVDLPETPAFDKEQNPISIKNSAEGEFVGMAFKIA
TDPFVGRLTFIRVYSGILKKGSAIYNTTQDLPEKAGRLVQMHSNHRTEIE
SIQAGEICAIVGLKNTRTGDTLTVKGNAVVLESMNFAEPVISLAIEPKTK
VDQEKMSMVLSRLSEEDPTFKISTNVETGQTIISGMGELHLEILIDRMNR
EFGLQVNIGQPQVAFRETFTQVSDVEGKYIKQSGGRGNYGHVWIKFEPNK
DKGFEFVDKIVGGKIPKEYIKSIRQGLIDAMKSGPLAGYPIIDIKATLFD
GSFHEVDSNEMAFRIAASLALKDASKKCASILLEPIMNVEITVPLQYFGT
VMGDVTSRRGLIEGTEQVENAQIIKSKIPLKEMFGYATVLRSFTQGRGIY
TMQFSHYQPLPKSITQEMLEGRK*

-continued

Immunogenic peptides of *M. haemofelis*

>orf0088

(SEQ ID NO: 59)

LQKIKDYLSSEFNLAAQALGYRLTGIEASFDFTKDYKFGDIFTNFACRIS
SKYKKNPKDVGEELLKQVGELKYVSSAKVEKNGFINIFFSPEIFSEYYSE
ILEKREDIWRKHPINSWYFVEIVSANPTGLLHIGHARNGIFSDTLANLLE
YGGYFVHREYLVNNLGNQIKELLESIWIKYKAKLTSIPRESNTKVVKYNG
KEIDECVDYLISTHGQRWIFDRNIFESKSYPELEKLVVSYFLNEIEKDLA
RYNIEVNAWKFESSFVNSESINDLFKSMKEYLRVKDGAIWFKAGEILDEC
KDEVLIKNDGKHTYYCQDLIYHLYKLSLLGNEGKIINVLGSDHYGHIDKL
KAFLKLKEVDDDRVHFICMQLVKLMEHSTLVKISKRDSKVIYLRDLMNYM
TYEEARWFLVSQHPDSPLEIDIQRLKQKNYNNPAFYVMYAYSRIFQILRK
HGEPYFYSKKEVLFKTITDGIEKTIMNTLMQWDEVIHEAIETLQPYRITQ
YLFKLAKEFHSFYEETKLLQEGHEEEWLRDRLALLNAAKYTIHSGLSILK
IKPKSVI*

>orf1097

(SEQ ID NO: 60)

MTYAKLGAATLGTAGAAGGGYLAYPHVFPERTLLDELKSQNKSVINGNES
QWTLKKELYNKGTNSSKITIDNKEKASITEAELKKWCSDNLKAPYSKAKD
SILGKVEKWCLKPNIKEALSKETKEIISFTGTTIDAAWESKLTTNSSSVK
GELIDKWKLPVSSEGNDKVSKESLRDACQLKVEGEYISENDENYTLSKKW
CLKP*

What is claimed is:

1. A peptide complex comprising one or more different recombinant fusion peptides and a solid support, wherein the one or more recombinant fusion peptides each comprises an amino acid sequence selected from the group consisting of SEQ ID NO: 1 through SEQ ID NO: 60 and a terminal amino acid sequence covalently linked at the carboxy or amino terminus of the one or more recombinant fusion peptides;

wherein the one or more recombinant fusion peptides does not encode a native amino acid sequence of *Mycoplasma haemofelis*; and wherein the one or more recombinant fusion peptides are immobilized on the solid support.

2. The peptide complex of claim 1, wherein the one or more different recombinant fusion peptides each comprises 1-18 different recombinant fusion peptides.

3. The peptide complex of claim 1, wherein the one or more different recombinant fusion peptides each comprises 1-9 different recombinant fusion peptides, wherein the one or more recombinant fusion peptides each comprises an amino acid sequence selected from the group consisting of SEQ ID NO: 1, SEQ ID NO: 3, SEQ ID NO: 8, SEQ ID NO: 9, SEQ ID NO: 15, SEQ ID NO: 17, SEQ ID NO: 19, SEQ ID NO: 20, SEQ ID NO: 21, SEQ ID NO: 27, SEQ ID NO: 28, SEQ ID NO: 29, SEQ ID NO: 37, SEQ ID NO: 39, SEQ ID NO: 40, SEQ ID NO: 45, SEQ ID NO: 52 and SEQ ID NO: 57 and a terminal amino acid sequence covalently linked at the carboxy or amino terminus of the one or more recombinant fusion peptides.

4. The peptide complex of claim 1, wherein the one or more different recombinant fusion peptides each further comprises one or more different peptides each comprising an amino acid sequence selected from the group consisting of SEQ ID NO: 122, SEQ ID NO: 123, SEQ ID NO: 124, and SEQ ID NO: 125 and a terminal amino acid sequence covalently linked at the carboxy or amino terminus of the one or more recombinant fusion peptides;

wherein all of the recombinant fusion peptides do not encode a native amino acid sequence of *Mycoplasma haemofelis*; and wherein all of the recombinant fusion peptides are immobilized on the solid support.

5. The peptide complex of claim 1, wherein the one or more different recombinant fusion peptides each further comprises one peptide comprising an amino acid sequence of SEQ ID NO: 124 and a terminal amino acid sequence covalently linked at the carboxy or amino terminus of the one or more recombinant fusion peptides;

wherein all of the recombinant fusion peptides do not encode a native amino acid sequence of *Mycoplasma haemofelis*; and wherein all of the recombinant fusion peptides are immobilized on the solid support.

6. A composition comprising two or more different isolated recombinant fusion peptides, wherein each of said isolated peptides comprises an amino acid sequence selected from the group consisting of SEQ ID NO: 1 through SEQ ID NO: 60 and a terminal amino acid sequence covalently linked at the carboxy or amino terminus of the two or more isolated recombinant fusion peptides; and wherein the two or more isolated recombinant fusion peptides do not encode a native amino acid sequence of *Mycoplasma haemofelis.*

7. The composition of claim 6, wherein the two or more different isolated recombinant fusion peptides each further comprises an amino acid sequence selected from the group consisting of SEQ ID NO: 1, SEQ ID NO: 3, SEQ ID NO: 8, SEQ ID NO: 9, SEQ ID NO: 15, SEQ ID NO: 17, SEQ ID NO: 19, SEQ ID NO: 20, SEQ ID NO: 21, SEQ ID NO: 27, SEQ ID NO: 28, SEQ ID NO: 29, SEQ ID NO: 37, SEQ ID NO: 39, SEQ ID NO: 40, SEQ ID NO: 45, SEQ ID NO: 52 and SEQ ID NO: 57 and a terminal amino acid sequence covalently linked at the carboxy or amino terminus of the two or more isolated recombinant fusion peptides.

8. The composition of claim 6, wherein the two or more different isolated recombinant fusion peptides each further comprises one or more different peptides each comprising an amino acid sequence selected from the group consisting of SEQ ID NO: 122, SEQ ID NO: 123, SEQ ID NO: 124, and SEQ ID NO: 125 and a terminal amino acid sequence covalently linked at the carboxy or amino terminus of the one or more peptides; and wherein all of the isolated recombinant fusion peptides do not encode a native amino acid sequence of *Mycoplasma haemofelis.*

9. The composition of claim 6, wherein the two or more different isolated recombinant fusion peptides each further comprises one peptide comprising an amino acid sequence of SEQ ID NO: 124 and a terminal amino acid sequence covalently linked at the carboxy or amino terminus of the two or more recombinant fusion peptides; and wherein the two or more isolated recombinant fusion peptides do not encode a native amino acid sequence of *Mycoplasma haemofelis.*

10. The composition of claim 8 further comprising an adjuvant.

11. A method of detecting a *Mycoplasma haemofelis* infection in a warm blooded vertebrate, said method comprising analyzing a bodily fluid from said warm blooded vertebrate for the presence of antibodies that specifically bind to the peptide complex of claim 1 or the composition of claim 6.

12. The method of claim 11 wherein the antibodies are detected via an immunoassay selected from the group consisting of enzyme linked immunosorbent assays (ELISAs), radioimmunoassays (RIAs), and Western blots.

13. A method of detecting a *Mycoplasma haemofelis* infection in a warm blooded vertebrate, said method comprising analyzing a bodily fluid from said warm blooded vertebrate for the presence of antibodies that specifically bind to the peptide complex of claim 1, wherein said method is performed using an array of peptides immobilized on a solid support.

14. A method of detecting a *Mycoplasma haemofelis* infection in a warm blooded vertebrate, said method comprising analyzing a bodily fluid from said warm blooded vertebrate for the presence of antibodies that specifically bind to the peptide complex of claim 4, wherein said method is performed using an array of peptides immobilized on a solid support.

15. A method of detecting a *Mycoplasma haemofelis* infection in a warm blooded vertebrate species, said method comprising analyzing a bodily fluid from said warm blooded vertebrate for the presence of antibodies that specifically bind to the peptide complex of claim 3, wherein the *Mycoplasma haemofelis* infection is in a warm blooded vertebrate species, said method further comprising obtaining a bodily fluid from said warm blooded vertebrate species;

contacting the bodily fluid with the peptide complex of claim 3; and detecting antibody peptide complexes formed between an antibody from said bodily fluid that has specifically bound to one or more recombinant fusion peptides, wherein detection of said complexes identifies a warm blooded vertebrate infected with *Mycoplasma haemofelis*.

16. A method of detecting a *Mycoplasma haemofelis* infection in a warm blooded vertebrate species, said method comprising analyzing a bodily fluid from said warm blooded vertebrate for the presence of antibodies that specifically bind to the peptide complex of claim 4, wherein the *Mycoplasma haemofelis* infection is in a warm blooded vertebrate species, said method further comprising obtaining a bodily fluid from said warm blooded vertebrate species;

contacting the bodily fluid with the peptide complex of claim 4; and detecting antibody peptide complexes formed between an antibody from said bodily fluid that has specifically bound to one or more recombinant fusion peptides, wherein detection of said complexes identifies a warm blooded vertebrate infected with *Mycoplasma haemofelis*.

17. A method of detecting a *Mycoplasma haemofelis* infection in a warm blooded vertebrate, said method comprising analyzing a bodily fluid from said warm blooded vertebrate for the presence of antibodies that specifically bind to the peptide complex of claim 5, wherein the *Mycoplasma haemofelis* infection is in a warm blooded vertebrate species, said method further comprising obtaining a bodily fluid from said warm blooded vertebrate species; contacting the bodily fluid with the peptide complex of claim 5; and detecting antibody peptide complexes formed between an antibody from said bodily fluid that has specifically bound to one or more recombinant fusion peptides, wherein detection of said complexes identifies a warm blooded vertebrate infected with *Mycoplasma haemofelis*.

18. The composition of claim 6, wherein the two or more different isolated recombinant fusion peptides each comprises a label.

19. A method of detecting a *Mycoplasma haemofelis* infection in a feline, said method comprising analyzing a bodily fluid from said feline for the presence of antibodies that specifically bind to the peptide complex of claim 3, wherein the *Mycoplasma haemofelis* infection is in a feline species, said method further comprising obtaining a bodily fluid from said feline species;

contacting the bodily fluid with the peptide complex of claim 3; and detecting antibody peptide complexes formed between an antibody from said bodily fluid that has specifically bound to one or more recombinant fusion peptides, wherein detection of said complexes identifies a feline infected with *Mycoplasma haemofelis*.

20. A method of detecting a *Mycoplasma haemofelis* infection in a feline, said method comprising analyzing a bodily fluid from said feline for the presence of antibodies that specifically bind to the peptide complex of claim 4, wherein the *Mycoplasma haemofelis* infection is in a feline species, said method further comprising obtaining a bodily fluid from said feline species;

contacting the bodily fluid with the peptide complex of claim 4; and detecting antibody peptide complexes formed between an antibody from said bodily fluid that has specifically bound to one or more recombinant fusion peptides, wherein detection of said complexes identifies a feline infected with *Mycoplasma haemofelis*.

21. A method of detecting a *Mycoplasma haemofelis* infection in a feline, said method comprising analyzing a bodily fluid from said feline for the presence of antibodies that specifically bind to the peptide complex of claim 5, wherein the *Mycoplasma haemofelis* infection is in a feline species, said method further comprising obtaining a bodily fluid from said feline species; contacting the bodily fluid with the peptide complex of claim 5; and detecting antibody peptide complexes formed between an antibody from said bodily fluid that has specifically bound to one or more recombinant fusion peptides, wherein detection of said complexes identifies a feline infected with *Mycoplasma haemofelis*.

* * * * *

SEQUENCE LISTING

<160> NUMBER OF SEQ ID NOS: 125

<210> SEQ ID NO 1
<211> LENGTH: 257
<212> TYPE: PRT
<213> ORGANISM: Mycoplasma haemofelis

<400> SEQUENCE: 1

Met Ser Ala Leu Ala Pro Leu Lys Leu Ala Gly Leu Ser Cys Leu Gly
1 5 10 15

Val Gly Gly Thr Cys Ser Val Val Tyr Ala Gly Ser Ser Trp Val Ser
20 25 30

Gly Val Ser Ser Leu Glu Thr Asp Asp Asp Asn Val Ile Gln Thr Val
35 40 45

Ala Asp Lys Phe Ser Asn Arg Leu Ile Gly Lys Gly Lys Thr Ser Ile
50 55 60

Trp Asn Ala Arg Leu Gln Lys Leu Arg Ser Ala Gly Asn Ser Lys Gln
65 70 75 80

Leu Asp Ala Gly Leu Lys Ala Ile Lys Asp Asp Thr Asn Lys Lys Asp
85 90 95

Thr Asp Leu Gln Thr Trp Cys Glu Glu Ala Lys Ile Lys Pro Gln Glu
100 105 110

Gly Glu Gly Ser Lys Leu Ile Val Glu Gly Val Gln Asp Tyr Cys Thr
115 120 125

Tyr Thr Ile Lys Asp Gln Ala Asn Gly Thr Met Ser Lys Thr Lys Thr
130 135 140

Asn Val Ser Asp Trp Lys Glu Val Asn Thr Ala Phe Ser Lys Met Lys
145 150 155 160

Arg Asp Ser Leu Ser Lys Asp Leu Gln Ala Val Trp Asp Lys Val Lys
165 170 175

Asp Lys Thr Asp Thr Ser Gly Asp Leu Lys Asp Trp Cys Phe Lys Lys
180 185 190

Tyr Asp Glu Pro Phe Glu Gly Arg Asp Ser Ala Thr Tyr Lys Asp Val
195 200 205

-continued

```
Val Lys Val Cys Lys Thr Val Pro Lys Pro Ala Ala Ala Lys Pro Ala
    210                 215                 220

Ala Ala Lys Pro Val Ala Ser Lys Pro Ser Ser Asp Ser Lys Gln Val
225                 230                 235                 240

Ala Gly Thr Glu Pro Thr Ser Pro Ala Pro Thr Lys Gln Ala Gly Asp
                245                 250                 255

Ile


<210> SEQ ID NO 2
<211> LENGTH: 235
<212> TYPE: PRT
<213> ORGANISM: Mycoplasma haemofelis

<400> SEQUENCE: 2

Leu Asp Met Ser Thr Leu Leu Lys Gly Ser Leu Gly Leu Leu Gly Ala
1               5                   10                  15

Gly Ser Ala Thr Thr Ala Gly Ala Ile Tyr Leu Gly Thr Asp Ile Phe
            20                  25                  30

Lys Ser Lys Glu Asp Lys Lys Val Ser Ile Ser Lys Leu Leu Lys Thr
        35                  40                  45

Ser Asn Pro Glu Lys Arg Leu Ile Thr Ser Ser Gln Ala Ser Asp Gly
    50                  55                  60

Asp Trp Lys Glu Ala Trp Lys Asn Tyr Arg Val Ala Asn Lys Gly Lys
65                  70                  75                  80

Lys Leu Asn Glu Asp Glu Trp Lys Leu Ser Gly Trp Val Thr Pro Gln
                85                  90                  95

Asp Gly Asn Ile Thr Asn Thr Glu Asn Ala Ser Asp Ser Phe Met Asn
            100                 105                 110

Thr Cys Ser Ile Asn Lys Asp Lys Glu Val Ser Gly Thr Asp Asp Pro
        115                 120                 125

Leu Tyr Lys Ala Val Leu Val Tyr Cys Thr Arg Ser Thr Leu Val Ser
    130                 135                 140

Asp Leu Ile Ser Asp Asn Tyr Pro Asn Lys Lys Ile Leu Thr Ser Ala
145                 150                 155                 160

Asn Asn Asp Asp Ala Gly Trp Lys Glu Ala Trp Thr Gln Tyr Lys Thr
                165                 170                 175

Asp Asn Ser Gly Lys Ser Thr Gln Asn Ser Asp Ala Trp Gln Leu Ala
            180                 185                 190

Gly Trp Pro Thr Ser Thr Pro Asp Thr Val Leu Glu Ser Phe Lys Thr
        195                 200                 205

Lys Cys Gly Glu Lys Val Lys Val Ala Thr Phe Lys Thr Asp Asn Glu
    210                 215                 220

Asp Tyr Thr Asn Ala Val Lys Trp Cys Thr Lys
225                 230                 235


<210> SEQ ID NO 3
<211> LENGTH: 204
<212> TYPE: PRT
<213> ORGANISM: Mycoplasma haemofelis

<400> SEQUENCE: 3

Val Lys Ala Ala Ser Gly Leu Gly Val Ala Ala Ala Thr Val Gly Gly
1               5                   10                  15

Gly Ile Phe Val Ala Lys Gly Met Glu Gly Ser Pro Ser Thr Pro Lys
            20                  25                  30

Ser Thr Val Gln Asp Lys Leu Lys Gln Asn Gly Tyr Ser Pro Leu Asp
```

-continued

```
        35                  40                  45

Leu Glu Lys Ser Asp Gly Trp Ser Glu Val Leu Glu Ala Tyr Asn Gln
    50                  55                  60

His Lys Asn Asn Pro Ser Ile Arg Phe Asp His Gly Asp Arg Glu Ile
65                  70                  75                  80

Ser Glu Gln Glu Leu Lys Asp Ala Cys Ser Ser Ala Phe Asn Ser Asp
                85                  90                  95

Asp Lys Tyr Glu Asn Ala Lys Arg Trp Cys Val Val Pro Tyr Ser Val
            100                 105                 110

Ser Gln Val Leu Thr Ser Lys Ser Leu Lys Val Leu Asn Val Asn Asp
        115                 120                 125

Thr Gly Asp Asp Asp Gln Asp Asp Gln Asp Glu Trp Asp Asn Leu Lys
    130                 135                 140

Gly Gln Tyr Gln Glu Asn Ala Ile Pro Gly Leu Val Leu Lys Ser Thr
145                 150                 155                 160

Glu Asp Trp Gln Ser Leu Arg Thr Lys Cys Lys Glu Leu Val Glu Lys
                165                 170                 175

Lys Pro Trp Ser Asp Gly Tyr Glu Asp Ser Ile Ser His Ala Thr Arg
            180                 185                 190

Trp Cys Thr His Ala Phe Val Asn Asn Ser Asp Ser
        195                 200


<210> SEQ ID NO 4
<211> LENGTH: 209
<212> TYPE: PRT
<213> ORGANISM: Mycoplasma haemofelis

<400> SEQUENCE: 4

Met Glu Pro Leu Lys Leu Ala Phe Leu Ala Thr Gly Ala Gly Ala Thr
1               5                   10                  15

Gly Leu Gly Thr Tyr Gly Leu Tyr Ser His Leu Ser Gly Ser Gln Lys
            20                  25                  30

Glu Asn Val Gly Thr Arg Leu Val Ser Glu Ser Phe Glu Leu Leu Asn
        35                  40                  45

Asp Ser His Lys Ala Gln Trp Lys Thr Ser Leu Glu Lys Tyr Asn Gly
    50                  55                  60

Lys Lys Asp Ala Asn Ala Ser Asn Ile Asp Glu Thr Lys Leu Lys Ala
65                  70                  75                  80

Ile Cys Lys Ser Leu Ile Ser Lys Asp Lys Thr Ser Glu Ala Asp Tyr
                85                  90                  95

Lys Lys Ala Lys Leu Tyr Cys Val Val Pro Gln Gly Val Ser Glu Arg
            100                 105                 110

Leu Ser Lys Leu Gly Phe Lys Val Leu Asn Thr Ser Asp Thr Thr His
        115                 120                 125

Gln Asn Glu Trp Thr Lys Leu Ala Thr Ser Tyr Val Thr Asn Gly Lys
    130                 135                 140

Gly Asp Lys Gln Ile Glu Ser Leu Thr Leu Thr Thr Pro Ser Gly Ser
145                 150                 155                 160

Thr Asp Asn Asn Trp Ser Thr Leu Lys Glu Asn Cys Lys Thr Ile Leu
                165                 170                 175

Gly Lys Ser His Trp Glu Glu Ser Phe Asp Ser Tyr Phe Glu Lys Ser
            180                 185                 190

Lys Met Trp Cys Thr Glu Glu Ala Phe Asn Ser Leu Pro Lys Glu Lys
        195                 200                 205
```

-continued

Gln

<210> SEQ ID NO 5
<211> LENGTH: 235
<212> TYPE: PRT
<213> ORGANISM: Mycoplasma haemofelis

<400> SEQUENCE: 5

```
Met Lys Ile Val Phe Gly Asn Leu Lys Met Asn Phe Leu Tyr Lys Asp
1               5                   10                  15

Phe Gln Asp Tyr Ile Glu Asn Leu Arg Met Lys Phe Leu Gly Glu Thr
            20                  25                  30

Pro Lys Val His Leu Gly Leu Ala Ile Pro Tyr Ile Tyr Leu Lys Ser
        35                  40                  45

Ala Ser Glu Ser Ile Gly Ser Lys Ile Lys Val Leu Ala Gln Asp Leu
    50                  55                  60

His Pro Val Asp Phe Gly Ala Phe Thr Ser Ser Val Ser Ala Ala Gln
65                  70                  75                  80

Leu Ala Ser Leu Asn Val Pro Ala Thr Leu Ile Gly His Ser Glu Cys
                85                  90                  95

Arg Gln Leu Ser Gln Asn Ser Phe Val Ile Ser Asn Lys Ile Lys Ser
            100                 105                 110

Ala Leu Arg Asn Gly Leu Glu Ile Ile Tyr Cys Cys Gly Glu Asp Pro
        115                 120                 125

Glu Lys Glu Ile Ser Glu Glu Leu Phe Phe Met Thr Glu Glu Glu Ile
    130                 135                 140

Ser Lys Val Ile Ile Ala Tyr Glu Pro Ile Ser Ser Ile Gly Thr Gly
145                 150                 155                 160

Gln Ala Met Asp Pro Ser Gly Ala Asp Ser Thr Leu Leu Lys Ile Arg
                165                 170                 175

Asp Leu Ile Ala Asp Lys Tyr Gly Arg Lys Val Ala Asp Ser Met Lys
            180                 185                 190

Leu Leu Tyr Gly Gly Ser Val Asn Leu Ser Asn Tyr Lys Gly Tyr Leu
        195                 200                 205

Glu Lys Lys Asn Ile Asp Gly Val Leu Val Gly Gly Ala Ser Leu Lys
    210                 215                 220

Val Asp Asp Leu Trp Lys Met Ala Thr Leu Glu
225                 230                 235
```

<210> SEQ ID NO 6
<211> LENGTH: 494
<212> TYPE: PRT
<213> ORGANISM: Mycoplasma haemofelis

<400> SEQUENCE: 6

```
Met Asp Gly Trp Gly Leu Thr Ser Glu Ser Lys Gly Asn Ala Pro Leu
1               5                   10                  15

Leu Ala Lys Thr Pro Thr Leu Asp Phe Leu Tyr Lys Glu Tyr Pro Asn
            20                  25                  30

Ser Thr Leu Ser Ala Ser Glu Glu Ala Val Gly Leu Pro Ala Gly Gln
        35                  40                  45

Met Gly Asn Ser Glu Val Gly His Ile Asn Leu Gly Ala Gly Arg Val
    50                  55                  60

Val Tyr Thr Gly Leu Ser Leu Ile Asn Lys Cys Ile Lys Asp Gly Ala
65                  70                  75                  80

Leu Glu Ser Gln Pro Ala Val Val Glu Phe Phe Asp Leu Val Lys Ser
```

-continued

```
                85                  90                  95

Arg Gly Ser Lys Leu His Phe Leu Ser Leu Ile Ser Glu Gly Gly Val
            100                 105                 110

His Ser Asn Met Asn His Phe Leu Ala Phe Ala Asp Ile Cys Val Lys
        115                 120                 125

Arg Asn Gln Pro Tyr Ile Leu His Ala Phe Thr Asp Gly Arg Asp Val
    130                 135                 140

Ser Pro Asn Ala Ala Lys Thr Asp Phe Ile Pro Ile Val Gln Lys Leu
145                 150                 155                 160

Lys Asp Thr Asn Gly Lys Leu Gly Val Val Ser Gly Arg Tyr Tyr Ser
                165                 170                 175

Met Asp Arg Asp Lys Asn Trp Asp Arg Glu Glu Lys Val Phe Lys Tyr
            180                 185                 190

Leu Val Gly Ser Asp Lys Ser Arg Thr Phe Asp Asp Val Leu Val Tyr
        195                 200                 205

Ile Glu Gln Ser Tyr Ala Ser Gly Val Thr Asp Glu Phe Ile Glu Pro
    210                 215                 220

Ala Ile Cys Ser Ser Ser Leu Asp Ser Val Ile Gly Asp Asn Asp Val
225                 230                 235                 240

Val Val Phe Leu Asn Phe Arg Pro Asp Arg Ala Arg Gln Ile Ser His
                245                 250                 255

Met Leu Val Gly Ser Lys Gly Leu Tyr Asp Tyr Glu Pro Ser Val Lys
            260                 265                 270

Leu Asn Asn Val Ser Leu Phe Ala Leu Met Asp Tyr Glu Lys Ile Asn
        275                 280                 285

Leu Gln Asn Thr Leu Phe Pro Pro Phe Asp Ile Lys Asn Thr Leu Gly
    290                 295                 300

Glu Phe Leu Ser Asn Asn Gly Ile Ser Gln Leu Arg Ile Ala Glu Thr
305                 310                 315                 320

Glu Lys Tyr Pro His Val Thr His Phe Phe Asp Gly Gly Lys Thr Leu
                325                 330                 335

Asp Tyr Pro Lys Met Lys Lys Ile Leu Ile Pro Ser Pro Lys Val Ala
            340                 345                 350

Thr Tyr Asp Leu Gln Pro Glu Met Ser Ala Pro Lys Ile Thr Glu Ala
        355                 360                 365

Leu Leu Pro Glu Leu Lys Asn Phe Glu Val Val Ile Leu Asn Phe Ala
    370                 375                 380

Asn Pro Asp Met Val Gly His Thr Gly Ser Leu Glu Ala Thr Ile Lys
385                 390                 395                 400

Ala Cys Glu Ser Val Asp Thr Gln Ile Gly Lys Ile Tyr Glu Glu Val
                405                 410                 415

Gln Lys Leu Gly Gly Val Leu Val Val Ile Ala Asp His Gly Asn Ala
            420                 425                 430

Glu Val Met Ile Thr Ala Asp Gly Ser Pro His Thr Ala His Thr Thr
        435                 440                 445

Asn Leu Val Pro Phe Ile Val Cys Lys Lys Gly Val Thr Leu Arg Asn
    450                 455                 460

Asp Gly Val Leu Gly Asp Ile Ala Pro Thr Leu Leu Ser Leu Leu Gly
465                 470                 475                 480

Leu Lys Gln Pro Val Glu Met Thr Gly Lys Val Leu Val Ser
                485                 490
```

<210> SEQ ID NO 7

-continued

<211> LENGTH: 383
<212> TYPE: PRT
<213> ORGANISM: Mycoplasma haemofelis

<400> SEQUENCE: 7

```
Met Gly Lys Leu Val Ile Phe His Lys Glu Leu Arg Pro Asp Leu Ser
1               5                   10                  15

Phe Phe Glu Ser Phe Asn His Ile Glu Gly Val Tyr Phe Leu Ser Ser
            20                  25                  30

Asp Phe Lys Leu Tyr Arg Phe Thr Asp Ser Leu Leu Val Phe Phe Pro
        35                  40                  45

Pro Tyr Arg Val Phe Asn Asn His Lys Ile Phe Lys Ala Gly Glu Val
    50                  55                  60

Phe Val Asp Cys Ser Gln Asp Ser Lys Asp Lys Tyr Cys Ser Phe Ser
65                  70                  75                  80

Ile Ser Pro Lys Ser Leu Ser Ile Pro Asp Cys Tyr Asn Ile Ser Thr
                85                  90                  95

Asp Ser Leu Gly Glu Leu Asp Ala Leu Ile Ile Asp Phe Glu Gly Ser
            100                 105                 110

Phe Ile Lys Glu Ser Ser Leu Val Arg Tyr Ser Gln Arg Lys Leu His
        115                 120                 125

Phe Ile Arg His Thr Glu Ile Asn Val Arg Ser Tyr Phe Tyr Ile Glu
    130                 135                 140

Lys Val Lys Lys Tyr Leu Val Asp Arg Asp Leu Ala Ile Asn Val Phe
145                 150                 155                 160

Asp Ser Phe Ser Ile Ser Glu Gly Phe Lys Ser Phe Glu Arg Met Pro
                165                 170                 175

Ala Leu Arg Asn Phe Lys Ser Ser Gly Asn Ala Glu Leu Ser Lys Phe
            180                 185                 190

Asp Asp Leu Asn Leu Asp Val Phe Asp Phe Cys Glu Arg Lys Pro Asp
        195                 200                 205

Thr Ser Phe Lys Glu Glu Ser Phe Phe Asp Ser Asp Glu Lys Ile Asp
    210                 215                 220

Pro Tyr Tyr Leu Glu Gln Leu Phe Lys Asp Pro Glu Phe Phe Lys Glu
225                 230                 235                 240

Ile Glu Lys Ala Lys Leu Ser Arg Ile Glu Glu Thr His Lys Asn Asp
                245                 250                 255

Tyr Leu Ser Arg Ile Glu Lys Ala Ile Arg Arg Ser Arg Ala Leu Ser
            260                 265                 270

Ile Ser Val Pro Glu Tyr Asn Tyr Pro Thr Ala Pro Phe Asp Ser Phe
        275                 280                 285

Pro Glu Asn Leu Asn Tyr Leu Arg Glu Ile Glu Asn Phe Asn Glu Gln
    290                 295                 300

Glu Glu Ser Ala Phe Lys His Ile Asp Leu Tyr Thr Ser Tyr Val Ser
305                 310                 315                 320

Pro Met Pro Leu Gly Arg Gly Val Phe Ile Phe Arg Asp Leu Glu Glu
                325                 330                 335

Leu Phe Asp Pro Tyr Lys Gly Thr Ile Asn Ile Pro Asp Ile Glu Asp
            340                 345                 350

Glu Ile Glu Ile Met Asn Ala Tyr Ile Asp Glu Ala Leu Asp Phe Tyr
        355                 360                 365

Phe Lys Lys Glu Ile Ser Glu Pro Pro Tyr Phe Ser Trp Glu Glu
    370                 375                 380
```

<210> SEQ ID NO 8
<211> LENGTH: 53
<212> TYPE: PRT
<213> ORGANISM: Mycoplasma haemofelis

<400> SEQUENCE: 8

```
Leu Leu Val Leu His Lys Leu Phe Phe Ser Gly Glu Val Arg Arg Phe
1               5                   10                  15

Arg Asn Leu Leu Leu Glu Ile Glu Val Gln Gly Phe Ile Asn Ile Cys
            20                  25                  30

Ile His Asn Leu Tyr Leu Ile Leu Tyr Ile Arg Asn Ile Tyr Gly Ser
        35                  40                  45

Phe Ile Trp Ile Lys
    50
```

<210> SEQ ID NO 9
<211> LENGTH: 38
<212> TYPE: PRT
<213> ORGANISM: Mycoplasma haemofelis

<400> SEQUENCE: 9

```
Val Gly Gly Thr Lys Thr Ser Ser Ser Ser Ala Thr Gly Ser Ser Cys
1               5                   10                  15

Ser Ser Asn Asp Ser Ser Trp Thr Ile Ser Cys Ser Ser Ser Ile Asn
            20                  25                  30

Tyr Ser Ser Gln Glu Lys
        35
```

<210> SEQ ID NO 10
<211> LENGTH: 259
<212> TYPE: PRT
<213> ORGANISM: Mycoplasma haemofelis

<400> SEQUENCE: 10

```
Met Glu Asp Glu Gln Glu Ile Val Gln Glu Glu Ser Leu Glu Glu Gln
1               5                   10                  15

Glu Glu Pro Val Ala Glu Glu Glu Glu Val Phe Val Pro Pro Thr Leu
            20                  25                  30

Glu Glu Val Tyr Asp Lys Ser Leu Phe Asp Asn Phe Ser Asn Leu Phe
        35                  40                  45

Tyr Val Arg Thr Ala Pro Pro Ser His Phe Asn Trp Phe Leu Ser Pro
    50                  55                  60

Phe Val Val His Val Phe Glu Phe Leu Thr Ser Leu Arg Arg Asp Arg
65                  70                  75                  80

Ala Met Val Phe Ser His Glu Glu Asn Phe Asp Ser Gln Pro Ile Arg
                85                  90                  95

Asp Lys Tyr Leu Lys Asp Leu Ser Phe Leu Lys Ser Ile Glu Lys Tyr
            100                 105                 110

Thr His Phe Pro Arg Phe Asp Tyr Phe Ile Ser Pro Phe Ser Tyr Glu
        115                 120                 125

Tyr Glu Lys Met Phe Trp Thr Phe Thr Pro Tyr Lys Lys Thr Met Phe
    130                 135                 140

Thr Ile Gln Asp Ser Leu Phe Phe Leu Asn Ser Glu Pro Phe Gly Pro
145                 150                 155                 160

Gln Gly Arg Cys Met Phe Trp Glu Ser His Ala Leu Asn His Pro Glu
                165                 170                 175

Glu Cys Gln Ala Tyr Ile Arg Arg Ile Glu Ile Glu Val Lys Asn Lys
            180                 185                 190
```

```
Tyr Ser Ala Leu Asn Arg Ala Tyr Glu Val Phe Asn Arg Asp Leu Tyr
        195                 200                 205

Gly Glu Tyr Glu Asp Asp Phe Ser Met Leu Asp Cys Pro Asp Ile Asn
    210                 215                 220

Leu Gly Lys Phe Asp Lys Lys Ala Arg Lys Glu Ala Ser Lys Lys Val
225                 230                 235                 240

Trp Tyr Glu Ser Glu Pro Pro Glu Ala Glu Ile Glu Arg His Gln Glu
                245                 250                 255

Pro Lys Lys


<210> SEQ ID NO 11
<211> LENGTH: 199
<212> TYPE: PRT
<213> ORGANISM: Mycoplasma haemofelis

<400> SEQUENCE: 11

Val Ser Phe Lys Ser Phe Ile Ser Glu Asp Glu Asn Val Arg Tyr Phe
1               5                   10                  15

Arg Leu Gly Asp Val Cys Lys Ile Tyr Ala Gly Ile Ser Phe Lys Ser
            20                  25                  30

Ser Phe Tyr Arg Asp Arg Gly Phe Pro Ile Ile Lys Thr Arg Asn Ile
        35                  40                  45

Gln Asp Asn Gln Ile Val Thr Gly Asp Leu Asn Tyr Cys Asp Leu Ala
    50                  55                  60

Asn His Lys Asp Ala Met Ile Ile Lys His Gly Asp Val Val Met Ala
65                  70                  75                  80

Lys Asp Gly Ser Cys Cys Gly Lys Ile Gly Ile Asn Leu Thr Asp Glu
                85                  90                  95

Glu Phe Leu Phe Asp Ser His Val Leu Gln Phe Ile Pro Asn Glu Lys
            100                 105                 110

Leu Leu Ile Lys Arg Tyr Leu Tyr His Phe Leu Leu Ser Cys Gln Asp
        115                 120                 125

Lys Ile Arg Glu Leu Ala Val Gly Ser Ala Ile Pro Gly Ile Arg Lys
    130                 135                 140

Ser Glu Leu Glu Lys Ile Lys Ile Pro Val Ser Ser Leu Glu Val Gln
145                 150                 155                 160

Glu Lys Val Ala Ser Thr Leu Asp Lys Phe Arg Glu Ile Glu Arg Glu
                165                 170                 175

Ile Ser Leu Arg Asp Lys Gln Tyr Glu Tyr Tyr Arg Asn Tyr Leu Ile
            180                 185                 190

Met Gly Ser His Asp Ser His
        195


<210> SEQ ID NO 12
<211> LENGTH: 52
<212> TYPE: PRT
<213> ORGANISM: Mycoplasma haemofelis

<400> SEQUENCE: 12

Leu Ser Ile Gln Ala Asp Ile Ala Ser Lys Leu Gly Lys Phe Gln Glu
1               5                   10                  15

Leu Lys Glu Glu Leu Lys Glu Glu Leu Leu Leu Arg Lys Lys Lys His
            20                  25                  30

Asn Tyr Tyr Arg Arg Gln Ile Trp Lys Thr His Leu Asn Gly Val Gln
        35                  40                  45
```

```
Gly Leu Lys Leu
    50


<210> SEQ ID NO 13
<211> LENGTH: 144
<212> TYPE: PRT
<213> ORGANISM: Mycoplasma haemofelis

<400> SEQUENCE: 13

Val Phe Lys Gly Phe Leu Lys Ala Glu Val Arg Glu Phe Leu Leu Glu
1               5                   10                  15

Asp Val Cys Asn Ile Gln Asn Gly Tyr Ser Phe Ser Ser Ser Lys Tyr
            20                  25                  30

Arg Ser Thr Gly His Pro Ile Ile Arg Ile Gly Asn Ile Gln Gly Thr
        35                  40                  45

Gln Phe Lys Val Glu Asp Leu Val Tyr Phe Glu Arg Asp Asp Tyr Lys
    50                  55                  60

Glu Asp Leu Ser Arg Phe Ile Ile Lys Pro Gln Asp Leu Val Ile Thr
65                  70                  75                  80

Ala Arg Gly Ser Cys Gly Lys Val Ala Leu Asn Lys Thr Asp Ser Ser
                85                  90                  95

Phe Tyr Leu Asn Gln Gly Val Trp Arg Leu Asp Pro Asn Pro Leu Phe
            100                 105                 110

Leu Asn Arg Glu Tyr Leu Phe Tyr Phe Leu Ser Asn Ser Asp Leu Ser
        115                 120                 125

Ser Met Val Ile Lys Gly His Ile Pro Arg Leu Asn Val Asn Ser Ile
    130                 135                 140


<210> SEQ ID NO 14
<211> LENGTH: 198
<212> TYPE: PRT
<213> ORGANISM: Mycoplasma haemofelis

<400> SEQUENCE: 14

Val Ser Phe Lys Ser Phe Leu Ser Glu Ser Lys Asp Val Lys His Leu
1               5                   10                  15

Lys Leu Lys Asp Val Cys Lys Ile Ile Ala Gly Lys Arg Phe Thr Pro
            20                  25                  30

Tyr Thr Ser Glu Gly Met Pro Val Leu Arg Ser Gly Asn Ile Ile Asp
        35                  40                  45

Gly Tyr Val Val Asp Glu Asp Phe Val Tyr Cys Asp Arg Glu Lys His
    50                  55                  60

Pro Arg Val Asp Thr Val Lys Tyr Gly Asp Ile Leu Ile Val Arg Phe
65                  70                  75                  80

Gly Ser Ala Gly Val Val Gly Met Asn Leu Ile Asn Arg Glu Phe Phe
                85                  90                  95

Leu Asp Ala Asn Leu Ser Lys Phe Ser Pro Asp Ser Lys Ile Leu His
            100                 105                 110

Lys Gln Tyr Leu Tyr His Phe Leu Leu Ser Arg Gln Glu Glu Ile Lys
        115                 120                 125

Gly Trp Ala Arg Gly Ala Val Ile Pro Ala Ile Arg Lys Ser Asp Leu
    130                 135                 140

Glu Glu Leu Met Ile Pro Val Pro Ser Leu Glu Gln Gln Gln Thr Ile
145                 150                 155                 160

Ala Ser Lys Leu Asp Lys Leu Val Glu Leu Lys Arg Glu Leu Ile Leu
                165                 170                 175
```

```
Arg Lys Glu Gln His Ser Tyr Tyr Arg Lys Gln Ile Trp Glu Ala Cys
            180                 185                 190

Ser Asn Gly Cys Ser Lys
        195
```

<210> SEQ ID NO 15
<211> LENGTH: 180
<212> TYPE: PRT
<213> ORGANISM: Mycoplasma haemofelis

<400> SEQUENCE: 15

```
Met Ser Leu Leu Thr Lys Ser Ala Leu Gly Phe Ala Ala Ala Gly Thr
1               5                   10                  15

Thr Ala Ala Gly Ala Ala Tyr Ala Gly Gly Leu Phe Asp Gly Lys Glu
            20                  25                  30

Lys Glu Lys Thr Ser Ile Ser Lys Leu Leu Gln Ser Leu Asn Pro Glu
        35                  40                  45

Lys Arg Leu Ile Met Ala Ser Glu Gly Ser Asp Pro Leu Trp Lys Glu
    50                  55                  60

Ala Trp Lys Asn Tyr Lys Val Lys Tyr Ser Gly Lys Gly Leu Asp Pro
65                  70                  75                  80

Leu Lys Val Leu Ser Gly Lys Ala Leu Ala Ser Asp Glu Ser Ala Pro
                85                  90                  95

Ala Asp Phe Met Ser Ser Cys Lys Asp Leu Phe Asp Val Lys Val Val
            100                 105                 110

Asp Gly Lys Asp Asp Ser Tyr Gln Leu Val Leu Asn His Cys Thr Arg
        115                 120                 125

Leu Thr Leu Val Ser Asp Trp Ile Ala Asp Arg Gly His Glu Leu Val
    130                 135                 140

Ser Gln Thr Glu Gly Asp Ala Thr Ile Trp Lys Asp Leu Trp Lys Lys
145                 150                 155                 160

Tyr Lys Asp Ala Gly Lys Asn Ala Trp Ser Val Ser Glu Tyr Ser Ser
                165                 170                 175

Tyr Gln Asp Gly
            180
```

<210> SEQ ID NO 16
<211> LENGTH: 226
<212> TYPE: PRT
<213> ORGANISM: Mycoplasma haemofelis

<400> SEQUENCE: 16

```
Met Thr Pro Leu Thr Lys Ala Ala Ser Ala Thr Ala Ile Ala Gly Thr
1               5                   10                  15

Ala Ala Thr Gly Gly Ile Tyr Leu Gly Thr Asp Leu Phe Lys Asp Lys
            20                  25                  30

Lys Val Glu Ile Ala Ser Leu Leu Lys Thr Ala Tyr Pro Asn Lys Arg
        35                  40                  45

Leu Ile Thr Ser Lys Thr Val Ser Asp Asp Ala Trp Lys Lys Ala Tyr
    50                  55                  60

Lys Ala Tyr Arg Glu Ala Asn Lys Asp Lys Thr Lys Asp Ile Trp Ser
65                  70                  75                  80

Leu Lys Asp Trp Thr Lys Pro Gln Ala Thr Val Glu Glu Thr Asn Ala
                85                  90                  95

Thr Asp Asp Phe Ile Ser Lys Cys Asn Ser Asn Ser Lys Leu Ser Val
            100                 105                 110
```

```
Val Gly Lys Asp Asp Pro Leu Tyr Lys Gln Val Leu Ala Tyr Cys Thr
        115                 120                 125

Arg Asp Thr Leu Val Ser Asp Leu Ile Ser Glu Tyr Gly Lys Gly Lys
    130                 135                 140

Lys Leu Leu Ser Lys Asp Gly Ser Asp Gln Asp Ala Ala Trp Lys Ala
145                 150                 155                 160

Ala Trp Asn Val Tyr Lys Thr Arg Asn Lys Asp Lys Gly Glu Asn Leu
                165                 170                 175

Asp Pro Trp Lys Leu Asn Asn Trp Asn Thr Lys Lys Ser Gly Asp Glu
            180                 185                 190

Leu Pro Asp Asn Tyr Lys Asp Lys Cys Val Glu Tyr Ser Lys Lys Ala
        195                 200                 205

Ala Tyr Gln Leu Glu Asp Glu Asn Tyr Lys Asn Val Leu Asp Trp Cys
    210                 215                 220

Thr Ala
225


<210> SEQ ID NO 17
<211> LENGTH: 232
<212> TYPE: PRT
<213> ORGANISM: Mycoplasma haemofelis

<400> SEQUENCE: 17

Met Thr Ser Leu Ser Lys Ala Ala Leu Gly Phe Ser Ala Ala Gly Thr
1               5                   10                  15

Thr Ala Ala Gly Ala Leu Tyr Met Gly Gly Ala Phe Lys Gly Glu Glu
            20                  25                  30

Glu Lys Pro Val Lys Thr Ala Ile Ser Lys Leu Leu Lys Glu Leu Asn
        35                  40                  45

Pro Lys Lys Arg Leu Ile Glu Ser Ser Val Gln Ala Ser Asp Ala Ile
    50                  55                  60

Trp Lys Ala Ala Trp Lys Ala Tyr Arg Thr Lys Asn Lys Asp Ser Lys
65                  70                  75                  80

Val Gly Glu Asp Thr Trp Lys Leu Lys Gly Trp Thr Thr Arg Ser Asn
                85                  90                  95

Glu Ala Gln Ile Thr Glu Glu Glu Ala Pro Pro His Phe Ile Gln Ala
            100                 105                 110

Cys Ser Asp Asn Gly Lys Glu Glu Val Ile Gly Ile Asn Asp Asp Leu
        115                 120                 125

Tyr Lys Glu Val Leu Glu Phe Cys Thr Arg Asp Val Ser Ile Lys Asp
    130                 135                 140

Trp Ile Ser Asp Ala Gly Arg Ser Ala Ile Gly Lys Glu Asp Thr Glu
145                 150                 155                 160

Gly Trp Lys Lys Thr Trp Lys Leu Tyr Arg Ala Lys Asn Lys Asp Ile
                165                 170                 175

Ala Ala Gly Gln Asp Thr Trp Lys Val Ser Ser Trp Asp Pro Lys Thr
            180                 185                 190

Thr Ser Asp Asp Asn Val Val Glu Asp Phe Lys Thr Lys Cys Thr Ser
        195                 200                 205

Lys Leu Asp Leu Lys Ser Ser Asp Ser Ser Phe Asp Glu Glu Tyr Pro
    210                 215                 220

Arg Val Leu Glu Trp Cys Thr Lys
225                 230


<210> SEQ ID NO 18
```

<211> LENGTH: 230
<212> TYPE: PRT
<213> ORGANISM: Mycoplasma haemofelis

<400> SEQUENCE: 18

Leu Arg Asp Ser Trp Gly Asp Met Thr Ala Leu Thr Lys Ala Ala Ser
1 5 10 15

Ala Thr Ala Val Ala Gly Thr Ala Ala Gly Gly Gly Ile Tyr Phe Gly
20 25 30

Thr Asp Leu Leu Lys Ser Lys Lys Val Asp Ile Ser Ser Leu Met Lys
35 40 45

Glu Val Asp Pro Gln Lys Arg Phe Ile Thr Ala Thr Ser Thr Gly Asp
50 55 60

Asp Ser Trp Lys Ala Ala Tyr Lys Ser Tyr Arg Glu Ser Gly Lys Asp
65 70 75 80

Val Trp Gly Leu Gly Val Lys Thr Ala Ser Pro Glu Thr Leu Ile Asp
85 90 95

Ala Thr Thr Glu Phe Leu Ala Lys Cys Lys Ser Asn Gly Lys Val Lys
100 105 110

Val Ser Gly Lys Asp Asp Pro Leu Tyr Lys Gln Val Leu Ala Tyr Cys
115 120 125

Thr Arg Asp Thr Thr Val Arg Asp Leu Ile Glu Glu Gly Lys Thr Gly
130 135 140

Arg Lys Leu Leu Asp Ser Ser Asp Thr Gly Asn Asp Lys Glu Ser Gly
145 150 155 160

Trp Glu Asp Ala Trp Thr Ala Tyr Arg Thr Lys Asn His Val Glu Gly
165 170 175

Gly Thr Ser Gln Asn Thr Trp Glu Val Glu Gly Trp Asp Asn Lys Lys
180 185 190

Thr Gly Asn Thr Leu Pro Thr Asp Tyr Lys Thr Lys Cys Ala Glu Lys
195 200 205

Ala Lys Gln Pro Ala Tyr Arg Leu Glu Asp Glu Asn Tyr Lys Asn Val
210 215 220

Leu Ala Trp Cys Thr Lys
225 230

<210> SEQ ID NO 19
<211> LENGTH: 947
<212> TYPE: PRT
<213> ORGANISM: Mycoplasma haemofelis

<400> SEQUENCE: 19

Met Ile Asn Lys Gly Ile Ala Phe Thr Thr Ile Phe Leu Ser Gly Ser
1 5 10 15

Leu Tyr Ser Phe Gly Ser Phe Ile His Asp Trp Gln Asp Tyr Gln Phe
20 25 30

Gln Gln Val Glu Gly Ser Gly Ile Leu Gln Asp Lys Arg Arg Gly Ser
35 40 45

Phe Leu Arg Gly Glu Leu Pro Phe Thr Pro Ser Phe Arg Asp Arg Leu
50 55 60

Ala Pro Ser His Ile Gln Lys Thr Ser Phe Gln Gln His Lys His Leu
65 70 75 80

Phe Ala Pro Glu Met Gln Lys Tyr Leu Thr Glu Val Asn Glu Glu Asp
85 90 95

Ile Lys Glu Gly His Tyr Ser Ser Lys Lys Lys Glu Leu Leu Asp Leu
100 105 110

```
Ile His Tyr Lys Lys Glu Trp Ile Leu Thr Ser Asp Lys Glu Ile Ser
        115                 120                 125

Tyr Lys Ser Gly Tyr Phe Gln Glu Lys Leu Asn Asn Phe Gly Asp Asn
    130                 135                 140

Lys Leu Val Gln Asp Ile Leu Trp Ser Leu Val Glu Glu Ser Gln Val
145                 150                 155                 160

Asn Ala Thr Leu Ile Arg Pro Glu Ser Ile Thr Ile Asn Phe Lys Arg
                165                 170                 175

Glu Lys Val Gly Tyr Gln Lys Asn Pro Leu Leu Asp Lys Ser Asp Val
            180                 185                 190

Ile Lys Asn Leu His Ile Lys Phe Arg Ile Phe Asn Pro Asn Arg Gln
        195                 200                 205

Lys Thr Phe Val Phe Lys Ser Ile Glu Ile Asp Pro Thr Ser Glu Thr
    210                 215                 220

Asp Val Glu Ile Thr Leu Arg Glu Gly Glu Leu Lys Pro Val Ser Thr
225                 230                 235                 240

Ala Leu Ala Ala Leu Ala Ala His Lys Leu Ser Ala Ser Ser Trp Ser
                245                 250                 255

Ile Phe Pro Ile Glu Glu Gly Phe Lys Val Thr Lys Glu Val Val Tyr
            260                 265                 270

Pro Asn Lys Val Lys Thr Gln Glu His Lys Asp Ser Leu Phe Leu Leu
        275                 280                 285

Tyr Asn Ser Ser Arg Phe Phe Glu Lys Trp Val Gly Asn Pro Arg Ser
    290                 295                 300

Arg Ser Val Ser Thr His Thr His Ser Leu Val Asp Tyr Glu Tyr Val
305                 310                 315                 320

Arg Lys Ser Leu Ser Ala Lys Leu Val Asn Ile Thr Thr Asp Gln Val
                325                 330                 335

Lys Lys Asp Ile Glu Arg Trp Tyr Gly Ser Phe Thr Ala Phe Ile Leu
            340                 345                 350

Arg Thr Lys Ile Glu Asp Met Ile Asn Leu Ile Asn Leu Leu Gln Lys
        355                 360                 365

Asn Thr Phe Phe Asp Lys Arg Gly Asn Lys Val Ser Val Val Asp Asn
    370                 375                 380

Ala Ile Asn Asp Phe Thr Phe Arg His Asn Leu Tyr Asn His Phe Gln
385                 390                 395                 400

Phe Asp Ser Asn Leu Arg Lys Val Leu Asp Thr Leu Phe Leu Gln Asn
                405                 410                 415

Lys Asn Lys Pro Glu Leu Lys Ile Thr Val Lys Glu Ala Lys Ala Leu
            420                 425                 430

Leu Asn Ser Trp Val Tyr Gln Leu Glu Gln Ile Lys Asp Ser Ile Arg
        435                 440                 445

Ile Glu Leu Lys Trp Glu Lys Glu Pro Gln Lys Thr Asn Ala Asp Leu
    450                 455                 460

Gly Tyr Glu Asn Ile Tyr Pro Ala Phe Ser Tyr Lys Phe Thr Gln Lys
465                 470                 475                 480

Phe Val Phe Thr Lys Glu Val Lys Ile Pro Leu Lys Gly Thr Tyr Asn
                485                 490                 495

Thr Thr Glu Asn Lys Phe Glu Glu Ala Thr Thr Glu Thr Glu Asn Lys
            500                 505                 510

His Lys Phe Asp Leu Ser Asn Arg Leu Lys Asn Val Lys Val Phe Leu
        515                 520                 525
```

-continued

```
Thr Pro Ile Ser Phe Leu Phe Asn Ser Met Asn Gly Gly Ser Ile Gly
    530                 535                 540

Gly Val Ser Ile Met Asp Val Leu Ile Pro Asp Val Ala Asn Phe Val
545                 550                 555                 560

Asp Leu Glu Ser Leu Thr Ile Asp Ala Asn Gln Glu Ile Lys Asn Thr
                565                 570                 575

Tyr Glu Ser Lys Asn Ser Pro Ile Thr Leu Ala Ile Gly Gly Glu Glu
            580                 585                 590

Asp Met Gln Lys Ile His Phe Pro Gly Thr Asn Ile Gly Trp Lys Ser
        595                 600                 605

Leu Asp Val Thr His Ser Gln Asp Leu Ser Lys Phe Thr Lys Leu Phe
    610                 615                 620

Tyr Lys Leu Tyr Glu Lys Phe Asp Thr Tyr Lys Asp Lys Ser Asn Gln
625                 630                 635                 640

Ala Leu Gly Ala Leu Gln Leu Leu Lys Glu Asn Ser Arg Leu Lys Ala
                645                 650                 655

Asp Pro Ile Ser Phe Ile Ala His Ala Ile Asn Ser Leu Phe Asp Lys
            660                 665                 670

Asn Tyr Leu Gln Ser Lys Val Ser Glu Glu Ser Lys Arg Pro Trp Pro
        675                 680                 685

Val Phe Phe Asn Ser Leu Leu Gly Lys Pro Leu Asp Phe Lys Ser Arg
    690                 695                 700

Gln Leu Leu Thr Gly Leu Ser Ser Leu Phe Phe Glu Trp Asp Lys Glu
705                 710                 715                 720

Trp Asp Ser Lys Ser Glu Glu Asp Lys Cys Asp Gly Gln Gly Gln Gly
                725                 730                 735

Gln Gly Gln Glu Lys Tyr Tyr Cys Thr Lys Phe Ser Leu Lys Asn Ser
            740                 745                 750

Arg Lys Lys Gln Ile Leu Pro Asn Ser Glu Glu Thr Lys Asn Val Thr
        755                 760                 765

Gln Lys Phe Phe Pro Thr Tyr Ser Ser Tyr Phe Pro Glu Lys Pro Val
    770                 775                 780

Val Phe Gly Thr Thr Asp Asp Thr Thr Ala Tyr Asp Ala Phe Leu Ala
785                 790                 795                 800

Lys Glu Gly Lys Ser Ser Ile Gly Leu Val Asn Asn Tyr Thr Lys Leu
                805                 810                 815

Lys Glu Val Phe Lys Ser Arg Phe Glu Lys Asp Pro Asn Phe Phe Pro
            820                 825                 830

Ser Asn Lys Glu Ile Asn Trp Asn Asn Ala Lys Val Ser Tyr Val Arg
        835                 840                 845

Leu Asp Leu Glu Lys Ala Ile Lys Ser Val Leu Ala Leu Glu Asn Thr
    850                 855                 860

Ala Tyr Gly Gly Leu Gly Leu Met Val Ser Ala Val Gly Ile Glu Phe
865                 870                 875                 880

His Lys Ile Leu Gly Glu Ala Leu Val Arg Asp Gly Phe Trp Ile Asn
                885                 890                 895

Met Asn Leu Met Asp Glu Lys Gly Ser Phe Trp Thr Ile Glu His Pro
            900                 905                 910

Ile Lys His Met Phe Tyr Ser Pro Phe Ser Glu Ser Trp Leu Phe Val
        915                 920                 925

Lys Pro Asp Leu Asp His Thr Lys Leu Glu Leu Gly Thr Phe Ser Thr
    930                 935                 940

Lys Arg Lys
```

945

<210> SEQ ID NO 20
<211> LENGTH: 912
<212> TYPE: PRT
<213> ORGANISM: Mycoplasma haemofelis

<400> SEQUENCE: 20

Val Phe Phe Ile Leu Pro Ser Arg Arg Lys Leu Ala Ile Gly Ala Gly
1               5                   10                  15

Gly Ile Phe Phe Ala Ser Gly Phe Ile Tyr Phe Arg Val Ala Glu Lys
            20                  25                  30

Glu Pro Phe Glu Lys Ile Glu Gly Ser Leu Pro Leu Arg Asn Lys Asn
        35                  40                  45

Lys Leu Asn Phe Gln Asp Lys Gln Leu Ser Leu Gln Gly Phe Leu Lys
    50                  55                  60

Gln Asp His Leu Tyr Ser Gln Asn Tyr Gln Val Phe Asp Pro Ser Ile
65                  70                  75                  80

Arg Lys Tyr Leu Glu Ile Pro Ile Ser Pro Arg Arg Val Glu Glu Ser
                85                  90                  95

Gly Asn Leu Phe Lys Ala Phe Asn Ser Leu Lys Gly Trp Asn Arg Thr
            100                 105                 110

Ala Ser Thr Ile Ser Asp Arg Asp Leu Ser Tyr Arg Asp Asn Pro Phe
        115                 120                 125

Ile Gly Gly Val Asn Ser Leu Lys Lys Glu Glu Ile Ile Arg Asp Ile
    130                 135                 140

Leu Glu Ser Ile Leu Asp Glu Ser Glu Tyr Leu Ser Thr Leu Ile Arg
145                 150                 155                 160

Ala Asp Ser Ile Lys Ile Glu Phe Lys Lys Glu Glu Gly Phe Ser Leu
                165                 170                 175

Val Lys Asp Phe Asn Leu Arg Leu Arg Ile Leu Asn Pro Arg Lys Arg
            180                 185                 190

Lys Ala Tyr Leu Phe Lys Ser Ile Glu Ile Asp Pro Leu Ser Glu Asn
        195                 200                 205

Asp Ile His Ile Ser Leu Ser Gln Ser Glu Ile Lys Pro Thr Thr Val
    210                 215                 220

Ser Val Asn Leu Gly His Ser Lys Gln Ile Ser Trp Ser Leu Phe Pro
225                 230                 235                 240

Lys Asp Ser Ala Trp Lys Ile Thr Lys Ile Thr His Ser Pro Asn His
                245                 250                 255

Arg Lys Thr Glu Glu Thr Lys Phe Ser Leu Pro Leu Ile Tyr Gly Thr
            260                 265                 270

Ser Ala Ala Leu Lys Asp Leu Gln Glu Leu Leu Pro Arg Lys Glu Val
        275                 280                 285

Asp His Pro Phe Pro Ile Ala Ser Ser Leu Asp Tyr Gly Tyr Val Arg
    290                 295                 300

Glu Lys Leu Thr Pro Leu Leu Val Asn Ile Ser Glu Asn Gln Met Glu
305                 310                 315                 320

Lys Asp Ile Glu Ala Trp Phe Gly Ala His Lys Ala His Gln Ile Arg
                325                 330                 335

Val Tyr Ile Ser Asp Leu Gln Asn Leu Ile Glu Met Phe Lys Lys Arg
            340                 345                 350

Ser Phe Leu Asp Lys Asn Gly Arg Lys Ala Ser Leu Ile Glu Met Val
        355                 360                 365

-continued

```
Met Lys Ser His Thr Phe Lys Asp Gly Leu Tyr Asn His Met Lys Leu
    370                 375                 380

Ser Ser Ser Tyr Arg Lys Val Leu Asp Ser Leu Leu Thr Ser Glu Gly
385                 390                 395                 400

Lys Glu Leu Lys Leu Thr Glu Glu Glu Cys Tyr Ala Leu Leu Asp Ser
                405                 410                 415

Trp Ser Tyr Gln Leu Lys Gln Met Gln Asp Ser Ile Lys Ile Ser Ile
            420                 425                 430

Thr Trp Asp Glu Lys Pro Lys Arg Val Ile Gln Pro Leu Gly Tyr Thr
        435                 440                 445

Ser Pro Tyr Pro Ala Val Ser Phe Lys Phe Lys Gln Lys Ile Ser Phe
    450                 455                 460

Glu Lys Ala Val Lys Ile Pro Leu Asn Gly Ser Trp Asp Ser Ser Gln
465                 470                 475                 480

Lys Lys Tyr Asp Ala Ser Ser Gly Asp Gln Lys Phe Asp Ile Thr Lys
                485                 490                 495

Arg Leu Ser Ser Leu Gly Thr Ile Leu Ala Pro Ile Arg Ser Val Phe
            500                 505                 510

Lys Glu Met Gly Asn Gly Gly Ser Phe Met Gly Ala Asp Ile Phe Asp
        515                 520                 525

Val Leu Met Pro Asp Val Ser Gln Phe Leu Gly Ile Asp Gly Leu Glu
    530                 535                 540

Ile Asp Ala Asn Glu Tyr Ile Glu Asn Ile Tyr Glu Ala Ser Asn Ser
545                 550                 555                 560

Pro Ile Gly Ile Ala Ile Gly Asp Ser Glu Asp Tyr Gln Gly Ile Asn
                565                 570                 575

Ile Lys Gly Lys Asn Ile Gly Trp Lys Ala Leu Asp Val Ser Ser Ser
            580                 585                 590

Ile Asn Leu Ala Asn Phe Ser Lys Phe Phe Tyr Lys Leu Tyr Glu Lys
        595                 600                 605

Ile Asp Thr Tyr Lys Asp Pro Ser Asn Ser Ala Leu Gly Val Ser Gln
    610                 615                 620

Leu Trp Asn Phe Thr Thr Leu Leu Gln Gln Arg Pro Ile Ser Phe Ile
625                 630                 635                 640

Ile His Ala Ile His Ser Thr Phe Asp His Gln Tyr Leu Lys Ser Gly
                645                 650                 655

Asn Ser Thr Ser Glu Asp Lys Arg Pro Trp Pro Val Phe Phe Lys Ser
            660                 665                 670

Leu Phe Gln Asp Pro Ile Thr Leu Lys His Lys Gln Val Phe Val Gly
        675                 680                 685

Tyr Ser Gly Ala Phe Phe Asp Val Lys Glu Trp Phe Arg Ser Glu Thr
    690                 695                 700

Lys Ser Ser Glu Gln Tyr Ser Thr Ser Trp Asp Ile Ser Thr Lys Lys
705                 710                 715                 720

Gln Arg Asp Glu Trp Glu Ile Leu Ser Pro Lys Asn Glu Asp Val Ala
                725                 730                 735

Leu Ile Asn Gln Lys Phe Ala Leu Asn Tyr Ser Ser Phe Ser Pro Glu
            740                 745                 750

Gln Pro Ile Ile Ile Asn Ser Glu Glu Asn Lys Ser Gln Tyr Asp Ala
        755                 760                 765

Phe Leu Ala Lys Glu Gly Ser Thr Ser Ile Gly Leu Val Asn His Tyr
    770                 775                 780

Asp Arg Leu Lys Ser Val Phe Arg Asp Asn Asn Lys Ser Asn Ile Tyr
```

```
785                 790                 795                 800

Tyr Pro Asn Ile Asp Trp Glu Asn Met Lys Val Ser Tyr Ala Gln Leu
                805                 810                 815

Asn Leu Glu Lys Ala Ile Lys Ser Val Leu Ala Ile Arg His Thr Phe
            820                 825                 830

Gln Gly Phe Ser Ser Leu Thr Leu Thr Ala Leu Gly Ile Glu Ile His
        835                 840                 845

Lys Ile Leu Gly Glu Ala Leu Ile Arg Asn Pro Phe Trp Ile Asn Met
    850                 855                 860

Asn Phe Met Lys Glu Ile Gly Ser Trp Ser Lys Asn Glu Ile Pro Phe
865                 870                 875                 880

Lys Tyr Met Ser Tyr Ser Val Tyr Ser Glu Glu Ser Leu Tyr Ile Thr
                885                 890                 895

Pro Gln Leu Asp Lys Thr Lys Leu Asn Leu Gly Arg Phe Ile Lys Leu
            900                 905                 910


<210> SEQ ID NO 21
<211> LENGTH: 374
<212> TYPE: PRT
<213> ORGANISM: Mycoplasma haemofelis

<400> SEQUENCE: 21

Met Asp Gly Gln Glu Lys Gly Lys Lys Asp Ile Ala Asn Asp Pro Glu
1               5                   10                  15

Val Arg Lys Glu Leu Glu Ala Tyr Glu Lys Tyr Ile Leu Gln Gln Lys
            20                  25                  30

His Glu Ile Phe Asn Arg Ile Ile Leu Asn Ala Ile His Thr Leu Lys
        35                  40                  45

Ile Gln Gln Pro Ile Ile Ser Cys Cys Lys Arg Ile Asp Leu Ser Ser
    50                  55                  60

Leu Pro Gly Phe Asn Glu Glu Thr Ile Gly Gln Leu Leu Gly Lys Asp
65                  70                  75                  80

Gly Gln His Lys Gln His Phe Ile Asn Leu Thr Lys Val Asp Leu Gln
                85                  90                  95

Val Asp Gln Lys Cys Pro Asn His Gly Ile Val Leu Ser Lys Tyr Asn
            100                 105                 110

Ser Val Asn Val Glu Lys Ala Val Glu Leu Val Lys Lys Leu Leu Glu
        115                 120                 125

Leu Lys Ser Trp Asn Leu Glu Lys Met Lys Ser Leu Tyr Glu Lys Val
    130                 135                 140

Asn Lys Glu Phe Glu Asp Lys Cys Asn Lys Ile Gly Gly Gln Trp Leu
145                 150                 155                 160

Glu Gln Phe Leu Gly Tyr Glu Asn Tyr Pro Asp Phe Leu Ala Thr His
                165                 170                 175

Val Gly Thr Leu Gln Phe Val Tyr Ser Phe Ser Gln Asn Ile Leu Glu
            180                 185                 190

His Ser Ile Glu Val Ala Gln Leu Ser Ala Asn Ile Ala Phe Gln Leu
        195                 200                 205

Gly Leu Asp Pro Leu Lys Ala Lys Arg Ala Gly Phe Phe His Asp Ile
    210                 215                 220

Gly Lys Ala Lys Ala Asn Leu Gly Asp His Val Asp Glu Gly Leu Lys
225                 230                 235                 240

Ile Gly Gln Glu Ala Asn Phe Glu Glu Tyr Ile Leu Asn Ala Ile Glu
                245                 250                 255
```

```
Ser His His Gly Arg Val Pro Pro Asn Asn Pro Tyr Ser Ile Ile Val
            260                 265                 270

Lys Ala Ala Asp Lys Leu Ser Ala Gly Arg Glu Gly Ala Arg Pro Arg
        275                 280                 285

Gln Ile Glu Leu Ile Asp Lys Arg Arg Lys Met Ile Glu Asp Lys Ile
    290                 295                 300

Met Ser Ile Pro Trp Ile Glu Lys Thr Ile Ile Lys Asn Ala Gly Asn
305                 310                 315                 320

Leu Ile Gln Ile Phe Ile Lys Pro Ala Glu Phe His Gly Asp Lys Ile
                325                 330                 335

Leu Glu Met Lys Glu Glu Val Arg Ala Lys Leu Lys Glu Leu Lys Ala
            340                 345                 350

Glu Tyr Ser Tyr Asn Tyr Gln Ile Glu Phe His Leu Val Phe Lys Glu
        355                 360                 365

Glu Phe Lys Phe Ser Glu
    370
```

<210> SEQ ID NO 22
<211> LENGTH: 219
<212> TYPE: PRT
<213> ORGANISM: Mycoplasma haemofelis

<400> SEQUENCE: 22

```
Val Ser Ser Tyr Ser Ile Ile Phe Glu Asn Lys Asn Phe Leu Ile Val
1               5                   10                  15

Asn Lys Ala Ser Gly Ile Ala Val His Lys Asn Ile Tyr Asp Arg Glu
            20                  25                  30

Phe Asn Leu Ile Asn Glu Val Asn Lys Asp Gln Lys Ala Asn Tyr Ser
        35                  40                  45

Leu Val His Arg Ile Asp Lys Tyr Thr Ser Gly Ala Val Leu Ile Ala
    50                  55                  60

Lys Asn Lys Glu Thr Leu Leu Leu Leu Gln Asn Leu Phe Leu Asn Asn
65                  70                  75                  80

Glu Val Glu Lys His Tyr Leu Ala Leu Thr Ser Lys Glu Leu Pro Ala
                85                  90                  95

Lys Lys Leu Lys Ile Thr Leu Ser Leu Gly Arg Ser Lys Asn Asp Lys
            100                 105                 110

Leu Arg Phe Thr Asn Arg Asn Ala Lys Asn Tyr Lys Pro Ala Cys Thr
        115                 120                 125

Glu Val Glu Val Ile Asp Arg Tyr Phe Leu Lys Ile Leu Leu Lys Thr
    130                 135                 140

Gly Arg Thr His Gln Ile Arg Ala His Leu Phe Ser Ile Asn Cys Pro
145                 150                 155                 160

Val Leu Asn Asp Pro Ile Tyr Gly Asn Arg Cys Phe Asn Pro Glu Phe
                165                 170                 175

Gly Gln Tyr Leu His Ala Tyr Lys Leu Glu Phe Thr Cys Pro Ile Thr
            180                 185                 190

Asn Glu Phe Ile Ser Val Thr Ala Pro Leu Pro Gln Glu Phe Lys Asp
        195                 200                 205

Lys Leu Ser Glu Leu Asn Ile Glu Tyr Thr Glu
    210                 215
```

<210> SEQ ID NO 23
<211> LENGTH: 202
<212> TYPE: PRT
<213> ORGANISM: Mycoplasma haemofelis

<400> SEQUENCE: 23

Met Ala Leu Ala Gly Ala Thr Gly Ala Ala Gly Gly Gly Val Leu Val
1 5 10 15

His Lys Leu Ile Asn Lys Gly Glu Asp Thr Lys Ser Asn Thr Ile Ser
20 25 30

Asn His Ile Lys Pro Glu Tyr Leu Leu Thr Asn Thr His Ala Ser Gln
35 40 45

Trp Thr His Arg Leu Asn Leu Leu Gly Lys Ala Gln Glu Thr Asp Leu
50 55 60

Ser Glu Ala Leu Leu Ser Phe Lys Lys Gly Lys Ser Ser Leu Thr Thr
65 70 75 80

Glu Asp Leu Lys Gly Trp Cys Glu Ser Ser Leu Lys Ser Glu Phe Lys
85 90 95

Ser Lys Glu Asp Lys Lys Phe Leu Asn Thr Arg Leu Tyr Cys Gly Leu
100 105 110

Asn Met Gly Asp Ser Ile Gln Glu Asn Lys Val Ser Ser Thr Thr Glu
115 120 125

Asn Gly Asn Thr Gly Leu Lys Ser Gln Phe Glu Lys Leu Lys Thr Lys
130 135 140

Lys Val Thr Glu Leu Val Ser Ala Leu Phe Ala Ile Lys Asp Lys Asn
145 150 155 160

Asn Ala Asp Ser Ser Trp Glu Gly Asn Val Ala Leu Lys Asp Trp Cys
165 170 175

Thr Lys Ala Leu Asp Met Pro Met Glu Glu Gly Leu Thr Tyr Asp Asn
180 185 190

Ala Lys Glu Tyr Cys Val Leu Thr Ala Ser
195 200

<210> SEQ ID NO 24
<211> LENGTH: 40
<212> TYPE: PRT
<213> ORGANISM: Mycoplasma haemofelis

<400> SEQUENCE: 24

Val Ala Ala Val Pro Val Ala Ala Asn Ala Pro Asn Pro Phe Lys Ser
1 5 10 15

Asp Val Phe Met Thr Lys Arg Val Asp Lys Tyr Lys Thr Pro Lys Leu
20 25 30

Pro Cys Lys Pro Phe His Leu Tyr
35 40

<210> SEQ ID NO 25
<211> LENGTH: 288
<212> TYPE: PRT
<213> ORGANISM: Mycoplasma haemofelis

<400> SEQUENCE: 25

Met Lys Thr Ser Leu Leu Lys Gly Leu Gly Ala Phe Ala Ala Thr Gly
1 5 10 15

Thr Ala Ala Thr Gly Gly Phe Val Ala Trp Lys Gln Ala Thr Lys Pro
20 25 30

Thr Asp Val Lys Ser Arg Leu Val Trp Glu Gly Leu Thr Val Ala Asp
35 40 45

Val Asn Gly Lys Gly Val Trp Gly Ala Ile Tyr Leu Ala Lys Lys Asp
50 55 60

```
Val Ser Gly Phe Leu Asp Phe Ala Thr Thr Lys Asp Asn Lys Glu Thr
65                  70                  75                  80

Ala Ser Ala Gln Leu Lys Lys Lys Cys Ser Glu Leu Phe Asn Val Ser
                85                  90                  95

Ala Gly Asp Glu Lys Tyr Glu Glu Ser Tyr Glu Lys Ala Lys Lys Trp
            100                 105                 110

Cys Leu Asn Pro Glu Leu Thr Thr Ile Glu Ile Gln Phe Glu Phe Glu
        115                 120                 125

Asp Arg Glu Phe Ala Ser Gly Asp Asp Asp Phe Lys Asn Leu Phe Thr
    130                 135                 140

Leu Tyr Lys Gly Thr Ser Ser Phe Val Asp Val Val Lys Thr Ser Ala
145                 150                 155                 160

Arg Asp Phe Thr Ala Gln Thr Ala Leu Glu Thr Ala Lys Gly Asn Val
                165                 170                 175

Gln Thr Trp Cys Asn Ser Met Lys Ser Lys Ser Pro Lys Gly Asp Asp
            180                 185                 190

Leu Lys Asn Ala Ile Ser Trp Cys Thr Lys Pro Glu Ser Asn Phe Lys
        195                 200                 205

Ser Phe Met Glu Lys Lys Gly Phe Arg Leu Leu Ala Asp Gly Glu Trp
    210                 215                 220

Gly Asn His Phe Ser Ser Leu Lys Ser Lys Gly Gly Asp Thr Ala Leu
225                 230                 235                 240

Asp Gly Asp Ile Lys Ser Glu Thr Gly Ser Asp Asp Gly Ser Lys Leu
                245                 250                 255

Lys Ser Trp Cys Asp Lys Lys Asn Val Gly Thr Val Gln Ile His Thr
            260                 265                 270

Leu Ser Ala Asp Leu Glu Lys Ile Glu Gly Arg Cys Phe Val Arg Lys
        275                 280                 285


<210> SEQ ID NO 26
<211> LENGTH: 247
<212> TYPE: PRT
<213> ORGANISM: Mycoplasma haemofelis

<400> SEQUENCE: 26

Leu Ile Trp Asp Gly Leu Ser Val Ala Asp Ser Lys Ser Leu Gly Val
1               5                   10                  15

Tyr Lys Ala Ile Tyr Leu Ala Asn Ser Asp Lys Ala Gly Phe Ser Ser
            20                  25                  30

Phe Val Ser Ala Ser Asp Lys Glu Lys Ala Ala Pro Leu Leu Lys Thr
        35                  40                  45

Lys Cys Asp Asp Leu Leu Gly Ile Ser Ala Ser Ser Asp Lys Tyr Ala
    50                  55                  60

Gln Ser Leu Glu Glu Ala Lys Lys Trp Cys Leu Val Pro Lys Lys Thr
65                  70                  75                  80

Thr Ile Glu Ile Ser Leu Leu Val Asp Gly Met Glu Leu Ser Ser Ala
                85                  90                  95

Asp Asp Asp Tyr Lys Asn Thr Phe Ala Leu Ser Arg Ser Ser Gln Asp
            100                 105                 110

Phe Ile Asn Ala Ile Lys Lys Gly Ser Asp Gly Leu Thr Thr Ser Ser
        115                 120                 125

Asp Val Asn Thr Gly Phe Ser Lys Val Lys Glu Trp Cys Ala Glu Val
    130                 135                 140

Ile Lys Lys Ser Ala Phe Asp Lys Asp Ala Gln Asn Ala Lys Leu Trp
145                 150                 155                 160
```

```
Cys Val Lys Pro Asp Ser Lys Leu Gly Asp Phe Met Asp Lys Gln Gly
                165                 170                 175

Phe Lys Pro Val Glu Ser Thr Gly Trp Asp Ser His Phe Thr Ser Leu
            180                 185                 190

Ser Ser Asp Asn Thr Leu Thr Ser Asp Met Ser Ser Val Ser Gly Thr
        195                 200                 205

Glu Gly Asn Gly Asn Lys Leu Lys Ser Trp Cys Glu Gly Lys Asn Leu
    210                 215                 220

Ala Asn Val Gln Ile His Thr Leu Leu Thr Asp Leu Glu Lys Ile Lys
225                 230                 235                 240

Ser Arg Cys Phe Val Arg Lys
                245


<210> SEQ ID NO 27
<211> LENGTH: 284
<212> TYPE: PRT
<213> ORGANISM: Mycoplasma haemofelis

<400> SEQUENCE: 27

Met Ser Ser Ala Leu Val Lys Gly Leu Ala Gly Val Ser Ala Val Gly
1               5                   10                  15

Gly Val Ser Ala Gly Gly Phe Phe Ala Tyr Lys Asn Phe Gln Ser Gln
            20                  25                  30

Asn Ile Arg Asp Val Leu Val Gly Lys Gly Leu Thr Val Ala Asn Val
        35                  40                  45

Asn Ser Val Gly Ala Trp Lys Val Ile Ala Met Gly Asn Lys Asp Asn
    50                  55                  60

Asp Ala Phe Phe Thr Phe Leu Gly Ile Thr Lys Thr Ser Asp Arg Lys
65                  70                  75                  80

Val Ala Gly Ser Lys Leu Gln Glu Arg Cys Gly Ser Ile Leu Asn Ala
                85                  90                  95

Ser Ile Lys Asp Glu Asn Tyr Ser Ser Leu Leu Ser Lys Ala Glu Ser
            100                 105                 110

Trp Cys Ile Gln Pro Thr Pro Lys Asn Leu Glu Glu Gln Leu Leu Met
        115                 120                 125

Asp Glu Leu Glu Thr Asp Leu Ser Asp Asp Asp Phe Lys Asn Val His
    130                 135                 140

Lys Ile Leu Ala Gln Asp Lys Ala Phe Thr Asp Ala Ile Glu Val Thr
145                 150                 155                 160

Lys Gly Thr Glu Ser Asp Gly Tyr Lys Lys Val Lys Lys Trp Cys Glu
                165                 170                 175

Val Glu Leu Lys Lys Pro Ala Asn Ser Pro Lys Asp Ala Ala Lys Ser
            180                 185                 190

Arg Cys Ala Thr Pro Phe Lys Asn Leu Arg Glu Ala Leu Asn Ser Gly
        195                 200                 205

Gly Leu Ser Leu Ile Ser Ser Ala Glu Asp Trp Ser Ser Arg Tyr Ser
    210                 215                 220

Ser Ile Lys Gly Thr Asp Thr Ser Leu Ser Ser Asp Gln Ile Thr Asp
225                 230                 235                 240

Ser Asp Gly Lys Gly Gly Thr Ser Leu Ser Thr Trp Cys Ser Thr Glu
                245                 250                 255

Val Asp Lys Lys Ile His Glu Leu Thr Ser Asn Tyr Thr Glu His Leu
            260                 265                 270

Asp Lys Val Lys Lys Arg Cys Val Thr Val Lys Leu
```

275 280

<210> SEQ ID NO 28
<211> LENGTH: 200
<212> TYPE: PRT
<213> ORGANISM: Mycoplasma haemofelis

<400> SEQUENCE: 28

Leu Asn Leu Asn Leu Glu Gly Lys Ala Ser Lys Leu Ala Trp Gly Leu
1 5 10 15

Gly Ile Val Gly Ser Leu Val Leu Ile Ile Ser Ser Ile Tyr Trp Ile
20 25 30

Ser Pro Thr Val Gln Asp Ser Leu Glu Asp Gln Glu Leu Gln Leu Ile
35 40 45

Ser Lys Ser Asn Glu Ser Ile Asp Leu Tyr Lys Arg Ser Phe Lys Arg
50 55 60

His Lys Asn Thr Leu Ile Ser Ile Gly Val Asp Asp Phe Ile Asn Glu
65 70 75 80

Asn Thr Val Glu Asp Glu Gly Ser Val Ala Leu His Ile Trp Cys Asp
85 90 95

Ala Asn Leu Arg Ser Lys Arg Trp Leu Val Asn Leu Asp Gly Tyr Lys
100 105 110

Arg Phe Cys Ala Leu Ser Met Gly Asp Val Leu Trp Leu Asp Lys Lys
115 120 125

Asp Glu Gly Ile Ile Asn Ser His Arg Phe Phe Ile Leu Glu Glu Glu
130 135 140

Asp Lys Arg Phe Ser Ser Arg Leu Phe Ser Lys Phe Gly Leu Thr Trp
145 150 155 160

Lys Asn Asp Lys His Ile Asp Asn Tyr Glu Ile Trp Lys Ser Arg Cys
165 170 175

Glu Ser Glu Leu Ser Glu Pro Tyr Ser Tyr Leu Asn Lys His Leu Lys
180 185 190

Thr Asp Ile Lys Asp Asn Cys Phe
195 200

<210> SEQ ID NO 29
<211> LENGTH: 202
<212> TYPE: PRT
<213> ORGANISM: Mycoplasma haemofelis

<400> SEQUENCE: 29

Met Asn Thr Leu Ala Lys Gly Ala Ile Ala Leu Thr Gly Ala Gly Gly
1 5 10 15

Ala Ala Gly Gly Gly Phe Leu Ile Ser Gln Asn Leu Gly Lys Thr Asp
20 25 30

Thr Ile Ala Asn His Ile Lys Lys Glu Tyr Leu Leu Thr Ser Glu Gln
35 40 45

Thr Asp Lys Trp Asn His Arg Val Gly Leu Leu Lys Lys Ala Gln Glu
50 55 60

Gly Gly Leu Asp Ser Ser Leu Leu Pro Leu Lys Lys Glu Gly Leu Thr
65 70 75 80

Asn Ser Glu Leu Gln Thr Trp Cys Ala Asn Gln Leu Lys Glu Lys Phe
85 90 95

Glu Gly Leu Gly Ser Asn Lys Phe Leu Asn Val Arg Leu Tyr Cys Gly
100 105 110

Leu Asn Met Gly Asn Lys Ile Ala Gly Asn Lys Val Ser Ser Ser Thr

-continued

```
        115                 120                 125

Ser Asp Ser Glu Asn Lys Leu Ala Thr Asn Phe Gly Lys Leu Asn Gly
    130                 135                 140

Lys Thr Glu Gln Glu Leu Gly Ser Ala Leu Leu Glu Ile Gly Lys Lys
145                 150                 155                 160

Thr Asn Gln Ser Ser Gly Trp Glu Gly Asn Lys Ala Leu Lys Glu Trp
                165                 170                 175

Cys Leu Lys Thr Phe Asp Leu Ala Phe Glu Glu Thr Ser Lys Asp Tyr
            180                 185                 190

Ala Asn Ala Lys Thr Tyr Cys Val Leu Val
        195                 200


<210> SEQ ID NO 30
<211> LENGTH: 205
<212> TYPE: PRT
<213> ORGANISM: Mycoplasma haemofelis

<400> SEQUENCE: 30

Met Glu Ile Ser Gly Leu Phe Lys Ala Phe Leu Ala Leu Ala Gly Val
1               5                   10                  15

Thr Gly Ala Ala Gly Gly Gly Val Leu Leu His Lys Val Ile Asn Lys
            20                  25                  30

Asp Thr Ile Ser Lys His Ile Asp Pro Lys Asn Leu Leu Thr Ser Ala
        35                  40                  45

Gln Gln Asp Lys Trp Thr His Arg Leu Gly Leu Leu Asn Lys Ala Ala
    50                  55                  60

Asp Thr Asp Leu Ser Lys Asp Leu Leu Ser Ala Lys Lys Ser Lys Thr
65                  70                  75                  80

Thr Leu Thr Ile Asp Asp Leu Lys Ser Trp Cys Ala Ser Asn Leu Glu
                85                  90                  95

Ser Glu Phe Leu Gly Thr Lys Asp Lys Lys Phe Lys Asn Ile Lys Leu
            100                 105                 110

Tyr Cys Gly Leu Asn Met Gly Asp Lys Ile Gln Gly Thr Lys Val Ala
        115                 120                 125

Ser Thr Thr Gly Gly Asp Asn Ser Ser Leu Lys Thr Asn Phe Gly Lys
    130                 135                 140

Leu Lys Asn Lys Thr Ser Ser Glu Leu Val Ser Gln Leu Phe Ser Ile
145                 150                 155                 160

Arg Asn Ala Asp Asn Thr Asn Ser Pro Trp Ser Gly Ser Thr Ser Leu
                165                 170                 175

Arg Asp Trp Cys Leu Ser Ala Phe Asp Met Pro Phe Glu Ser Gly Leu
            180                 185                 190

Thr Tyr Asp Asn Ala Lys Asp Tyr Cys Val Ile Thr Asp
        195                 200                 205


<210> SEQ ID NO 31
<211> LENGTH: 287
<212> TYPE: PRT
<213> ORGANISM: Mycoplasma haemofelis

<400> SEQUENCE: 31

Met Ser Ala Lys Thr Thr Leu Leu Lys Gly Leu Gly Ala Ser Ala Thr
1               5                   10                  15

Ala Gly Thr Val Ala Thr Gly Gly Phe Phe Ala Trp Lys Gly Leu Ser
            20                  25                  30

Gln Thr Ser Asp Ile Thr Ser Arg Leu Thr Gly Glu Gly Leu Ser Val
```

```
        35                  40                  45

Ala Asp Val Asn Lys Lys Gly Pro Trp Arg Val Ile Tyr Leu Thr Lys
    50                  55                  60

Lys Asp Val Glu Gly Phe Ser Asp Phe Val Asp Ala Ser Asp Gln Glu
65                  70                  75                  80

Asn Ala Val Ser Gln Leu Gln Lys Lys Cys Ser Glu Leu Leu Ser Ala
                85                  90                  95

Ser Pro Gln Asp Glu Asn Tyr Glu Lys Ser Tyr Glu Gln Val Lys Lys
            100                 105                 110

Trp Cys Val Asn Pro Glu Leu Lys Thr Ile Glu Met Gln Phe Val Phe
        115                 120                 125

Asp Glu Arg Glu Trp Ala Ala Ala Gly Asp Asp Phe Lys Ser Leu Phe
    130                 135                 140

Thr Leu His Gln Asn Asp Gly Asn Phe Ile Asn Ala Val Gln Ser Ser
145                 150                 155                 160

Thr Gly Phe Phe Asn Ala Ser Met Val Leu Asp Glu Ala Lys Thr Glu
                165                 170                 175

Val Glu Thr Trp Cys Asn Ser Leu Lys Ser Lys Thr Pro Glu Gly Asp
            180                 185                 190

Asp Leu Gln Asn Ala Val Ser Trp Cys Thr Lys Pro Glu Ser Asn Phe
        195                 200                 205

Lys Ser Phe Met Asp Lys Lys Gly Phe Arg Met Leu Asn Glu Ser Glu
    210                 215                 220

Trp Ala Ser Arg Phe Ser Ser Leu Lys Gly Gly Gln Asp Ser Asp Leu
225                 230                 235                 240

Ser Thr Asp Val Ser Asp Asp Asp Ser Asp Gly Ser Lys Leu Lys Gly
                245                 250                 255

Trp Cys Glu Gly Lys Lys Leu Asp Thr Val Gln Ile His Thr Leu Gly
            260                 265                 270

Ser Asp Leu Asn Lys Ile Glu Ala Arg Cys Phe Val Lys Lys Glu
        275                 280                 285


<210> SEQ ID NO 32
<211> LENGTH: 214
<212> TYPE: PRT
<213> ORGANISM: Mycoplasma haemofelis

<400> SEQUENCE: 32

Met Glu Leu Ser Phe Ala Ala Lys Met Ser Thr Gly Ala Ile Gly Ala
1               5                   10                  15

Gly Ser Ile Ala Gly Gly Gly Ala Phe Ala Ala Tyr Lys Phe Leu Asn
            20                  25                  30

Gln Glu Thr Ile Glu Lys Tyr Leu Asn Ser Leu His Arg Glu Leu Ala
        35                  40                  45

Thr Ser Asn Glu Asp Trp Glu Leu Ile Lys Asn Asn Tyr Ala Ala Asp
    50                  55                  60

Lys Glu Asp Asn Pro Ile Pro Asn Ile Pro Lys Ala Ser Ile Gly Asp
65                  70                  75                  80

Lys Leu Asn Asp Leu Lys Lys Trp Cys Ser Asp His Leu Asn Glu Glu
                85                  90                  95

Phe Ser Gln Glu Lys Ala Ser Lys Gly Asp Tyr Asn Leu Ile Gln Ser
            100                 105                 110

Trp Cys Thr Lys Gln Val Lys Ile Ser Ser Tyr Leu Lys His Leu Lys
        115                 120                 125
```

```
Leu Glu Ala Leu Glu Thr Ile Gly Thr Lys Asp Asn Glu Arg Trp Thr
    130                 135                 140

Lys Leu Lys Asp Ser Tyr Pro Asn Gly Ser Leu Lys Val His Glu Ile
145                 150                 155                 160

Asn Thr Ser Gly Asn Thr Lys Ser Glu Gly Asn Ala Val Asp Asn Leu
                165                 170                 175

Ser Gly Ser Asp Gln Lys Ile Lys Asp Trp Cys Ser Trp Ala Ser Asp
            180                 185                 190

Gln Tyr Phe Arg Tyr Lys Glu Asp Thr Leu Phe Lys Arg Tyr Glu Tyr
        195                 200                 205

Phe Cys Thr Lys Pro Ala
    210
```

<210> SEQ ID NO 33
<211> LENGTH: 215
<212> TYPE: PRT
<213> ORGANISM: Mycoplasma haemofelis

<400> SEQUENCE: 33

```
Met Val Ser Lys Ala Gly Val Ala Ala Val Gly Ala Leu Gly Ala Gly
1               5                   10                  15

Thr Ala Ser Tyr Met Gly Tyr Glu Tyr Val Phe Asn Ser Lys Glu Glu
            20                  25                  30

Val Lys Lys Thr Thr Ile Arg Glu Arg Leu Gly Asp Leu Leu Leu Asp
        35                  40                  45

Thr Ser Ser Ser Asp Lys Trp Ala Ala Arg Lys Thr Lys Leu Ser Gln
    50                  55                  60

Ala Glu Asp Thr Ser Leu Val Glu Glu Leu Lys Ser Leu Lys Asn Gly
65                  70                  75                  80

Val Ser Glu Asp Gln Val Lys Gly Trp Cys Ser Gly Ala Ala Thr Lys
                85                  90                  95

Thr Tyr Glu Asp Val Ser Ala Leu Tyr Phe Glu Asn Val Arg Thr Tyr
            100                 105                 110

Cys Thr Phe Tyr Ile Glu Asp Lys Leu Pro Glu Gly Tyr Ile Thr Lys
        115                 120                 125

Asp Ser Gln Asp Trp Ser Lys Ala Ser Asp Arg Leu Lys Asn Val Gln
    130                 135                 140

Thr Gly Val Ala Leu Ser Asp Gln Met Lys Ala Ile Lys Asp Lys Leu
145                 150                 155                 160

Thr Thr Gln Gly Ser Ser Gly Thr Asn Asp Asp Leu Lys Asn Trp Cys
                165                 170                 175

Val Gly Val Tyr Glu Lys Pro Phe Leu Gly Glu Asp Asn Gln Asp Phe
            180                 185                 190

Val Asp Ala Lys Val Tyr Cys Ala Lys Ile Glu Thr Thr Ser Thr Gly
        195                 200                 205

Ser Val Ser Pro Ala Ala Ala
    210                 215
```

<210> SEQ ID NO 34
<211> LENGTH: 197
<212> TYPE: PRT
<213> ORGANISM: Mycoplasma haemofelis

<400> SEQUENCE: 34

```
Met Leu Met Leu Gly Val Ala Gly Thr Thr Gly Thr Ala Gly Leu Gly
1               5                   10                  15
```

-continued

```
Phe Leu Ile Ala Lys Asn Gln Lys Asp Glu Ser Gln Lys Leu Arg Ser
            20                  25                  30

Lys Tyr Pro His Ala Leu Leu Thr Leu Asp Ser Asp Ser Ser Trp Ser
        35                  40                  45

Asp Lys Phe Asn Leu Leu Lys Thr Lys Thr Pro Ser His Pro Ile Leu
    50                  55                  60

Lys Gln Ala Lys Thr Gln Phe Ser Asn Thr Gln Gln Ser Gln Ser Leu
65                  70                  75                  80

Tyr Lys Lys Gly Cys Asn Ala Ile Tyr Asp Ser Glu Gly Thr Gln Tyr
                85                  90                  95

Leu Glu Asp Phe Lys Thr Phe Cys Ala Lys Thr Asn Lys Asp Gly Ile
            100                 105                 110

Thr Gly Thr Trp Ile Lys Gly Gly Ala Asp Val Asn Thr Lys Trp Asp
        115                 120                 125

Glu Lys Leu Thr Asn Leu Lys Lys Ser Thr Asp Lys Leu Ser Ser Arg
    130                 135                 140

Phe Leu Glu Val Gln Gln Ser Leu Ser Ser Asp Ser Phe Asn Asp Glu
145                 150                 155                 160

Met Arg Thr Asn Ile Gln Lys Ala Cys Asp Asn Ala Asn Ser Glu Ile
                165                 170                 175

Tyr Leu Gly Ser Glu Ser Val Glu Thr Arg Asn Ile Lys Asn Phe Cys
            180                 185                 190

Leu Thr Ser Glu Ser
        195


<210> SEQ ID NO 35
<211> LENGTH: 200
<212> TYPE: PRT
<213> ORGANISM: Mycoplasma haemofelis

<400> SEQUENCE: 35

Met Asn Pro Glu Met Met Lys Gly Ala Tyr Ala Leu Gly Ala Ala Ser
1               5                   10                  15

Ala Ile Gly Gly Gly Ala Phe Thr Ala Lys Tyr Ile Tyr Asp Arg Ser
            20                  25                  30

Ser Ser Ile Ser Ile Glu Ser His Leu Lys Ser Lys Asn Leu Thr Val
        35                  40                  45

Ile Ser Ser Leu Asn Ser Thr Ser Gln Trp Glu Glu Glu Tyr Lys Leu
    50                  55                  60

Asp Lys Asp Ala Ile Lys Ala Glu Ile Gln Ile Thr Asn Asp Asn Glu
65                  70                  75                  80

Gly Gly Thr Lys Leu Lys Glu Trp Cys Ser Gln Gln Leu Ser Lys Pro
                85                  90                  95

Phe Lys Glu Gly Glu Asp Leu Ser Lys Ile Glu Arg Trp Cys Thr Val
            100                 105                 110

Gly Lys Ile Ser Gln Arg Ile Pro Lys Gly Lys Glu Leu Leu Gln Asp
        115                 120                 125

Gly Ala Glu Ser Ser Glu Trp Glu Lys Leu Tyr Asn Lys Asn Thr Asp
    130                 135                 140

Gln Ser Glu Arg Ser Lys Leu Ser Leu Ala Ser Ser Lys Glu Asp Gly
145                 150                 155                 160

Thr Lys Asn Ser Asp Leu Thr Ala Ile Lys Lys Phe Cys Ser Asp Asn
                165                 170                 175

Lys Asp Lys Pro Phe Leu Ala Asp Arg Lys Ala Thr Glu Tyr Asp Leu
            180                 185                 190
```

```
Val Ile Leu Trp Cys Ile Lys Gln
        195                 200


<210> SEQ ID NO 36
<211> LENGTH: 475
<212> TYPE: PRT
<213> ORGANISM: Mycoplasma haemofelis

<400> SEQUENCE: 36

Met Ser Cys Ser Cys Glu Lys Pro Ser Val Ser Asn Val His Leu Asp
1               5                   10                  15

Leu Gly Tyr Trp Phe Gln Val Tyr Ser Ala Tyr Phe Arg Tyr Phe Leu
            20                  25                  30

Ile Lys Gly Arg Ile Gly Glu Asp Thr Phe Glu Ser Phe Ile Lys Lys
        35                  40                  45

Phe Glu Ser Leu Gly Leu Lys Phe Gly Cys Glu Ala Ser Leu Asp Phe
    50                  55                  60

Lys Ser Leu Asn Arg Glu Leu Asp Ser Glu Leu Ser Pro Glu Glu Arg
65                  70                  75                  80

Asp Leu Leu Ser Gln Ile Asn Glu Val Glu Ala Thr Glu Ala Ala Glu
                85                  90                  95

Lys Leu Ala Ile Lys Asp Ile Cys Asp Tyr Gln Val Arg Asp Phe Tyr
            100                 105                 110

Asp His Leu Asn Asn Phe Lys Lys Leu Ala Phe Asp Phe Arg Tyr Leu
        115                 120                 125

Ser Glu Asn Ser Asp Ser Ser Asn Pro Leu Gly Ile Gln Phe Ser Ile
    130                 135                 140

Tyr Phe Lys Asp Leu Gln Leu Leu Val Asp Lys Phe Gln Ser Asn Arg
145                 150                 155                 160

Arg Phe Val Glu Ser Phe Asn Phe Glu Thr Asp Ile Asn Gly Ser Asp
                165                 170                 175

Ser Phe Glu Ile Leu Asn Phe Leu Thr Arg Glu Leu Asp Leu Phe Pro
            180                 185                 190

Val Gln Phe Gln Ser Tyr Ser Ser Cys Asn Trp Phe Phe Leu Ala Ile
        195                 200                 205

Arg Glu Leu Ala Arg Phe Ala Arg Glu Val Ala Gly Phe Val Gln Leu
    210                 215                 220

His Gly Phe Ser Leu Ser Leu Gly Asp Met Asp Glu Tyr Leu Leu Ser
225                 230                 235                 240

Asn Val Ile Glu Ala Cys Asp Arg Val Glu Lys Asn Ser Glu Asn Val
                245                 250                 255

Ser Cys Ser Leu Glu Ser Phe Lys Ile Met Met Ile Asp Ile Ser Asn
            260                 265                 270

Leu Phe Ser Asn Leu Asn Lys Val Cys Leu Asn Ile Lys Pro Asp Glu
        275                 280                 285

Glu Phe Trp Lys Pro Cys Glu Ser Asn Glu His Leu Asp Ser Leu Tyr
    290                 295                 300

Leu Lys Ile Phe Ser Pro His Leu Leu Glu Glu Asn Leu Asn Tyr Ile
305                 310                 315                 320

Phe Leu Asn Glu Pro Glu Ile Arg Asn Ile Val Asn Lys Leu Ser Ser
                325                 330                 335

Lys Ile Asn Glu Gly Cys Ala His His Gly Asp Pro Val Cys Leu Ile
            340                 345                 350

Phe Glu Gln Arg Glu Ser Ile Pro Phe Ile Gly Gln Leu Leu Pro Tyr
```

```
        355                 360                 365

Leu Asp Phe Pro Cys Thr Leu Val Pro Leu Glu Asp Leu Ser Lys Glu
    370                 375                 380

Ser Val Glu Arg Cys Glu Gly Val Leu Asp Gly Arg Lys Ala Ile Phe
385                 390                 395                 400

Leu Gly Thr Leu Leu Arg Glu Ala Ser Tyr Ile Asp Lys Ile Lys Glu
                405                 410                 415

Ser Ile Met Lys Glu Asp Leu Lys Ile Gly Phe Leu Phe Val Phe Asp
            420                 425                 430

Ser Leu Ala Ser Thr Pro Ile Asp Ile Asp Phe Leu Gly Glu Cys Ile
        435                 440                 445

Pro Asp Glu Asp Trp Val Gly Phe Gly Leu Gly Ser Lys His Lys Cys
    450                 455                 460

Cys Asn Leu Asn Ala Ile Gly Val Leu Arg Glu
465                 470                 475


<210> SEQ ID NO 37
<211> LENGTH: 234
<212> TYPE: PRT
<213> ORGANISM: Mycoplasma haemofelis

<400> SEQUENCE: 37

Met His Asn Asp Ile Arg Val His Leu Lys Tyr Leu Ala Glu Ile Leu
1               5                   10                  15

Lys Asp Thr Leu Asn Lys Met Val Phe Met Gly Lys Ile Glu Phe Pro
            20                  25                  30

Lys Lys Leu Glu Ala Tyr Ala Asn Leu Trp Lys Glu Glu Phe Lys Asp
        35                  40                  45

Pro Phe Thr Ile Pro Leu Thr Glu Ala Glu Trp Gln Asp Ile Lys Gly
    50                  55                  60

Ile Ala Pro Gln Phe Arg Gly Asn Arg Glu Leu Gln Ser Ser Ile Lys
65                  70                  75                  80

Asn Val Lys Arg Thr Leu Glu Arg Gln Gln Phe Arg Asn Leu Ser Ile
                85                  90                  95

Leu Asn Leu Met Asp Glu Lys Leu Asn Leu Tyr Met His Ile Leu Glu
            100                 105                 110

Thr Asn Arg Gln Leu Ser Leu Leu Thr Arg Ser Ser Gln Asp Glu Val
        115                 120                 125

Ala Tyr Ile Ser Lys Asp Phe Lys Lys Arg Arg Leu Met Gly Cys Gln
    130                 135                 140

Tyr Ile His Arg Glu Val Lys Asn Val Thr Lys Leu Thr Lys Lys His
145                 150                 155                 160

Val Ile Val Asn Asp Ile Gly Ser Tyr Ile Asn Met Phe Val Asp Phe
                165                 170                 175

Ser Val Lys Glu Leu Glu His Leu Thr His Phe Ile Lys Ile Ile Arg
            180                 185                 190

Gly Ile Val Asp Glu Thr Ile Val Gly Glu Lys Leu Ala Leu Leu Lys
        195                 200                 205

Thr Arg Ile Arg Glu Gly Ser Phe Asp Leu Pro Ser Phe Arg Gln Tyr
    210                 215                 220

Met Lys Leu Glu Ser Ser Val Asn Lys Lys
225                 230


<210> SEQ ID NO 38
<211> LENGTH: 1301
```

<212> TYPE: PRT
<213> ORGANISM: Mycoplasma haemofelis

<400> SEQUENCE: 38

Met Ala Arg Arg Ser Ser Ser Ala Phe Lys Ser Gln Ser Ser Pro Asn
1 5 10 15

Asp Phe Thr Ile Lys Ala Leu Gln Ile Ser Leu Ala Ser Pro Glu Tyr
20 25 30

Val Arg Ser Leu Ser Lys Gly Glu Val Thr Ser Phe Glu Thr Ile Asn
35 40 45

Tyr Lys Ser Leu Arg Pro Glu Lys Gly Gly Leu Phe Cys Glu Ser Ile
50 55 60

Phe Gly Pro Ile Lys Asp Tyr Glu Cys Ser Cys Gly Lys Tyr Lys Gln
65 70 75 80

Val Lys Tyr Lys Gly Lys Lys Cys Glu Lys Cys Lys Val Tyr Ile Thr
85 90 95

Gln Ser Leu Val Arg Arg Asp Trp Met Gly His Ile Glu Leu Ala Cys
100 105 110

Pro Val Ala His Ile Trp Met Ile Lys Glu Leu Pro Leu Pro Ala Lys
115 120 125

Ile Ser Leu Ile Leu Gly Ile Lys Tyr Lys His Val Glu Glu Val Val
130 135 140

Tyr Phe Val Asn Tyr Ile Val Leu Asp Pro Gly His Leu Gln Val Glu
145 150 155 160

Gly Lys Thr Leu Phe Asp Pro Leu Glu Ile Ile Asp Val Ser Asn Ser
165 170 175

Lys Ser Ser Ile Ala Ser Leu Ala Lys Leu Arg Thr Leu Leu Arg Thr
180 185 190

Ile Tyr Glu Thr Ile Gln Lys Glu Asn Pro Glu Ser Tyr Leu Thr Asp
195 200 205

Leu Asn Tyr Gln Gln Gly Arg Ala Tyr Tyr Lys Ala Leu Ser Asn Ser
210 215 220

Asn Leu Pro Phe Ser Ile Met Asp Met Phe Glu Tyr Ile Glu Lys His
225 230 235 240

Thr Gly Leu Lys Val Gly Ile Gly Ala Glu Ala Ile Tyr Glu Leu Leu
245 250 255

Lys Lys Val Asp Leu Glu Ser Leu Glu Tyr Lys Leu Thr Gln Glu Leu
260 265 270

Asn Val Asn Phe Pro Ser Gly Leu Asn Tyr Ala Asp Pro Lys Val Arg
275 280 285

Lys Ile Leu Ser Arg Leu Gln Val Ile Arg Trp Phe Lys Glu Ser Lys
290 295 300

Asn Arg Pro Glu Trp Met Ile Leu Lys Val Ile Pro Val Ile Pro Pro
305 310 315 320

Asn Leu Arg Pro Ile Ile Gln Leu Ser Gly Gly Arg Phe Thr Ser Ser
325 330 335

Asp Ile Asn Thr Phe Tyr Arg Arg Ile Ile Val Arg Asn Asp Arg Leu
340 345 350

Ala Arg Ile Leu Asn Phe Asn Val Ala His Ile Ile Ser Asn Asn Glu
355 360 365

Lys Arg Met Leu Gln Glu Ala Val Asp Ser Leu Ile Asp Asn Ser Ser
370 375 380

Arg Lys Lys Pro Leu Thr Ala Arg Asp Arg His Pro Leu Lys Ser Ile
385 390 395 400

```
Thr Asp His Leu Lys Gly Lys Gln Gly Leu Phe Arg Gln Asn Leu Leu
                405                 410                 415

Gly Lys Arg Val Asp Tyr Ser Gly Arg Ser Val Ile Val Val Gly Ser
            420                 425                 430

Glu Leu Lys Met Tyr Gln Val Gly Leu Pro Ile Leu Met Ile Leu Ser
        435                 440                 445

Leu Phe Lys Pro Phe Ile Ile Arg Asp Leu Ile Arg Lys Val Asp Asp
    450                 455                 460

Asn Gly Val Glu Cys Val Pro Ile Ala Ala Asn Ile Lys Thr Ala Ser
465                 470                 475                 480

Lys Met Ile Met Glu Gln Ser Asp Glu Ile Trp Pro Val Val His Lys
                485                 490                 495

Val Ile Lys Glu Arg Pro Val Leu Leu Asn Arg Ala Pro Thr Leu His
            500                 505                 510

Arg Leu Ser Ile Gln Ala Phe Glu Pro Ile Leu Val Glu Gly Lys Ala
        515                 520                 525

Ile Cys Leu His Pro Leu Val Thr Thr Ala Phe Asn Ala Asp Phe Asp
    530                 535                 540

Gly Asp Gln Met Ala Val His Leu Pro Leu Ser Ala Glu Ala Val His
545                 550                 555                 560

Glu Ala Arg Ser Met Leu Leu Ala Pro Trp Gln Ile Leu Gly Pro Lys
                565                 570                 575

Asp Gly Lys Pro Ile Val Thr Pro Ser Gln Asp Met Val Leu Gly Ile
            580                 585                 590

Tyr His Leu Thr Thr Glu Asp Lys Glu Ala Ile Gly Phe Gly Ser Leu
        595                 600                 605

Phe Ala Thr Pro Asp Glu Val Val His Ala Tyr Gln Leu Gly Lys Val
    610                 615                 620

Asp Leu Ser Ser Ile Ile Ala Ile Gly Thr Ser Gly Phe Pro Lys Lys
625                 630                 635                 640

Arg Phe Pro Lys Ser Gly Ile Leu Ile Thr Thr Val Gly Lys Ile Ile
                645                 650                 655

Phe Asn Ser Arg Leu Pro Glu Asp Tyr Lys Phe Ile Asn Gln Ser Glu
            660                 665                 670

Gly Met Trp Val Ser Glu Asn Asp Ile Leu Asp Tyr Gly Val Ser Arg
        675                 680                 685

Leu Asp Tyr Ile Asn Ala Tyr Gln Glu Lys Glu Pro Phe Ala Lys Ser
    690                 695                 700

Val Ile Gly Arg Leu Ile Glu Asp Leu Tyr Asp Asn Tyr Ser Cys Gln
705                 710                 715                 720

Asp Leu Ala Pro Val Leu Asp Ser Ile Lys Asp Met Gly Phe Glu Tyr
                725                 730                 735

Ser Thr Lys Ser Cys Thr Thr Ile Ser Ala Phe Asp Val Pro Lys Phe
            740                 745                 750

Ser Asp Lys Gln Ser Leu Leu Glu Glu Ala Asp Lys Leu Val Glu Gln
        755                 760                 765

Gln Lys Ser Phe Phe Arg Lys Gly Leu Val Thr Asp Asp Glu Lys Tyr
    770                 775                 780

Lys Asn Val Ile Ala Ile Trp Ser Ser Val Lys Asp Lys Val Ser Asp
785                 790                 795                 800

His Ile Lys Asn Ala Leu Lys Ser Lys Glu Phe Gln Ser Asn Pro Ile
                805                 810                 815
```

-continued

```
Val Ile Met Ala Arg Ser Gly Ala Arg Gly Asn Val Ser Asn Phe Ile
            820                 825                 830

Gln Leu Ser Gly Met Arg Gly Leu Met Asn Lys Ser Tyr Asn Tyr Asp
        835                 840                 845

Gln Asn Thr Asn Thr Lys Val Val Arg Asp Ile Ile Glu Val Pro Ile
    850                 855                 860

Lys His Ser Phe Ile Glu Gly Leu Thr Val Ile Glu Tyr Phe Asn Ser
865                 870                 875                 880

Ser Tyr Gly Ala Arg Lys Gly Met Thr Asp Thr Ala Met Lys Thr Ala
                885                 890                 895

Lys Ser Gly Tyr Thr Thr Arg Lys Leu Val Asp Ala Ala Gln Glu Val
            900                 905                 910

Ile Val Lys Val Glu Asp Cys Gly Ser Asn Lys Gly Leu Ile Val Glu
        915                 920                 925

Glu Leu Arg Asp Lys Glu His Ser Met Pro Ile Lys Thr Leu Lys Asp
    930                 935                 940

Arg Ile Val Phe Lys Cys Ala His Ile Asp Ile Leu His Pro Glu Thr
945                 950                 955                 960

Gly Glu Val Ile Val Gly Ala Asn Glu Val Ile Thr Lys Glu Ala Ala
                965                 970                 975

Asp Lys Ile Val Ala Ala Gly Ile Thr Lys Val Gln Val Arg Ser Val
            980                 985                 990

Leu His Cys Arg Leu Lys Gln Gly  Ile Cys Gln Lys Cys  Phe Gly Tyr
        995                 1000                1005

Asp Leu  Thr Thr Lys Gln Met  Ile Asp Val Gly Thr  Thr Ile Gly
    1010                 1015                 1020

Val Ile  Ala Ala Gln Ser Ile  Gly Glu Pro Ala Val  Gln Leu Thr
    1025                 1030                 1035

Met Arg  Thr Phe His Ser Gly  Gly Val Ala Gly Glu  Ser Asn Ile
    1040                 1045                 1050

Ser Gln  Gly Phe Glu Arg Leu  Arg Gln Leu Phe Glu  Ile Val Ala
    1055                 1060                 1065

Pro Lys  Lys Trp Glu Thr Ser  Val Ile Ser Glu Ile  Thr Gly Thr
    1070                 1075                 1080

Val Glu  Asn Ile Glu Ile Arg  Asp Asp Glu Arg Val  Val Thr Val
    1085                 1090                 1095

Ser Ser  Asp Ile Asn Arg Arg  Glu Tyr Asn Cys Asp  Leu Asn Leu
    1100                 1105                 1110

Pro Ile  Leu Val Lys Lys Gly  Gln Lys Ile Asn Phe  Gly Asp Arg
    1115                 1120                 1125

Ile Cys  Asp Gly Ser Val Asp  Leu Lys Lys Leu Leu  Glu Val Ser
    1130                 1135                 1140

Gly Val  Glu Ala Val Arg Gln  Tyr Ile Val Gln Glu  Ile Trp Lys
    1145                 1150                 1155

Val Tyr  Trp Ile Gln Gly Ile  Asp Val Ser Glu Lys  Tyr Ile Glu
    1160                 1165                 1170

Ile Ile  Val Arg Gln Leu Thr  Ser Arg Leu Lys Val  Leu Ser Pro
    1175                 1180                 1185

Asn Asp  Ser Lys Trp Ala Met  Gly Glu Val Val Asp  Tyr Ser Ser
    1190                 1195                 1200

Phe Val  Asp Glu Cys Ala Lys  Leu Leu Leu Asp Gly  Lys Thr Pro
    1205                 1210                 1215

Pro Ile  Ala Thr Ser Ile Ile  Phe Gly Leu Glu Glu  Val Pro Glu
```

```
    1220                1225                1230

Lys Thr  Asn Ser Phe Leu Ala  Ala Ala Ser Phe Gln  Asp Thr Lys
    1235                1240                1245

Lys Ile  Leu Thr Asp Ala Cys  Val Arg Gly Gln Ile  Asp Tyr Leu
    1250                1255                1260

Asn Ser  Leu Lys Glu Asn Ile  Met Val Gly Asn Leu  Ile Pro Ala
    1265                1270                1275

Gly Thr  Gly Leu Lys Ser Ala  Asp Glu Val Ile Ser  Asp Glu Arg
    1280                1285                1290

Ser Asn  Arg Asn Val Phe Asn  Tyr
    1295                1300


<210> SEQ ID NO 39
<211> LENGTH: 226
<212> TYPE: PRT
<213> ORGANISM: Mycoplasma haemofelis

<400> SEQUENCE: 39

Met Thr Thr Ala Val Lys Thr Ser Leu Leu Ala Gly Gly Ala Ala Ala
1               5                   10                  15

Ala Ser Gly Ile Gly Ala Ile Ala Tyr Gly Asp Leu Leu Ser Phe Gln
            20                  25                  30

Thr Gln Lys Glu Ala Ile Ser Ser Leu Leu Ser Lys Asp Pro Ala Lys
        35                  40                  45

Arg Ala Ile Gly Thr Thr Glu Glu Glu Glu Trp Lys Lys Thr Trp Ala
    50                  55                  60

Arg Tyr Arg Asp Ser Lys Glu Asp Ile Trp Lys Leu Gly Asp Leu Ser
65                  70                  75                  80

Gly Asp Ala Pro Thr Glu Phe Lys Asn Ala Cys Lys Ser Lys Leu Asp
                85                  90                  95

Leu Glu Val Ser Gly Ser Asp Ser Lys Glu Tyr Lys Asp Phe Leu Leu
            100                 105                 110

Tyr Cys Ser Arg Asp Thr Leu Ile Ser Asp Leu Ile Lys Glu Asn Ser
        115                 120                 125

Lys Gly Arg Val Leu Leu Glu Gly Thr Asp Val Ser Ser Thr Asp Trp
    130                 135                 140

Gln Asn Ala Trp Lys Ala Tyr Ser Glu Asp Ser Arg Asn Gln Lys Gly
145                 150                 155                 160

Glu Ser Glu Thr Asn Ile Trp Asn Leu Ser Asp Trp Lys Thr Gln Asn
                165                 170                 175

Ser Gln Gln Asn Ala Pro Gln Ser Phe Ile Thr Lys Cys Ser Ser Asn
            180                 185                 190

Ile Lys His Pro Ser His Asp Ile His Asp Pro Leu Tyr Ile Asp Thr
        195                 200                 205

Val Lys Phe Cys Thr Lys Asp Lys Thr Thr Ala Pro Ala Ser Thr Asn
    210                 215                 220

Asn Gly
225


<210> SEQ ID NO 40
<211> LENGTH: 216
<212> TYPE: PRT
<213> ORGANISM: Mycoplasma haemofelis

<400> SEQUENCE: 40

Met Ala Val Ser Ser Leu Tyr Lys Gly Ala Ala Leu Leu Gly Gly Ala
```

-continued

```
1               5                   10                  15

Gly Ser Val Ala Gly Gly Tyr Ala Leu Ala Thr His Leu Ser Ser Asp
            20                  25                  30

Lys Lys Gln Glu Asn Lys Val Thr Ser Thr Glu Asp Arg Leu Arg Ser
        35                  40                  45

Glu Gly Tyr Thr Pro Leu Asp Phe Thr Asn Thr Asn Gly Asp Gly Trp
    50                  55                  60

Ser Lys Ile Lys Glu Ala Tyr Lys Leu Glu Asn Ser Glu Asp Lys Arg
65                  70                  75                  80

Phe Ser Gly Val Glu Lys Glu Gly Asn Asn Thr Leu Ser Gly Ile Arg
                85                  90                  95

Asp Ser Cys Leu Arg Tyr Leu Lys Glu Asp Ser Thr Asn Glu Ser Asn
            100                 105                 110

Tyr Lys Met Ser Arg Arg Trp Cys Val Val Pro Ile Ser Val Lys Asp
        115                 120                 125

Lys Leu Gly Ala Ser Asn Leu Leu Lys Ser Gly Thr Asn Glu Ser Asp
    130                 135                 140

Asp His Ser Lys Trp Asp Glu Val Val Lys Lys Asn Asp Lys Asp Ala
145                 150                 155                 160

Asn Lys Phe Val Thr Phe Ser Glu Ser Gly Lys Ser Ser Asp Asp Lys
                165                 170                 175

Arg Ala Glu Ile Lys Lys Gln Cys Glu Ala Lys Ala Ala Ile Glu Thr
            180                 185                 190

Thr Lys Glu Glu Phe Glu Glu Ser Leu Asn Gln Val Asn Leu Trp Cys
        195                 200                 205

Thr Gln Ala Ala Gly Thr Ala Gly
    210                 215


<210> SEQ ID NO 41
<211> LENGTH: 209
<212> TYPE: PRT
<213> ORGANISM: Mycoplasma haemofelis

<400> SEQUENCE: 41

Met Lys Gly Gly Val Ala Ala Ala Thr Val Gly Thr Thr Ala Thr Gly
1               5                   10                  15

Ala Tyr Val Gly Ser Arg Tyr Leu Thr Asn Thr Thr Ser Val Ser Lys
            20                  25                  30

His Leu Thr Ser Ser Gly Tyr Lys Leu Ile Ser Ser Ile Lys Asn Pro
        35                  40                  45

Asp His Leu Lys Leu Gln Trp Lys Glu Glu Phe Lys Ser Asp Lys Ala
    50                  55                  60

Ser Ile Lys Ser Leu Leu Asn Leu Lys Glu Asp Asp Glu Ser Lys Gly
65                  70                  75                  80

Gly Glu Ala Leu Gly Lys Trp Cys Thr Ser Lys Leu Ala Glu Glu Tyr
                85                  90                  95

Ser Asp Lys Val Asp Gly Leu Glu Ser Val Lys Lys Tyr Cys Val Ile
            100                 105                 110

Lys Thr Ile Lys Asp Trp Leu Ile Arg Asn Gly Asn Lys Ala Ile Leu
        115                 120                 125

Thr Glu Asn Gln Asp Asp Asn Ser Lys Trp Glu Ala Thr Tyr Asn Lys
    130                 135                 140

Arg Lys Gln Ala Lys Thr Pro Arg Thr Gln Thr Gly Leu Thr Glu Thr
145                 150                 155                 160
```

-continued

```
Trp Pro Ala Asp Ser Gly Thr Asp Lys Lys Asp Thr Asp Leu Pro Ile
            165                 170                 175

Ile Lys Arg Trp Cys Lys Glu Lys Asn Asp Ser Asp Phe Leu Ala Tyr
            180                 185                 190

Glu Asp Thr Tyr Ser His Val Lys Asp Trp Cys Thr Glu Ser Ala Asn
        195                 200                 205

Ala


<210> SEQ ID NO 42
<211> LENGTH: 195
<212> TYPE: PRT
<213> ORGANISM: Mycoplasma haemofelis

<400> SEQUENCE: 42

Met Pro Thr Leu Lys Thr Leu Val Thr Phe Pro Ile Val Gly Val Ser
1               5                   10                  15

Gly Ala Phe Ile Val Ser Asn Leu Asp Leu Ile Phe His Asp Glu Pro
            20                  25                  30

Val Asn Ile Arg Ser Lys Leu Ile Arg Asp Gly Phe Arg Leu Leu Ser
        35                  40                  45

Ser Asp Ser Ser Tyr Trp Glu Leu Leu Leu Ser Lys His Glu Glu Glu
    50                  55                  60

Ser Ser Leu Lys Glu Lys Leu Pro Ile Leu Val Asn Asn Leu Glu Ser
65                  70                  75                  80

Phe Lys Val Ala Cys Glu Glu Val Ile Gln Phe Thr Asp Leu Asn Thr
                85                  90                  95

Tyr Tyr Ser Gln Ala Ser Arg Trp Cys Val Val Pro Gln Gly Phe Glu
            100                 105                 110

Asp Arg Leu Lys Phe Ile Gly Asn Lys Glu Ile Leu Glu Ser Asp Gly
        115                 120                 125

Ile Trp Gly Asp Leu Val Ser Lys Tyr Glu Lys Asp Ser Asn Asn Ser
    130                 135                 140

Phe Val Ser Ser Leu Gly Ser Gln Ser Thr Gln Glu Leu Lys Ile Lys
145                 150                 155                 160

Glu Leu Gln Lys Phe Cys Lys Asp Thr Lys Glu Lys Glu Leu Lys Thr
                165                 170                 175

Tyr Asp Lys Asp Phe Ser Lys Asp Phe Pro Leu Phe Leu Met Trp Cys
            180                 185                 190

Thr Lys Arg
        195


<210> SEQ ID NO 43
<211> LENGTH: 207
<212> TYPE: PRT
<213> ORGANISM: Mycoplasma haemofelis

<400> SEQUENCE: 43

Met Ser Ile Ile Pro Lys Ile Ala Met Gly Thr Leu Gly Leu Gly Gly
1               5                   10                  15

Val Ala Gly Gly Gly Ile Leu Leu Ala Arg Asn Leu Gly Asn Lys Asn
            20                  25                  30

Thr Leu Ala Ser Lys Leu Glu Ser Glu Gly Phe Thr Leu Met Gly Glu
        35                  40                  45

Gly His Asp Gln Trp Ser Lys Thr Leu Ala Glu Tyr Asn Lys Val Lys
    50                  55                  60

Gly Thr Ala Glu Glu Ala Phe Lys Ile Ala Ser Ile Asp Leu Thr Val
```

```
65                  70                  75                  80

Asp Gln Leu Lys Glu Gln Cys Leu Ser Ile Leu Lys Ser Glu Ser Tyr
                85                  90                  95

Ser Glu Thr Asp Lys Asn Lys Ala Ser Arg Trp Cys Thr Ile Pro Ile
            100                 105                 110

Thr Ile Gln Ser Arg Ile Glu Lys Gln Gly Arg Arg Val Leu Asn Asp
        115                 120                 125

Val Asp Asp Asn Gln Asp Asp Lys Asp Thr Trp Val Ser Leu Val Arg
    130                 135                 140

Lys His Leu Thr Ser Pro Glu Ser Ser Arg Met Ser Val Ser Ile Thr
145                 150                 155                 160

Asp Leu Gln Asn Asp Thr Val Asp Asp Glu Arg Ile Lys Ala Met Lys
                165                 170                 175

Gly Gly Cys Arg Ser Leu Lys Ser Lys Thr Ser Leu Glu Lys Thr Tyr
            180                 185                 190

Leu Asn Asp Tyr Ser Lys Phe Gln Asp Trp Cys Ser Ala Pro Lys
        195                 200                 205


<210> SEQ ID NO 44
<211> LENGTH: 214
<212> TYPE: PRT
<213> ORGANISM: Mycoplasma haemofelis

<400> SEQUENCE: 44

Met Ala Leu Ser Thr Leu Thr Lys Gly Ser Ile Leu Leu Gly Gly Val
1               5                   10                  15

Gly Ser Ser Val Gly Gly Tyr Phe Leu Val Asn Asn Leu Thr Ser Gly
            20                  25                  30

Asp Lys Lys Glu Ala Lys Ala Ile Thr Ser Ile Arg Asp Lys Leu Thr
        35                  40                  45

Gln Glu Gly Tyr Thr Pro Leu Asn Phe Glu Asn Thr Ala Gly Ser Asp
    50                  55                  60

Trp Glu Lys Ile Lys Thr Glu Tyr Lys Lys Glu Asn Thr Asp Thr Lys
65                  70                  75                  80

Arg Phe Ser Gly Val Asn Lys Asp Asp Asp Ala Thr Val Leu Glu Gly
                85                  90                  95

Ile Lys Asn Ser Cys Leu Gln Tyr Leu Leu Gly Asp Ser Ser Asn Glu
            100                 105                 110

Asp Asn Tyr Gln Leu Ser Arg Arg Trp Cys Val Val Pro Val Ser Val
        115                 120                 125

Gln Asn Lys Leu Lys Gly Arg Thr Phe Leu Asn Thr Glu Ala Gly Gln
    130                 135                 140

Pro Asn Asn Asp Gly Glu Trp Asp Lys Ile Val Thr Lys His Asp Ser
145                 150                 155                 160

His Pro Asn Lys Trp Ile Ile Phe Glu Ala Ser Lys Ser Lys Glu Glu
                165                 170                 175

Lys Arg Thr Lys Ile Lys Glu Lys Cys Ser Ala Gln Ala Lys Leu Glu
            180                 185                 190

Thr Thr His Thr Asp Phe Glu Asp Ala Leu Arg Asn Val Asp Leu Trp
        195                 200                 205

Cys Thr Lys Glu Ser Val
    210


<210> SEQ ID NO 45
<211> LENGTH: 212
```

<212> TYPE: PRT
<213> ORGANISM: Mycoplasma haemofelis

<400> SEQUENCE: 45

Met Ser Lys Leu Ile Pro Ala Ser Leu Gly Ala Met Gly Val Ser Gly
1               5                   10                  15

Ala Gly Val Gly Ser Tyr Ile Tyr Leu Thr Ser Ser Glu Asn Lys Lys
            20                  25                  30

Glu Glu Lys Val Met Thr Phe Lys Glu Lys Tyr Ser His Ala Pro Leu
        35                  40                  45

Asp Leu Glu Gly Asn Thr Asn Asp Thr Ile Trp Ser Ser Lys Leu Thr
    50                  55                  60

Ala Leu Lys Thr Gly Ser Pro His His Pro Asp Leu Ile Ser Ala Lys
65                  70                  75                  80

Asn Ala Ile Thr Pro Gln Gly Glu Asp Lys Ala Lys Pro Leu His Lys
                85                  90                  95

Glu Ala Cys Arg Lys Ile Tyr Gly Ser Ser Ser Asp Asn Gln Asp Tyr
            100                 105                 110

Phe His Asp Phe Lys Lys Tyr Cys Ser Lys Leu Leu Gly Asp Leu Val
        115                 120                 125

Thr Gly Thr Trp Ile Ser Ser Asp Ser Asn Ser Asn Ser Ser Trp Asp
    130                 135                 140

Gly Lys Leu Asn Asp Leu Ile Ser Lys Lys Ser Glu Leu Val Ser Gln
145                 150                 155                 160

Thr Leu Lys Ser Phe Ala Glu Ser Leu Lys Thr Gly Ser Leu Thr Glu
                165                 170                 175

Glu Gln Arg Lys Thr Ile Lys Asp Trp Cys Ser Thr Gln Lys Asp Gln
            180                 185                 190

Leu Phe Ser Gly Glu Gly Asp Asn Val Ile Gln Glu Ile Lys Ser Tyr
        195                 200                 205

Cys Thr Ser Asn
    210

<210> SEQ ID NO 46
<211> LENGTH: 76
<212> TYPE: PRT
<213> ORGANISM: Mycoplasma haemofelis

<400> SEQUENCE: 46

Leu Thr Ser Pro Ser Lys Phe Asn Asn Ala Glu Gly Tyr Leu Asp Leu
1               5                   10                  15

Met Glu Val Ile Gly Ala Ser Ser Gly Val Asp Cys His Gly Leu Arg
            20                  25                  30

Ala Ile Asn Pro Pro Ala Pro Lys Pro Pro Ala Pro Ala Val Pro Ser
        35                  40                  45

Ala Ala Lys Ala Pro Phe Pro Met Leu Ile Arg Ser Ala Ile Thr Leu
    50                  55                  60

Asp Leu Leu Tyr Tyr Val Ile Ser Phe Ser Arg Lys
65                  70                  75

<210> SEQ ID NO 47
<211> LENGTH: 219
<212> TYPE: PRT
<213> ORGANISM: Mycoplasma haemofelis

<400> SEQUENCE: 47

Met Gly Lys Gly Ala Phe Ala Ala Leu Gly Thr Ala Gly Ala Gly Gly

```
1               5                   10                  15

Leu Gly Ala Gly Gly Leu Ile Ala Leu Lys Pro Trp Gln Ser Thr Pro
            20                  25                  30

Asp Glu Ala Pro Ile Thr Ser Ile Arg Ser Lys Tyr Pro Ser Ala Leu
        35                  40                  45

Leu Asn Leu Glu Gly Asp Val Asn Ile Trp Glu Lys Lys Tyr Lys Ala
    50                  55                  60

Leu Glu Thr Lys Thr Pro His His Pro Thr Leu Gln Lys Ala Leu Ser
65                  70                  75                  80

Thr Gly Lys Gly Thr Gly Ala Asn Leu Thr Glu Ala Lys Ser Leu Leu
                85                  90                  95

Lys Ser Gly Cys Arg Ala Ile Tyr Glu Ser Asp Ser Asp Asn Ser Asn
            100                 105                 110

Asn Phe Gln Asp Phe Lys Ser Phe Cys Ser Lys Thr Asn Glu Asp Ala
        115                 120                 125

Thr Lys Ser Gly Lys Gln Trp Ile Ala Asp Ala Thr Ser Lys Ala Asp
    130                 135                 140

Gly Asn Lys Trp Asp Thr Val Leu Thr Ser Leu Lys Gly His Asn Thr
145                 150                 155                 160

Trp Ser Leu Asp Ser Val Leu Glu Thr Leu Lys Lys Gly Val Gln Gly
                165                 170                 175

Asp Ser Ser Ser Phe Pro Glu Ala Arg Arg Lys Glu Leu Lys Asp Trp
            180                 185                 190

Cys Asp Lys Ala Lys Leu Glu Val Phe Val Gly Glu Ser Ser Ser Glu
        195                 200                 205

Phe Gln Ser Gln Glu Ala Phe Cys Lys Ala Asp
    210                 215
```

<210> SEQ ID NO 48
<211> LENGTH: 303
<212> TYPE: PRT
<213> ORGANISM: Mycoplasma haemofelis

<400> SEQUENCE: 48

```
Met Ile Thr Gly Ala Ala Gln Ile Asp Ala Ala Ile Leu Val Val Ser
1               5                   10                  15

Ala Thr Asp Gly Thr Met Pro Gln Thr Arg Glu His Ile Leu Leu Ala
            20                  25                  30

Arg Gln Val Gly Val Glu Arg Met Val Val Phe Leu Asn Lys Cys Asp
        35                  40                  45

Met Val Glu Asp Val Glu Met Gln Asp Leu Val Glu Met Glu Val Arg
    50                  55                  60

Asp Leu Leu Thr Ser Tyr Gly Tyr Asp Gly Ser Ala Thr Pro Val Val
65                  70                  75                  80

Arg Gly Ser Ala Leu Lys Ala Leu Glu Gly Asp Glu Lys Tyr Val Gln
                85                  90                  95

Ser Ile Lys Asp Leu Leu Gly Asn Leu Asp Glu Tyr Val Pro Leu Pro
            100                 105                 110

Val Arg Glu Val Asp Lys Pro Phe Leu Leu Ser Ile Glu Asp Val Leu
        115                 120                 125

Thr Ile Thr Gly Arg Gly Thr Val Val Thr Gly Arg Cys Glu Arg Gly
    130                 135                 140

Thr Leu Lys Val Asn Glu Glu Val Glu Ile Val Gly Leu Lys Glu Thr
145                 150                 155                 160
```

```
Ser Lys Ala Val Val Thr Gly Ile Glu Met Phe Arg Lys Pro Leu Asp
                165                 170                 175

Glu Val Leu Ala Gly Asp Asn Ala Gly Val Leu Leu Arg Gly Val Asn
            180                 185                 190

Lys Asp Glu Val Ser Arg Gly Gln Val Leu Ala Lys Pro Lys Ser Ile
        195                 200                 205

Thr Pro His Lys Lys Phe His Ala Gln Ile Tyr Ala Leu Lys Lys Glu
    210                 215                 220

Glu Gly Gly Arg His Thr Ala Phe Thr Lys Gly Tyr Lys Pro Gln Phe
225                 230                 235                 240

Tyr Phe Arg Thr Thr Asp Val Thr Gly Thr Ile Asp Leu Pro Glu Gly
                245                 250                 255

Ser Glu Met Val Met Pro Gly Asp Asn Ala Lys Ile Leu Val Glu Leu
            260                 265                 270

Ile Asn Val Val Ala Ile Glu Lys Gly Ser Lys Phe Ser Ile Arg Glu
        275                 280                 285

Gly Gly Lys Thr Ile Gly Ala Gly Thr Val Val Asp Ile Val Glu
    290                 295                 300


<210> SEQ ID NO 49
<211> LENGTH: 416
<212> TYPE: PRT
<213> ORGANISM: Mycoplasma haemofelis

<400> SEQUENCE: 49

Val Ser Cys Gly Glu Gly Gln Ile Val Ser Val Leu Gly Val Phe Phe
1               5                   10                  15

Gly Asp Glu Gly Lys Ala Lys Ile Val Asp Tyr Ile Ser Lys Asp Phe
            20                  25                  30

Asp Tyr Val Val Arg Tyr Gln Gly Gly Asp Asn Ala Gly His Thr Val
        35                  40                  45

Cys Ile Gly Asp Arg Lys Tyr Ile Phe Gln Leu Ile Pro Cys Gly Ile
    50                  55                  60

Leu Gln Thr Lys Ala Phe Ile Ala His Gly Val Val Leu Asn Pro Glu
65                  70                  75                  80

Ser Leu Leu Lys Glu Ile Gln Asp Leu Ser Glu Cys Val Glu Ile Lys
                85                  90                  95

Asp Arg Leu Phe Ile Ser Asp His Ala His Val Ile Cys Asp Trp Asn
            100                 105                 110

Ile Ala Tyr Asp Lys Phe Leu Glu Asn Leu Arg Gly Ser Gln Ala Ile
        115                 120                 125

Gly Thr Thr Asn Arg Gly Ile Gly Pro Thr Tyr Ser Asn Lys Ala Leu
    130                 135                 140

Arg Leu Gly Ile Arg Val Lys Asp Leu Leu Asp Tyr Asp Ser Leu Arg
145                 150                 155                 160

Glu Lys Ile Asp Leu Asn Leu Lys Ile Tyr Asn Val Leu Phe Lys Ser
                165                 170                 175

Tyr Gly His Pro Thr Phe Asp Leu Glu Val Glu Thr Lys Lys Tyr Phe
            180                 185                 190

Glu Tyr Gly Gln Lys Ile Lys Pro Tyr Leu Val Asp Ser Tyr His Trp
        195                 200                 205

Ile Tyr Gly Glu Leu Ser Lys Gly Lys Arg Phe Leu Phe Glu Gly Ser
    210                 215                 220

Gln Gly Leu Met Leu Asp Leu Asp Leu Gly Thr Tyr Pro Phe Val Thr
225                 230                 235                 240
```

Ser Ser Asn Ile Thr Gly Ser Leu Ile Ser Gly Thr Ser Leu Ser Phe
245 250 255

Arg His Phe Lys Arg Ile Val Gly Val Val Lys Thr Tyr Ser Ser Arg
260 265 270

Val Gly Asn Gly Glu Phe Ile Thr Glu Ile His Asp Gln Asp Leu Ser
275 280 285

Gly Tyr Ile Arg Lys Val Gly Asn Glu Phe Gly Ser Val Thr Gly Arg
290 295 300

Pro Arg Lys Ile Gly Trp Leu Asp Leu Val Ala Leu Lys Tyr Val Val
305 310 315 320

Thr Ile Ser Gly Ile Thr Glu Ile Val Leu Thr Leu Val Asp Val Leu
325 330 335

Asn Asn Leu Gly Glu Val Lys Val Cys Asn Ser Tyr Glu Tyr Ser Ser
340 345 350

Lys Glu Pro Ile Pro Val Tyr Lys Ser Phe Lys Gly Trp Lys Glu Asp
355 360 365

Tyr Ser Ser Ile Lys Arg Tyr Ser Asp Phe Ser Asp Glu Phe Lys Asn
370 375 380

Phe Val Lys Tyr Ile Glu Asp Phe Val Gly Val Pro Val Thr Ile Ile
385 390 395 400

Ser Tyr Gly Arg Ser Arg Glu Asp Thr Leu Val Arg Met Asn Glu Asn
405 410 415

<210> SEQ ID NO 50
<211> LENGTH: 262
<212> TYPE: PRT
<213> ORGANISM: Mycoplasma haemofelis

<400> SEQUENCE: 50

Met Lys Ile Lys Leu Glu Leu Pro Ser His Val Lys His Ser Ile Ser
1 5 10 15

Asn Leu Asn Arg Phe Lys Lys Glu Val Asp Leu Val Ile Asn Val Val
20 25 30

Asp Ala Arg Ala Ser Lys Thr Ser Asn Leu Asn Leu Tyr Ile Ser Arg
35 40 45

Ile Phe Ser Lys Ser Lys Ile Leu Asp Ile Phe Ser Lys Ser Asp Leu
50 55 60

Ala Ser Ser Glu Gly Leu Glu Asn Ser Phe Asn Phe Lys Ile Gln Ser
65 70 75 80

Asn Arg Asn Arg Ile Leu His Leu Ile Lys Lys Ala Leu Gln Glu Glu
85 90 95

Arg Asn Arg Leu Gln Glu Ser Gly Tyr Leu Asn Pro His Phe Lys Ile
100 105 110

Leu Val Val Gly Met Pro Asn Thr Gly Lys Ser Thr Leu Ile Asn Leu
115 120 125

Leu Lys Asn Lys Lys Ile Ser Lys Ala Ala Asn Thr Pro Gly Ile Thr
130 135 140

Arg Lys Ile Thr Gln Tyr Tyr Leu Gly Asp Asn Leu Trp Leu Phe Asp
145 150 155 160

Ser Pro Gly Ile Phe Phe Tyr Gln Asp Ile Ser Pro Glu Leu Leu Trp
165 170 175

Lys Leu Ile Val Ile Asn Ala Val Pro Ser Asn Phe Lys Glu Tyr Ser
180 185 190

Glu Ile Leu Glu Ile Thr Phe Trp Tyr Leu Lys Asp Lys Tyr Pro Asn

```
        195                 200                 205

Ser Met Asp Glu Leu Ser Ala Asp Ser Tyr Leu Ser Phe Ile Glu Leu
    210                 215                 220

Leu Ala Lys Arg Tyr Asn Phe Lys Asn Arg Gly Gly Thr Phe Asp Leu
225                 230                 235                 240

Glu Arg Ala Glu Glu Lys Phe Leu Phe Leu Leu Arg Asn Gly Gly Ile
                245                 250                 255

Arg Asp Val Ser Trp Asp
            260


<210> SEQ ID NO 51
<211> LENGTH: 297
<212> TYPE: PRT
<213> ORGANISM: Mycoplasma haemofelis

<400> SEQUENCE: 51

Leu Ser Asn Ser Ser Gln Asn Trp Leu Ser Leu Asn Leu Lys Thr Ser
1               5                   10                  15

Leu Leu Val Gly Ala Ala Ser Ile Ser Ala Ala Gly Thr Thr Ser Ser
            20                  25                  30

Val Leu Ser Asn Ala Ser Gly Gly Val Leu Glu Ala Val Lys Asn Ser
        35                  40                  45

Ser Gln Pro Ile Ile Asp Pro Phe Gln Lys Gly Tyr Ser Lys Leu Ser
    50                  55                  60

Glu Gln Leu Asp Ser Phe Ser Lys Gln Gly Tyr Asn Ala Gly Val Asp
65                  70                  75                  80

Ala Lys Ser Trp Val Thr Glu Asn Leu Ser Lys Ser Lys Ile Lys Thr
                85                  90                  95

Gly Glu Thr Asn Ile Tyr Gln Asn Leu Ser Asp Trp Tyr Arg Ala Val
            100                 105                 110

Lys Gly Phe Ala Asp Ser Ala Arg Thr Thr Ile Ser Glu Phe Phe Gln
        115                 120                 125

Lys Trp Ser Glu His Arg Glu Thr Met His Val Val Phe Lys Ala Leu
    130                 135                 140

Gly Asn Ser Phe Ser Leu Leu Gly Gly Leu Met Gly Ser Phe Glu Ser
145                 150                 155                 160

Asp Gly Glu Ser Gly Leu Lys Ile Leu Phe Glu Val Ile Gly Lys Pro
                165                 170                 175

Lys Phe Lys Asp Phe Met Thr Gln Val Ser Ser Leu Val Ser Lys Asn
            180                 185                 190

Pro Asn Leu Met Ser Ser Leu Glu Gly Asn Asp Val Met Asp Val Leu
        195                 200                 205

Ser Ala Phe Arg Gln Asp Glu Asp Thr Val Val Asp Thr Leu Lys Gly
    210                 215                 220

Leu Ser Glu Lys Asp Ala Gly Thr Val Asp Lys Ala Thr Leu Met Asn
225                 230                 235                 240

Ala Leu Lys Leu Tyr Ser Leu Met Asp Lys Ala Arg Asn Leu Met Ser
                245                 250                 255

Lys Ala Arg Thr Ile Leu Glu Ser Lys Asp Lys Glu Lys Ala Lys Gln
            260                 265                 270

Leu Ile Gln Glu Ile Thr Glu Ala His Lys Gln Met Glu Ala Leu Ile
        275                 280                 285

Lys Ala Asn Glu Gly Gln Ala Thr Glu
    290                 295
```

<210> SEQ ID NO 52
<211> LENGTH: 218
<212> TYPE: PRT
<213> ORGANISM: Mycoplasma haemofelis

<400> SEQUENCE: 52

```
Leu Gly Ser Met Ser Leu Ser Leu Ala Ser Lys Ala Thr Ala Gly Ile
1               5                   10                  15

Ala Gly Thr Gly Ala Val Ala Gly Gly Gly Ala Phe Ala Ala Tyr Lys
            20                  25                  30

Phe Leu Asn Gln Glu Thr Ile Glu Lys Tyr Leu Asn Ser Leu His Arg
        35                  40                  45

Glu Leu Ala Val Ser Asn Glu Asp Trp Glu Leu Ile Lys Asn Asn Tyr
    50                  55                  60

Ala Ala Asp Lys Ala Glu Asn Pro Ile Pro Asn Ile Pro Lys Ser Thr
65                  70                  75                  80

Ile Lys Asp Lys Leu Asn Asp Leu Lys Lys Trp Cys Ser Asp Arg Leu
                85                  90                  95

Asn Glu Glu Phe Ser Gln Glu Lys Ala Ser Lys Gly Asp Tyr Asn Leu
            100                 105                 110

Ile Gln Ala Trp Cys Thr Lys Gln Val Lys Ile Ser Asp Tyr Leu Lys
        115                 120                 125

His Leu Lys Leu Ala Ser Leu Asp Thr Ser Gly Thr Lys Asp Asp Thr
    130                 135                 140

Thr Trp Asn Lys Leu Lys Asp Glu Tyr Ser Thr Ser Gly Gly Leu Lys
145                 150                 155                 160

Val Asn Glu Ile Thr Gly Gln Glu Gly Ser Lys Thr Glu Gly Gly Glu
                165                 170                 175

Val Ser Thr Leu Ser Asp Asn Thr Lys Leu Lys Thr Trp Cys Ser Trp
            180                 185                 190

Ser Val Ser Gln Tyr Phe Lys His Gln Glu Asp Ser Leu Phe Lys Arg
        195                 200                 205

Tyr Lys His Phe Cys Thr Lys Gln Ala Asn
    210                 215
```

<210> SEQ ID NO 53
<211> LENGTH: 216
<212> TYPE: PRT
<213> ORGANISM: Mycoplasma haemofelis

<400> SEQUENCE: 53

```
Met Leu Ser Lys Ala Gly Val Ala Ala Val Gly Ala Leu Gly Ala Gly
1               5                   10                  15

Thr Ala Ser Tyr Met Gly Tyr Glu Tyr Val Phe Asn Ala Lys Glu Glu
            20                  25                  30

Val Lys Lys Val Thr Ile Gly Glu Ala Leu Glu Pro Phe Leu Leu Asn
        35                  40                  45

Thr Glu Ser Ser Asp Lys Trp Ala Ser Arg Lys Asp Lys Leu Ser Lys
    50                  55                  60

Ala Asn Glu Asp Ser Leu Val Glu Glu Leu Lys Ser Leu Lys Ser Gly
65                  70                  75                  80

Val Thr Glu Asp Gln Val Lys Asn Trp Cys Ser Val Ala Ser Thr Lys
                85                  90                  95

Val Tyr Ser Glu Val Ser Gly Leu Tyr Leu Glu Asn Val Arg Ser Tyr
            100                 105                 110
```

```
Cys Thr Phe His Ile Glu Asp Lys Leu Pro Ser Gly Tyr Ile Lys Asp
        115                 120                 125

Thr Glu Asp Trp Glu Lys Ala Asn Ser Arg Leu Lys Glu Val Asn Pro
    130                 135                 140

Asp Thr Gly Leu Ser Ser His Met Lys Glu Val Lys Asp Lys Leu Ser
145                 150                 155                 160

Lys Gln Asp Ser Pro Asp Thr Asn Ala Leu Lys Asp Trp Cys Met Gly
                165                 170                 175

Ala Tyr Gly Lys Pro Tyr Leu Gly Asp Asp Asn Gln Asp Phe Val Asp
            180                 185                 190

Ala Arg Thr Tyr Cys Ser Lys Val Ala Glu Ala Ser Pro Ser Gly Ser
        195                 200                 205

Thr Gln Ala Ala Ser Leu Pro Ala
    210                 215


<210> SEQ ID NO 54
<211> LENGTH: 202
<212> TYPE: PRT
<213> ORGANISM: Mycoplasma haemofelis

<400> SEQUENCE: 54

Met Ser Lys Leu Ala Ala Leu Ile Leu Gly Ile Ala Gly Thr Ala Gly
1               5                   10                  15

Thr Ala Gly Leu Gly Phe Leu Ile Ala Lys Asn Gln Lys Asp Glu Thr
            20                  25                  30

Lys Lys Ile Lys Asn Asn Tyr Pro His Ala Ile Leu Thr Phe Ser Asn
        35                  40                  45

Asn Glu Gly Trp Asn Ser Lys Phe Gln Leu Leu Asn Ser Lys Glu Thr
    50                  55                  60

Thr His Pro Thr Leu Lys Lys Ala Lys Ala Gln Phe Ser Asn Thr Ser
65                  70                  75                  80

Gln Ser Gln Glu Leu Tyr Lys Lys Gly Cys Asn Glu Ile Tyr Asp Ser
                85                  90                  95

Glu Gly Thr Gln Tyr Leu Asp Asp Phe Lys Thr Phe Cys Ser Lys Thr
            100                 105                 110

Asn Lys Asp Ala Ile Thr Gly Ser Trp Ile Ser Asp Ala Ala Ser Val
        115                 120                 125

Asn Thr Asn Trp Asp Lys Lys Leu Thr Ser Leu Lys Glu Arg Asn Ser
    130                 135                 140

Gly Leu Ser Ser Glu Phe Leu Glu Val Gln Ser Ser Leu Gly Ser Gly
145                 150                 155                 160

Ser Phe Asp Glu Thr Ala Arg Gly Lys Ile Lys Lys Ala Cys Asp Asp
                165                 170                 175

Ser His Ser Glu Ile Tyr Leu Gly Pro Asn Asp Ile Lys Thr Gln Ser
            180                 185                 190

Ile Lys Asp Phe Cys Leu Ser Glu Gln Thr
        195                 200


<210> SEQ ID NO 55
<211> LENGTH: 289
<212> TYPE: PRT
<213> ORGANISM: Mycoplasma haemofelis

<400> SEQUENCE: 55

Met Ala Leu Val Ser Ala Arg Glu Ile Leu Leu Lys Ala Tyr Lys Glu
1               5                   10                  15
```

-continued

```
Gly Tyr Ala Val Ala Gln Ile Asn Thr Asn Asn Leu Glu Trp Thr Lys
            20                  25                  30

Ala Ile Leu Leu Thr Val Gln Glu Leu Lys Ser Pro Val Ile Ile Gly
        35                  40                  45

Ala Ser Glu Gly Ala Ile Lys Tyr Met Gly Gly Phe Arg Thr Val Ala
    50                  55                  60

Ser Leu Val Lys Ala Met Ile Glu Asp Leu Gly Ile Thr Val Pro Ile
65                  70                  75                  80

Ile Leu His Leu Asp His Gly Ser Tyr Glu Gly Cys Lys Lys Ala Met
                85                  90                  95

Asp Ala Gly Phe Ser Ser Val Met Phe Asp Gly Ser His Phe Pro Ile
            100                 105                 110

Asp Glu Asn Phe Gln Lys Ser Lys Glu Ile Val Asp Leu Ala Asn Ser
        115                 120                 125

Arg Gly Ile Ser Val Glu Leu Glu Val Gly Thr Ile Gly Gly Glu Glu
    130                 135                 140

Asp Gly Val Ile Gly Ala Gly Glu Asn Ala Ser Val Asp Glu Cys Val
145                 150                 155                 160

Lys Ile Gly Gly Leu Asp Leu Ser Met Leu Ala Ala Gly Ile Gly Asn
                165                 170                 175

Ile His Gly Pro Tyr Pro Asp Asn Trp Lys Gly Leu Asn Phe Pro Leu
            180                 185                 190

Leu Lys Glu Ile Ser Asp Ala Val Lys Lys Pro Met Val Leu His Gly
        195                 200                 205

Gly Thr Gly Ile Pro Glu Asp Gln Ile Lys Lys Ala Ile Ser Leu Gly
    210                 215                 220

Ile Ser Lys Ile Asn Val Asn Thr Glu Leu Gln Leu Ala Phe Ala Ala
225                 230                 235                 240

Ala Thr Arg Lys Tyr Ile Glu Glu Lys Asn Asp Leu Asn Met Ser Lys
                245                 250                 255

Lys Gly Phe Asp Pro Arg Lys Leu Leu Lys Tyr Gly Tyr Asp Gly Ile
            260                 265                 270

Cys Gln Val Ile Lys Asp Lys Leu Thr Met Phe Gly Ser Val Gly Lys
        275                 280                 285

Ala


<210> SEQ ID NO 56
<211> LENGTH: 190
<212> TYPE: PRT
<213> ORGANISM: Mycoplasma haemofelis

<400> SEQUENCE: 56

Met Ser Lys Asp Asn Lys Glu Gln Lys Glu Glu Glu Ile Val Glu Glu
1               5                   10                  15

Val Ser Glu Leu Asp Gln Leu Lys Ala Lys Leu Lys Glu Trp Glu Asp
            20                  25                  30

Lys Phe Ser Glu Leu Glu Lys Glu Ser Asn Gln Arg Leu Leu Glu Phe
        35                  40                  45

Val Glu Lys Lys Ser Lys Glu Ala Ser Asp Ile Ile Ala Lys Lys Glu
    50                  55                  60

Glu Glu Ile Ser Gln Arg Tyr Lys Lys Glu Leu Glu Glu Ala Lys Asp
65                  70                  75                  80

Tyr Leu Tyr Glu Lys Pro Leu Ala Ser Leu Val Gly Val Ile Ser Gln
                85                  90                  95
```

-continued

```
Phe Glu Ala Val Ile Lys Met Thr Val Asp Pro Asn Ile Ser Gln Tyr
            100                 105                 110

Leu Val Gly Phe Arg Met Phe Leu Thr Gln Phe Asn Asp Leu Leu Arg
        115                 120                 125

Glu Phe Ser Ile Ser Ile Ile Glu Pro Lys Asp Gly Asp Glu Phe Asp
    130                 135                 140

Ser Ser Phe Met Glu Ala Thr Val Val Glu Lys Val Ser Asp Asp Ser
145                 150                 155                 160

Leu Asn Asn Lys Val Ile Ser Val Phe Ser Lys Gly Tyr Arg Leu Lys
                165                 170                 175

Asp Arg Ile Ile Arg Leu Ala Ser Val Lys Val Gly Lys Ile
            180                 185                 190


<210> SEQ ID NO 57
<211> LENGTH: 368
<212> TYPE: PRT
<213> ORGANISM: Mycoplasma haemofelis

<400> SEQUENCE: 57

Met Ala Ser Lys Asp Tyr Tyr Ser Ile Leu Gly Ile Ser Arg Asn Ala
1               5                   10                  15

Thr Glu Asp Asp Ile Lys Lys Ala Tyr Arg Lys Leu Ala Lys Lys Tyr
            20                  25                  30

His Pro Asp Ile Asn Lys Glu Ala Gly Ala Glu Ala Lys Phe Lys Asp
        35                  40                  45

Ile Asn Glu Ala Tyr Glu Thr Leu Gly Asp Pro Gln Lys Arg Ser Asn
    50                  55                  60

Tyr Asp Asn Phe Gly Thr Ser Gly Asp Gly Met Gly Gly Ala Gly Gly
65                  70                  75                  80

Ala Asn Pro Phe Asp Ile Trp Asn Ser Phe Phe Ser Gly Gln Ala Ser
                85                  90                  95

Gly Gly Phe Ser Glu Phe Asp Ile Phe Gly Gly Ser Asp Ser His Gln
            100                 105                 110

Ser Gln Pro Gln Tyr Glu Asn Tyr Gln Asp Arg Ile Val Ile Ser Phe
        115                 120                 125

Leu Ala Ser Ile Lys Gly Val Asn His Ser Phe Thr Tyr Glu Ser Glu
    130                 135                 140

Lys Arg Cys Glu Val Cys Lys Gly Asn Lys Ala Leu Asp Gly Asp Ser
145                 150                 155                 160

Lys Tyr Ile Ile Thr Cys Asp Asn Cys Arg Gly Thr Gly Trp Glu Met
                165                 170                 175

Leu Arg Lys Gln Thr Ile Phe Gly Val Val Asn Thr Lys Ala Ser Cys
            180                 185                 190

Arg Arg Cys Asn Gly Gln Gly Lys Met Ile Ser Lys Pro Cys Lys Glu
        195                 200                 205

Cys Gly Gly Arg Gly Tyr Lys Lys Phe His Lys Thr Gln Asn Phe Ser
    210                 215                 220

Ile Pro Ala Gly Val Gln Asp Lys Asp Val Leu Val Ala Trp Asp Lys
225                 230                 235                 240

Thr Gly Ile Val Asp Lys Lys Ile Ser Ile His Val Ser Val Arg Pro
                245                 250                 255

Ser Glu Ile Phe Ser Arg Lys Gly Asn Asp Leu Tyr Thr Arg Ile Val
            260                 265                 270

Ile Asn Pro Phe Val Ala Ile Phe Gly Gly Thr Ala Ser Ile Pro Thr
        275                 280                 285
```

Ile Ser Gly Ile Lys Ser Ile Lys Ile Ala Ala Gly Thr Asn Ser Gly
    290                 295                 300

Glu Lys Leu Lys Leu Lys Gly Leu Gly Val Lys Ser Ser Ala Gly Arg
305                 310                 315                 320

Gly Asp Leu Ile Gly Glu Val Cys Phe Ala Pro Val Pro Lys Leu Thr
                325                 330                 335

Lys Glu Gln Lys Glu Val Leu Lys Ser Leu Ser Asp Leu Glu Val Pro
            340                 345                 350

Glu Val Thr Arg Trp Val Ser Lys Ala Lys Lys Ala Val Val Ser Asp
        355                 360                 365

<210> SEQ ID NO 58
<211> LENGTH: 673
<212> TYPE: PRT
<213> ORGANISM: Mycoplasma haemofelis

<400> SEQUENCE: 58

Met Ala His Ile Asp Ala Gly Lys Thr Thr Thr Ser Glu Arg Ile Leu
1               5                   10                  15

Phe His Thr Gly Lys Thr Tyr Lys Ile Gly Glu Val His Asp Gly Ala
            20                  25                  30

Ala Thr Met Asp Trp Met Glu Gln Glu Lys Glu Lys Gly Ile Thr Ile
        35                  40                  45

Thr Ala Ala Ala Thr Ser Val Ser Trp Lys Asn His Gln Leu Asn Leu
    50                  55                  60

Ile Asp Thr Pro Gly His Val Asp Phe Thr Val Glu Val Glu Arg Ser
65                  70                  75                  80

Leu Arg Val Leu Asp Gly Ala Val Ala Val Leu Asp Ser Gln Met Gly
                85                  90                  95

Val Glu Pro Gln Thr Glu Thr Val Trp Arg Gln Ala Thr Lys Tyr Ser
            100                 105                 110

Val Pro Arg Ile Val Tyr Cys Asn Lys Met Asp Lys Ile Gly Ala Asp
        115                 120                 125

Phe Phe Lys Ser Val Gln Ser Leu Arg Asp Lys Leu Lys Val Lys Ala
    130                 135                 140

Val Leu Val Gln Leu Asn Ile Gly Lys Glu Ser Glu Phe Thr Gly Ile
145                 150                 155                 160

Ile Asp Leu Ile Ala Lys Lys Ala Tyr Ser Phe Asp Gly Lys Gln Glu
                165                 170                 175

Glu Glu Tyr Lys Glu Ile Pro Ile Pro Asp Asn Leu Lys Gly Glu Val
            180                 185                 190

Asp Arg Leu His Gln Glu Leu Leu Asp Glu Val Leu Val Phe Asp Glu
        195                 200                 205

Lys Ile Met Glu Lys Tyr Leu Gly Gly Glu Glu Val Thr Ile Asp Glu
    210                 215                 220

Ile Lys Arg Cys Ile Arg Ile Gly Thr Ile Gln Thr Lys Leu Phe Pro
225                 230                 235                 240

Val Phe Cys Gly Ser Ser Phe Lys Asn Lys Gly Val Lys Phe Leu Leu
                245                 250                 255

Asp Ala Ile Ile Asp Tyr Leu Pro Ser Pro Val Asp Leu Pro Glu Thr
            260                 265                 270

Pro Ala Phe Asp Lys Glu Gln Asn Pro Ile Ser Ile Lys Asn Ser Ala
        275                 280                 285

Glu Gly Glu Phe Val Gly Met Ala Phe Lys Ile Ala Thr Asp Pro Phe

-continued

```
    290                 295                 300

Val Gly Arg Leu Thr Phe Ile Arg Val Tyr Ser Gly Ile Leu Lys Lys
305                 310                 315                 320

Gly Ser Ala Ile Tyr Asn Thr Thr Gln Asp Leu Pro Glu Lys Ala Gly
                325                 330                 335

Arg Leu Val Gln Met His Ser Asn His Arg Thr Glu Ile Glu Ser Ile
            340                 345                 350

Gln Ala Gly Glu Ile Cys Ala Ile Val Gly Leu Lys Asn Thr Arg Thr
        355                 360                 365

Gly Asp Thr Leu Thr Val Lys Gly Asn Ala Val Val Leu Glu Ser Met
    370                 375                 380

Asn Phe Ala Glu Pro Val Ile Ser Leu Ala Ile Glu Pro Lys Thr Lys
385                 390                 395                 400

Val Asp Gln Glu Lys Met Ser Met Val Leu Ser Arg Leu Ser Glu Glu
                405                 410                 415

Asp Pro Thr Phe Lys Ile Ser Thr Asn Val Glu Thr Gly Gln Thr Ile
            420                 425                 430

Ile Ser Gly Met Gly Glu Leu His Leu Glu Ile Leu Ile Asp Arg Met
        435                 440                 445

Asn Arg Glu Phe Gly Leu Gln Val Asn Ile Gly Gln Pro Gln Val Ala
    450                 455                 460

Phe Arg Glu Thr Phe Thr Gln Val Ser Asp Val Glu Gly Lys Tyr Ile
465                 470                 475                 480

Lys Gln Ser Gly Gly Arg Gly Asn Tyr Gly His Val Trp Ile Lys Phe
                485                 490                 495

Glu Pro Asn Lys Asp Lys Gly Phe Glu Phe Val Asp Lys Ile Val Gly
            500                 505                 510

Gly Lys Ile Pro Lys Glu Tyr Ile Lys Ser Ile Arg Gln Gly Leu Ile
        515                 520                 525

Asp Ala Met Lys Ser Gly Pro Leu Ala Gly Tyr Pro Ile Ile Asp Ile
    530                 535                 540

Lys Ala Thr Leu Phe Asp Gly Ser Phe His Glu Val Asp Ser Asn Glu
545                 550                 555                 560

Met Ala Phe Arg Ile Ala Ala Ser Leu Ala Leu Lys Asp Ala Ser Lys
                565                 570                 575

Lys Cys Ala Ser Ile Leu Leu Glu Pro Ile Met Asn Val Glu Ile Thr
            580                 585                 590

Val Pro Leu Gln Tyr Phe Gly Thr Val Met Gly Asp Val Thr Ser Arg
        595                 600                 605

Arg Gly Leu Ile Glu Gly Thr Glu Gln Val Glu Asn Ala Gln Ile Ile
    610                 615                 620

Lys Ser Lys Ile Pro Leu Lys Glu Met Phe Gly Tyr Ala Thr Val Leu
625                 630                 635                 640

Arg Ser Phe Thr Gln Gly Arg Gly Ile Tyr Thr Met Gln Phe Ser His
                645                 650                 655

Tyr Gln Pro Leu Pro Lys Ser Ile Thr Gln Glu Met Leu Glu Gly Arg
            660                 665                 670

Lys
```

<210> SEQ ID NO 59
<211> LENGTH: 557
<212> TYPE: PRT
<213> ORGANISM: Mycoplasma haemofelis

<400> SEQUENCE: 59

```
Leu Gln Lys Ile Lys Asp Tyr Leu Ser Ser Glu Phe Asn Leu Ala Ala
1               5                   10                  15

Gln Ala Leu Gly Tyr Arg Leu Thr Gly Ile Glu Ala Ser Phe Asp Phe
            20                  25                  30

Thr Lys Asp Tyr Lys Phe Gly Asp Ile Phe Thr Asn Phe Ala Cys Arg
        35                  40                  45

Ile Ser Ser Lys Tyr Lys Lys Asn Pro Lys Asp Val Gly Glu Glu Leu
    50                  55                  60

Leu Lys Gln Val Gly Glu Leu Lys Tyr Val Ser Ser Ala Lys Val Glu
65                  70                  75                  80

Lys Asn Gly Phe Ile Asn Ile Phe Phe Ser Pro Glu Ile Phe Ser Glu
                85                  90                  95

Tyr Tyr Ser Glu Ile Leu Glu Lys Arg Glu Asp Ile Trp Arg Lys His
            100                 105                 110

Pro Ile Asn Ser Trp Tyr Phe Val Glu Ile Val Ser Ala Asn Pro Thr
        115                 120                 125

Gly Leu Leu His Ile Gly His Ala Arg Asn Gly Ile Phe Ser Asp Thr
    130                 135                 140

Leu Ala Asn Leu Leu Glu Tyr Gly Gly Tyr Phe Val His Arg Glu Tyr
145                 150                 155                 160

Leu Val Asn Asn Leu Gly Asn Gln Ile Lys Glu Leu Leu Glu Ser Ile
                165                 170                 175

Trp Ile Lys Tyr Lys Ala Lys Leu Thr Ser Ile Pro Arg Glu Ser Asn
            180                 185                 190

Thr Lys Val Val Lys Tyr Asn Gly Lys Glu Ile Asp Glu Cys Val Asp
        195                 200                 205

Tyr Leu Ile Ser Thr His Gly Gln Arg Trp Ile Phe Asp Arg Asn Ile
    210                 215                 220

Phe Glu Ser Lys Ser Tyr Pro Glu Leu Glu Lys Leu Val Val Ser Tyr
225                 230                 235                 240

Phe Leu Asn Glu Ile Glu Lys Asp Leu Ala Arg Tyr Asn Ile Glu Val
                245                 250                 255

Asn Ala Trp Lys Phe Glu Ser Ser Phe Val Asn Ser Glu Ser Ile Asn
            260                 265                 270

Asp Leu Phe Lys Ser Met Lys Glu Tyr Leu Arg Val Lys Asp Gly Ala
        275                 280                 285

Ile Trp Phe Lys Ala Gly Glu Ile Leu Asp Glu Cys Lys Asp Glu Val
    290                 295                 300

Leu Ile Lys Asn Asp Gly Lys His Thr Tyr Tyr Cys Gln Asp Leu Ile
305                 310                 315                 320

Tyr His Leu Tyr Lys Leu Ser Leu Leu Gly Asn Glu Gly Lys Ile Ile
                325                 330                 335

Asn Val Leu Gly Ser Asp His Tyr Gly His Ile Asp Lys Leu Lys Ala
            340                 345                 350

Phe Leu Lys Leu Lys Glu Val Asp Asp Asp Arg Val His Phe Ile Cys
        355                 360                 365

Met Gln Leu Val Lys Leu Met Glu His Ser Thr Leu Val Lys Ile Ser
    370                 375                 380

Lys Arg Asp Ser Lys Val Ile Tyr Leu Arg Asp Leu Met Asn Tyr Met
385                 390                 395                 400

Thr Tyr Glu Glu Ala Arg Trp Phe Leu Val Ser Gln His Pro Asp Ser
                405                 410                 415
```

```
Pro Leu Glu Ile Asp Ile Gln Arg Leu Lys Gln Lys Asn Tyr Asn Asn
            420                 425                 430

Pro Ala Phe Tyr Val Met Tyr Ala Tyr Ser Arg Ile Phe Gln Ile Leu
        435                 440                 445

Arg Lys His Gly Glu Pro Tyr Phe Tyr Ser Lys Lys Glu Val Leu Phe
    450                 455                 460

Lys Thr Ile Thr Asp Gly Ile Glu Lys Thr Ile Met Asn Thr Leu Met
465                 470                 475                 480

Gln Trp Asp Glu Val Ile His Glu Ala Ile Glu Thr Leu Gln Pro Tyr
                485                 490                 495

Arg Ile Thr Gln Tyr Leu Phe Lys Leu Ala Lys Glu Phe His Ser Phe
            500                 505                 510

Tyr Glu Glu Thr Lys Leu Leu Gln Glu Gly His Glu Glu Glu Trp Leu
        515                 520                 525

Arg Asp Arg Leu Ala Leu Leu Asn Ala Ala Lys Tyr Thr Ile His Ser
    530                 535                 540

Gly Leu Ser Ile Leu Lys Ile Lys Pro Lys Ser Val Ile
545                 550                 555


<210> SEQ ID NO 60
<211> LENGTH: 204
<212> TYPE: PRT
<213> ORGANISM: Mycoplasma haemofelis

<400> SEQUENCE: 60

Met Thr Tyr Ala Lys Leu Gly Ala Ala Thr Leu Gly Thr Ala Gly Ala
1               5                   10                  15

Ala Gly Gly Gly Tyr Leu Ala Tyr Pro His Val Phe Pro Glu Arg Thr
            20                  25                  30

Leu Leu Asp Glu Leu Lys Ser Gln Asn Lys Ser Val Ile Asn Gly Asn
        35                  40                  45

Glu Ser Gln Trp Thr Leu Lys Lys Glu Leu Tyr Asn Lys Gly Thr Asn
    50                  55                  60

Ser Ser Lys Ile Thr Ile Asp Asn Lys Glu Lys Ala Ser Ile Thr Glu
65                  70                  75                  80

Ala Glu Leu Lys Lys Trp Cys Ser Asp Asn Leu Lys Ala Pro Tyr Ser
                85                  90                  95

Lys Ala Lys Asp Ser Ile Leu Gly Lys Val Glu Lys Trp Cys Leu Lys
            100                 105                 110

Pro Asn Ile Lys Glu Ala Leu Ser Lys Glu Thr Lys Glu Ile Ile Ser
        115                 120                 125

Phe Thr Gly Thr Thr Ile Asp Ala Ala Trp Glu Ser Lys Leu Thr Thr
    130                 135                 140

Asn Ser Ser Ser Val Lys Gly Glu Leu Ile Asp Lys Trp Lys Leu Pro
145                 150                 155                 160

Val Ser Ser Glu Gly Asn Asp Lys Val Ser Lys Glu Ser Leu Arg Asp
                165                 170                 175

Ala Cys Gln Leu Lys Val Glu Gly Glu Tyr Ile Ser Glu Asn Asp Glu
            180                 185                 190

Asn Tyr Thr Leu Ser Lys Lys Trp Cys Leu Lys Pro
        195                 200


<210> SEQ ID NO 61
<211> LENGTH: 774
<212> TYPE: DNA
```

<213> ORGANISM: Mycoplasma haemofelis

<400> SEQUENCE: 61

```
atgtcagcat tagcccccct taaacttgcg ggattatcct gtttgggtgt tggaggaact     60
tgtagtgtag tttatgctgg aagttcttga gtatcgggtg tttcttcatt ggaaactgat    120
gatgacaatg ttatacagac cgttgccgat aaattcagta ataggttaat aggcaaggga    180
aagacaagta tctggaacgc tcgccttcaa aagcttagat ctgccggcaa tagtaagcaa    240
ttggatgctg gtcttaaggc tataaaggat gatacgaaca agaaagatac cgatctacag    300
acttgatgtg aagaggctaa gataaagccc caagaaggag aaggatctaa gttgatagta    360
gagggagttc aggattattg tacttacacc atcaaagatc aagctaatgg aactatgtct    420
aaaaccaaga caaatgtttc agactgaaag gaagttaata cggccttttc taagatgaag    480
agggattctt tatccaagga cttacaagca gtttgagata aggtaaagga taagactgat    540
acttctggag atcttaagga ttggtgtttt aagaagtatg atgagccttt tgaaggtagg    600
gatagtgcta cttataaaga tgtagttaag gtatgtaaaa ctgtacctaa gccagcagcc    660
gccaaaccgg cagcggctaa acccgtcgct tccaagcctt cttctgattc taaacaagta    720
gcaggaacag agcctacatc accagctccc acaaaacaag caggagatat ctaa          774
```

<210> SEQ ID NO 62
<211> LENGTH: 708
<212> TYPE: DNA
<213> ORGANISM: Mycoplasma haemofelis

<400> SEQUENCE: 62

```
ttggatatga gcacactatt aaagggatca ctaggcttat tgggagcagg aagcgcaact     60
actgctggag ccatttactt aggtacagat atctttaaat ccaaggagga taagaaggta    120
tccatttcaa agctattaaa gacttccaac cctgaaaaga ggttaattac ctcttcacaa    180
gcttcagatg gagattggaa agaagcttga aagaactata gagttgcgaa caagggtaag    240
aagttaaatg aggatgagtg gaagctatcc ggttgagtta ctccacaaga tggcaatatc    300
actaatacag agaatgcttc cgatagcttt atgaatactt gctctattaa taaagacaag    360
gaggtatctg gaacggatga tcctttatat aaagccgtat tagtttactg cactagatca    420
acattagtta gtgatttaat ttctgataat tatccaaata agaaaatact tacttcagca    480
aataatgatg atgccggttg aaaggaggct tgaacccaat acaagaccga taattccgga    540
aagagtacac aaaatagcga cgcatggcaa ttggcgggtt gacctacatc cactccagat    600
accgttttag agagctttaa gactaaatgt ggagagaagg ttaaagtagc tacttttaag    660
acggacaacg aggactacac caacgcagtt aagtgatgta ctaagtaa                708
```

<210> SEQ ID NO 63
<211> LENGTH: 630
<212> TYPE: DNA
<213> ORGANISM: Mycoplasma haemofelis

<400> SEQUENCE: 63

```
atggcggttt ccgtagtgaa agccgcctcg gggctgggag ttgcagcagc tactgtaggt     60
ggaggaatat ttgtagctaa gggaatggaa ggatctcctt ccactcctaa aagtacagtt    120
caagataagt taaagcagaa tggttattct cctttggact tggaaaagag tgatggatga    180
agtgaggttt tagaggcata caatcaacat aagaataatc cctccattag atttgatcat    240
ggagataggg agattagtga acaggaatta aaggatgcct gttcatcagc tttcaatagt    300
```

gatgacaagt atgagaatgc taagaggtgg tgtgttgttc cctattctgt atctcaagta 360
ttaacttcca agtcattaaa agtcttgaat gttaatgata ctggagatga tgatcaagat 420
gatcaagatg agtgagataa cttgaagggg caatatcaag agaatgcaat tcctgggttg 480
gttcttaaat caacagaaga ctgacagtca ttaagaacta agtgcaagga attagtggag 540
aagaagccgt ggagtgatgg ttatgaggat tctatttctc acgccacaag atgatgtact 600
catgcgtttg tgaataactc cgatagttag 630

<210> SEQ ID NO 64
<211> LENGTH: 630
<212> TYPE: DNA
<213> ORGANISM: Mycoplasma haemofelis

<400> SEQUENCE: 64
atggagccat taaagttagc ttttttagct acaggagctg gtgcgactgg attaggtact 60
tatggtctat attctcatct ctctggctct cagaaggaaa atgtgggaac taggttagta 120
agcgagagtt ttgaattact gaatgattca cataaggcgc aatggaagac ttctttagag 180
aagtacaatg gaaagaagga tgccaatgct tccaatatcg atgagacgaa attaaaggct 240
atttgtaaga gtcttatttc taaggataag acttctgaag cagattataa aaaggccaaa 300
ttgtattgtg tggtgcctca gggagtatct gagaggctat ctaaattagg gtttaaggtc 360
ttgaatactt ccgataccac ccaccagaat gagtggacta aattagctac ttcttatgtt 420
actaatggaa agggagataa gcaaatagag tctttaactc ttacaacccc ttcaggatcc 480
accgacaata attgaagtac cttgaaggag aattgcaaga ctattttagg taagtctcac 540
tgagaagaga gctttgactc ttattttgag aaatctaaga tgtgatgtac tgaagaagcc 600
tttaattctt tacctaaaga gaagcagtag 630

<210> SEQ ID NO 65
<211> LENGTH: 708
<212> TYPE: DNA
<213> ORGANISM: Mycoplasma haemofelis

<400> SEQUENCE: 65
atgaagatag tatttggaaa cctgaagatg aacttcctgt acaaggattt tcaggattat 60
attgagaatc taagaatgaa gttcttaggc gagactccta aggtacatct cgggttagct 120
attccttaca tatatctgaa gagtgcttct gagtcaattg gatccaagat taaagtgtta 180
gctcaagacc ttcatcctgt ggattttggt gcttttacgt cctccgtttc tgcggctcaa 240
cttgcttctc ttaatgttcc tgcgacattg attggacatt ctgaatgtag acagctaagt 300
cagaattcct ttgttatctc taacaagata aagtctgctt tgagaaatgg attggagatt 360
atctattgct gtggggagga tcccgagaag gaaatatctg aagagctatt cttcatgacc 420
gaggaggaga taagtaaggt gataattgct tatgaaccta tttcttcaat agggactggg 480
caagctatgg atcctagtgg ggctgattct actcttctta agataagaga tttaatagct 540
gataagtatg gaaggaaggt agctgactct atgaagttat tgtatggtgg ttctgttaat 600
ttgtctaact ataaagggta cctagagaag aagaatatag atggagtttt ggttggtggg 660
gcttccttga aggttgatga tctttgaaaa atggcaactt tagaataa 708

<210> SEQ ID NO 66
<211> LENGTH: 1485
<212> TYPE: DNA

<213> ORGANISM: Mycoplasma haemofelis

<400> SEQUENCE: 66

```
atggatggtt gaggtttaac ctcagaatcc aaagggaacg ctccactttt ggctaagacc     60
ccaaccttag attttcttta caaagaatat cctaattcca cactttcagc gtctgaggag    120
gcagttggtt tacctgctgg tcagatggga aattcagagg ttggtcatat aaatcttggg    180
gctggtagag tagtttatac cggtttgtct ctaataaata agtgcattaa ggatggagct    240
cttgagagtc agcctgctgt agtagagttt tttgatttag ttaaaagcag gggctccaaa    300
cttcacttcc tttctcttat ttcagaaggg ggagttcatt ccaatatgaa ccacttctta    360
gctttcgcag atatctgcgt aaagagaaat caaccatata ttcttcatgc atttacagat    420
ggaagagatg tgtctcctaa tgcagctaaa actgatttta ttcctatagt tcagaagctt    480
aaggatacta atgggaagtt aggagttgta tccggtcgtt attattccat ggacagggat    540
aagaactggg atagagagga gaaggtattt aagtacttag ttggctctga caagtctaga    600
acctttgatg atgttcttgt ttatatagag caatcctacg cgtctggagt tacagatgag    660
ttcattgaac cggctatctg ctcttcctcc ttagattcag tgataggcga taatgatgta    720
gttgttttcc taaattttag acccgataga gctagacaaa tttcccatat gttagtggga    780
tctaagggtt tatatgacta cgaaccttct gtgaagctta ataatgtttc actatttgca    840
ttgatggatt acgagaagat aaatcttcag aacactctat tccctccttt tgatatcaaa    900
aatactctag gagagtttct gtccaacaac ggtatttctc aattgagaat tgctgagact    960
gagaagtatc cacacgttac tcacttcttt gatggtggta agactttgga ttaccctaag   1020
atgaagaaga ttttgattcc gtctcctaag gtagctactt acgatttaca accggagatg   1080
tctgctccta agattacgga agctctattg ccggaattga agaactttga ggtggtaata   1140
ttgaattttg caaatccgga tatggttgga catactggtt ctttagaggc tactataaag   1200
gcttgtgaga gtgtggatac tcagattggg aagatttatg aggaggttca aaaactcggg   1260
ggagttttgg tggtgatagc ggatcacggt aatgctgaag ttatgattac tgcggatggg   1320
tctccacata ctgcacacac tacaaacttg gtacctttca tagtatgtaa gaagggagtt   1380
acccttagaa atgatggagt tttaggtgat attgctccaa cacttctttc cttgttagga   1440
ttgaagcagc ctgtcgaaat gactggtaaa gttcttgtta gttag                   1485
```

<210> SEQ ID NO 67
<211> LENGTH: 1152
<212> TYPE: DNA
<213> ORGANISM: Mycoplasma haemofelis

<400> SEQUENCE: 67

```
atgggtaaac ttgtaatttt tcacaaggag ttaaggccgg atctatcgtt ttttgaatcc     60
tttaatcata tagaaggagt ctacttttta agttctgact ttaagctata cagattcacc    120
gattccctat tagtattctt ccccccgtat agagtattta ataatcataa gatttttaaa    180
gctggggaag tatttgtaga ttgctctcaa gattcaaaag ataagtattg tagtttttcc    240
atttctccca agtccctttc catcccagac tgttacaaca tttctacaga ttccttgggg    300
gagttggatg ctctaataat agatttcgaa ggttctttta taaaggagtc atccttggtt    360
cgttactccc aaaggaagct acatttcatt agacatacgg aaataaatgt tcgttcttat    420
ttctatatag agaaagttaa gaagtacttg gtggataggg atttggcaat taatgtattc    480
gatagttttt ccatctccga aggatttaaa agctttgaaa gaatgcctgc tttgaggaac    540
```

```
tttaagagtt ctgggaatgc tgagctttca aaattcgacg atttaaatct ggatgttttt    600

gatttttgcg aaaggaagcc ggatacttcc tttaaggaag agtctttctt tgattctgat    660

gagaagatag acccctatta tttggagcaa ctatttaaag atccagagtt ctttaaggag    720

atagagaagg ctaagttatc gagaatagag gagacccata aaaatgatta tctatccaga    780

attgagaagg ccatcaggag gtcaagagct ctttccatat ctgttccaga gtacaactat    840

ccaacagctc cttttgattc cttcccagag aatttaaatt acctaaggga gattgagaat    900

ttcaatgaac aggaagaaag tgcctttaaa catatagact tatatacttc ctacgtctct    960

ccaatgccct tagggcgtgg agtttttatt tttagagatt tagaagagtt atttgatcca   1020

tataaaggaa ccataaatat tccggatata gaggatgaga tagagattat gaatgcatat   1080

attgatgaag ccttggactt ctatttcaag aaggagattt ctgaacctcc ttacttctcc   1140

tgagaagaat ag                                                       1152
```

<210> SEQ ID NO 68
<211> LENGTH: 162
<212> TYPE: DNA
<213> ORGANISM: Mycoplasma haemofelis

<400> SEQUENCE: 68

```
ttgctcgtcc tccataaact attcttctca ggagaagtaa ggaggttcag aaatctcctt     60

cttgaaatag aagtccaagg cttcatcaat atatgcattc ataatctcta tctcatcctc    120

tatatccgga atatttatgg ttcctttata tggatcaaat aa                       162
```

<210> SEQ ID NO 69
<211> LENGTH: 117
<212> TYPE: DNA
<213> ORGANISM: Mycoplasma haemofelis

<400> SEQUENCE: 69

```
gtgggaggca caaagacctc ctcttcctcc gcaacaggtt cctcctgttc ttctaacgac     60

tcctcttgaa ctatctcttg ctcgtcctcc ataaactatt cttctcagga gaagtaa       117
```

<210> SEQ ID NO 70
<211> LENGTH: 780
<212> TYPE: DNA
<213> ORGANISM: Mycoplasma haemofelis

<400> SEQUENCE: 70

```
atggaggacg agcaagagat agttcaagag gagtcgttag aagaacagga ggaacctgtt     60

gcggaggaag aggaggtctt tgtgcctccc actcttgagg aagtttatga taaatctcta    120

ttcgataatt tctccaacct attctacgtt agaacagccc ccccatctca cttcaattga    180

tttctgtccc cctttgttgt ccacgttttt gaattcttaa cttcccttag aagggatagg    240

gctatggttt ttagccatga agagaatttt gacagtcaac caattaggga taagtatcta    300

aaggacttat ccttcttgaa gagcattgag aagtatacgc atttccctcg attcgattac    360

ttcatctccc ccttttccta tgaatatgaa aagatgttct gaacctttac tccctataag    420

aagactatgt ttactatcca agacagctta ttcttcttga attcagagcc gtttgggccc    480

caaggaagat gtatgttctg agagtctcat gctttgaatc atccggaaga atgtcaagcc    540

tatataagga gaatagaaat tgaagttaag aataagtatt cagctttaaa cagggcttat    600

gaggtattca atagggattt atatggagaa tatgaggatg acttttcaat gctggactgt    660
```

-continued ccagatataa atttaggaaa gtttgataaa aaggctagaa aggaggcatc taagaaggtg 720
tgatatgaaa gtgaaccccc agaagcagag atagaaaggc accaagagcc taaaaagtag 780

<210> SEQ ID NO 71
<211> LENGTH: 600
<212> TYPE: DNA
<213> ORGANISM: Mycoplasma haemofelis

<400> SEQUENCE: 71
gtgtctttta agtcgtttat ttcggaagac gagaatgtaa ggtattttcg gttgggagat 60
gtgtgcaaaa tatatgcagg cattagcttc aagtctagct tttatagaga tagagggttt 120
cccattatta aaacgaggaa catccaagac aatcaaatag ttacaggtga cctaaattat 180
tgtgatttgg cgaaccataa ggatgccatg atcattaaac atggagatgt tgttatggct 240
aaagacggtt cttgctgtgg aaaaataggc attaacttaa ccgatgaaga attccttttt 300
gatagtcatg ttctgcagtt tattcctaat gagaagctgt taatcaaaag gtacctttat 360
catttcttgt tgagttgtca agataagatt cgagaattag cggttggatc tgcaattcca 420
gggattcgta aatcagaatt agagaagata aagattccag tttcctcttt ggaagttcag 480
gagaaggttg caagtacttt agataaattc agggagatcg aaagggagat aagtctccga 540
gataagcaat acgagtacta cagaaactat ctaattatgg gttctcacga tagtcattaa 600

<210> SEQ ID NO 72
<211> LENGTH: 159
<212> TYPE: DNA
<213> ORGANISM: Mycoplasma haemofelis

<400> SEQUENCE: 72
ttgtccatcc aagcagatat agcttctaaa ttaggtaaat ttcaggagct aaaagaggag 60
ctaaaagagg agctgttgtt gcgaaagaag aaacataatt attaccgaag acaaatttgg 120
aaaactcacc ttaacggcgt acagggttta aaattataa 159

<210> SEQ ID NO 73
<211> LENGTH: 435
<212> TYPE: DNA
<213> ORGANISM: Mycoplasma haemofelis

<400> SEQUENCE: 73
gtgtttaagg gttttctaaa ggctgaggtt agggagtttt tgttggagga tgtttgtaat 60
atacagaacg gctatagttt ttccagtagc aagtatagaa gtacagggca tccgattatt 120
agaataggaa acattcaagg aacacagttt aaagtagagg atttagtcta ctttgaacgc 180
gatgattaca aggaagatct aagtaggttc atcattaaac ctcaggactt ggtcataacc 240
gctagaggta gttgtggcaa ggtggctttg aataaaacag atagcagttt ctacttgaat 300
caaggggttt gaagattgga tccaaatccc ttgtttttaa atagggagta tctttttttat 360 tttttatcga actcagattt gagttcaatg gtaattaaag gacatattcc tcgcttgaat 420
gtcaactcaa tttaa 435

<210> SEQ ID NO 74
<211> LENGTH: 597
<212> TYPE: DNA
<213> ORGANISM: Mycoplasma haemofelis

<400> SEQUENCE: 74
gtgtcgttta agtctttcct ttctgaaagt aaggatgtga agcatcttaa gttaaaggat 60
gtatgtaaga taattgctgg aaagcgcttt actccttaca ccagcgaggg aatgcccgtt 120
ctgagatcgg gaaatatcat agatggctat gtggttgatg aggattttgt ttattgtgat 180
agagagaagc acccaagagt agatactgtt aagtatggag atattcttat agttagattt 240
ggtagcgcgg gagttgtagg aatgaacctg ataaacaggg aattcttctt agatgcgaat 300
ctatctaaat tttctccaga tagtaagatc cttcacaaac agtatcttta ccacttttta 360
ttaagtcgac aagaggaaat taaaggctga gctagaggtg cagtaattcc tgcaattagg 420
aagtcagatt tggaagaatt gatgattcca gtcccctcat tggagcagca acaaacaata 480
gcttctaagt tggataaact tgtggagtta aagcgggagt taatacttag aaaggaacaa 540
catagctact ataggaagca aatttgagaa gcctgttcta atggttgctc gaaatag 597

<210> SEQ ID NO 75
<211> LENGTH: 543
<212> TYPE: DNA
<213> ORGANISM: Mycoplasma haemofelis

<400> SEQUENCE: 75
atgtctcttc taactaagag tgctttagga ttcgctgcag ctggaactac tgccgcaggt 60
gcagcttatg ctggcggttt atttgatgga aaagagaagg agaagacatc tatatctaaa 120
ttacttcaga gtcttaaccc agagaagaga ttaataatgg cttcagaagg atctgatcct 180
ttatggaagg aagcttgaaa gaattacaaa gttaaatata gtggaaaggg attagatccc 240
ttgaaggtct tatctggaaa ggctcttgct tcggatgagt cggctccagc agatttcatg 300
tcatcatgta aagatttatt cgatgttaag gtggttgatg gaaaggatga tagctatcaa 360
ttagttctta atcactgcac tagattgact ctagtatctg attgaattgc agatagaggt 420
catgagttgg tttcacaaac agaaggggat gccaccattt gaaaggattt atggaagaag 480
tataaggacg ctggaaagaa tgcctgaagt gtgtcagagt atagttccta tcaagatggg 540
taa 543

<210> SEQ ID NO 76
<211> LENGTH: 681
<212> TYPE: DNA
<213> ORGANISM: Mycoplasma haemofelis

<400> SEQUENCE: 76
atgacacctt taactaaagc cgcttcggct acagcaattg ccggcactgc agccacagga 60
ggaatctatt taggtactga tttattcaaa gacaaaaagg tagaaattgc ttctttacta 120
aagaccgcgt atcccaataa acgtcttatc acttccaaga ctgtttcgga tgatgcttgg 180
aagaaggcct ataaagctta cagggaggca aataaggata agacaaagga catttgaagt 240
ttaaaggatt gaaccaaacc tcaagctacc gttgaagaga caaatgccac tgatgacttc 300
atttctaaat gcaattccaa cagtaaatta tcggtcgttg gaaaagatga ccccttgtac 360
aagcaagttt tagcttactg tactagggat actcttgtaa gtgatttaat ctcagaatat 420
ggaaagggga agaagttact aagcaaggac ggatctgatc aggatgcggc ttgaaaagcg 480
gcatggaatg tttacaagac gcgaaataaa gataagggag agaatcttga tccttggaaa 540
ttaaataatt ggaatactaa gaagtcggga gatgaattac ccgataacta caaagataag 600
tgtgttgaat attccaagaa ggcagcttac caattggaag atgagaatta caagaacgta 660
ttggattggt gtactgcata g 681

-continued

<210> SEQ ID NO 77
<211> LENGTH: 339
<212> TYPE: DNA
<213> ORGANISM: Mycoplasma haemofelis

<400> SEQUENCE: 77
gttggcgagg atacttggaa actaaaagga tgaactacta gatctaatga agctcaaatt 60
actgaagagg aagctccgcc ccactttatt caagcttgtt cagataatgg aaaggaggaa 120
ggatggaaga agacttggaa gctttataga gctaagaata aggatatagc tgctggccaa 180
gatacttgga aggttagtag ttgggatcca aaaacaacct cagatgacaa cgttgtggaa 240
gacttcaaga ctaagtgtac ttctaaatta gatcttaaat cctctgacag tagctttgac 300
gaggagtatc cgcgcgtcct tgagtgatgt actaaatag 339

<210> SEQ ID NO 78
<211> LENGTH: 693
<212> TYPE: DNA
<213> ORGANISM: Mycoplasma haemofelis

<400> SEQUENCE: 78
ttgagggata gttgggggga tatgactgct ttaactaaag ctgcttctgc gacggctgtt 60
gctggaactg cggccggagg aggaatttat tttggaacag atttgttgaa atccaaaaag 120
gtagatatct cttctttgat gaaagaggtt gatcctcaaa aacgctttat aaccgccaca 180
tcaacaggag acgattcttg aaaggctgcc tataagtctt atcgagaatc tggcaaagac 240
gtctggggtc tgggagttaa gactgcctct ccagaaacat taattgatgc tactacagaa 300
ttcctagcca aatgtaaatc taatggaaag gtgaaggttt ctgggaagga tgatcctctt 360
tataagcaag tcttagctta ttgcacaagg gacaccactg ttcgtgatct tatcgaggag 420
gggaaaacag gaaggaagct attagattct tcagacaccg gaaacgataa agagtctggc 480
tgggaagatg cttgaacagc ttacagaacc aagaatcacg tagaaggagg aactagtcag 540
aatacttggg aagtggaagg ttgagacaat aagaagactg gaaatactct tcctactgat 600
tacaaaacta agtgcgctga gaaggctaag caaccggctt accgattaga ggatgagaac 660
tataagaatg tgcttgcatg gtgtactaag tag 693

<210> SEQ ID NO 79
<211> LENGTH: 2844
<212> TYPE: DNA
<213> ORGANISM: Mycoplasma haemofelis

<400> SEQUENCE: 79
atgatcaata aaggtatagc ctttacaaca atcttcttaa gcggatccct ctatagcttt 60
ggttccttca tacatgactg acaagattat caatttcaac aggtagaagg atctggaatt 120
cttcaggata agagaagggg ttcatttctg aggggagaat tgccattcac tccctccttt 180
agggatcgat tggcaccttc acatatccaa aagactagct tccaacaaca taagcatctg 240
tttgctcctg agatgcagaa gtacctaaca gaggtaaatg aggaagatat aaaggaaggc 300
cattactcca gcaagaagaa ggagctgttg gatctgatcc attacaaaaa ggaatggatt 360
cttacttctg acaaggaaat atcatacaag tctgggtatt ttcaagagaa attaaataat 420
tttggagata acaaattagt tcaagacatt ctttggtctt tggttgagga atctcaagtt 480
aatgcaacat taataaggcc tgaatccatc accatcaatt tcaaaagaga gaaagttgga 540
tatcagaaga atccccttct tgataagtca gatgtcatta agaatctcca cattaagttc 600

-continued

```
cggatcttca atcccaaccg acaaaagacc tttgttttta aaagtataga gatcgatcct    660
acaagtgaga cagatgttga gataactctt agagagggag aattaaaacc agtttctact    720
gctctagctg ctctagctgc tcacaagtta agtgcatcgt cctgaagtat attcccaata    780
gaagaaggat ttaaagttac caaagaggta gtttacccca acaaagtcaa aactcaagag    840
cataaagata gtctcttctt actttataac tcctccagat tctttgagaa atgagttggt    900
aatcctagaa gtagatctgt ttcaacccac acccactctt tagtggatta tgagtatgtg    960
agaaagtcac tatctgctaa gttagtaaac ataactactg atcaagttaa gaaggacatt   1020
gagagatggt acggttcctt tactgcgttc attttaagaa cgaagattga ggacatgata   1080
aacctcatca acctccttca aaagaacacc ttctttgaca agcgtggtaa caaggtatcg   1140
gtagtagata atgctatcaa tgacttcacc ttcagacaca atctatacaa ccacttccaa   1200
ttcgattcca acttaagaaa agtcttagat accttgttct tacagaacaa gaacaaacct   1260
gagctgaaga ttactgttaa ggaggctaaa gctcttctta atagctgagt ttaccaacta   1320
gagcagataa aggactctat acgtatagag ttaaagtgag agaaagagcc acagaagacc   1380
aatgccgatc ttggatatga gaatatatat cccgcctttt catataagtt cacacagaaa   1440
tttgtcttta caaaggaggt aaagatccct ctaaagggga cttacaacac caccgaaaat   1500
aaatttgaag aagctactac ggagacggag aataaacaca agtttgatct atctaataga   1560
ctgaagaatg taaaggtatt cctaacccct ataagcttct tattcaatag tatgaatggc   1620
gggagtattg gaggagtaag catcatggat gtcttaattc ccgatgtggc gaactttgtg   1680
gatctagaat ctctaactat agatgctaat caggaaatca agaataccta cgagtctaaa   1740
aactccccaa ttaccctcgc tattgggggt gaggaagata tgcagaagat acacttccca   1800
ggaactaata tcggatggaa gtcattagac gtaactcaca gtcaagatct ttctaaattc   1860
acaaaactct tctacaaact ctatgagaag tttgatacct acaaggataa atcaaaccaa   1920
gcattagggg cattgcagtt attgaaggaa aattccagac ttaaagcaga tcctatttca   1980
tttatagcgc atgcaatcaa ttcactcttt gataaaaatt atcttcaaag caaggtaagc   2040
gaggagagta aacgtccatg acctgtattt ttcaattctt tactaggtaa acctctggat   2100
ttcaaaagta gacagttgtt aacgggactt tctagcttat ttttcgaatg agataaagaa   2160
tgagattcaa agtcggagga agacaaatgt gatggacaag gacaaggaca aggacaagag   2220
aaatattact gtactaagtt ctctttaaag aatagtagga agaagcagat tcttccaaac   2280
tcagaagaaa ccaagaacgt cacccagaaa ttcttcccaa catactcttc atatttccca   2340
gaaaagcctg ttgtatttgg aacaacggat gacacaacag catacgatgc tttcttagcc   2400
aaagaaggta agagctctat agggttggtg aataactaca ccaaactgaa ggaggtattc   2460
aagtctagat ttgaaaagga tcctaacttc tttccgtcca acaaagagat caattgaaat   2520
aacgcgaaag tatcttacgt taggttggat ctagaaaagg caattaaatc tgtgctagct   2580
ttggagaata ccgcatatgg aggtttaggt ttaatggtgt ctgcggtagg tatagagttc   2640
cacaaaattc taggtgaagc tctagttaga gatggattct gaataaatat gaatctaatg   2700
gatgaaaaag gctctttctg aacaatagaa catccaataa agcacatgtt ctattctccg   2760
tttagtgaga gttgattgtt cgtgaaaccg gacttggatc atacaaaatt agaattggga   2820
acattttcga caaagcggaa ataa                                          2844
```

<210> SEQ ID NO 80

<211> LENGTH: 2739
<212> TYPE: DNA
<213> ORGANISM: Mycoplasma haemofelis

<400> SEQUENCE: 80
gtgttcttca tattgcctag ccgacggaag ctggcaattg gagctggagg gatcttcttt 60
gcatcaggtt ttatttattt tagagttgca gaaaaagaac catttgaaaa gatagaagga 120
tcccttcccc ttagaaacaa gaacaaatta aattttcagg ataaacaact atcccttcag 180
ggcttcttaa aacaagatca cctatattcc cagaactatc aggtatttga tccatctata 240
agaaaatatc tagagatacc catatccccc agaagagtag aagaatctgg gaatctattt 300
aaggccttca atagccttaa aggttgaaat agaacggcat caactatctc agatagggat 360
ttaagctata gagataatcc cttcataggg ggagttaact ctcttaagaa ggaagaaata 420
attagagata ttcttgagtc aatacttgat gagtcagaat atctctccac tttaataaga 480
gccgactcta taaagataga gttcaaaaag gaagagggat tttctttagt taaggacttt 540
aatttaagac ttagaattct taatccccgt aagagaaagg cctatttatt caaatccata 600
gagatagatc ccctaagtga gaacgatata catatatccc tctcgcaaag tgaaataaag 660
cccactactg tttccgttaa cttggggcat agtaaacaga tttcatgatc tctattccct 720
aaggactcgg catgaaagat aactaagatt acccattccc ctaatcatag aaagactgaa 780
gaaactaagt tctctctacc cctaatatat ggaacaagcg ccgcattaaa ggatctacaa 840
gagcttcttc cgagaaagga agtagatcac cccttcccaa tagcaagctc cttagactat 900
ggatatgtaa gagagaagtt gactcccctt ttggtcaaca ttagtgaaaa tcagatggag 960
aaggatattg aggcgtgatt tggggcacat aaagcccatc aaattagagt ctacatctct 1020
gatttacaaa acttaataga gatgtttaag aagaggagtt tcttggacaa gaatggccgt 1080
aaagcttctc ttatagaaat ggttatgaaa agccatacct tcaaagatgg cctatataac 1140
cacatgaaat tgagtagctc atacagaaag gttctggatt ccctcttaac tagtgagggc 1200
aaggaactaa agctaactga agaggaatgc tatgctcttc tagatagttg atcctatcaa 1260
ctaaagcaaa tgcaggactc cataaagata tccatcactt gagatgagaa gcccaagaga 1320
gttattcaac ctttgggata tacatccccc tatcctgcag tctcttttaa atttaagcaa 1380
aagatatctt tcgagaaggc tgtgaagatc cccttaaacg ggagctgaga ttcttcacaa 1440
aagaaatatg atgcttcttc tggagatcaa aagtttgata tcaccaaaag actatctagc 1500
ttaggaacta ttcttgctcc aataagatcc gtattcaaag aaatggggaa tggaggtagt 1560
ttcatggggg cagatatatt tgatgtattg atgccagatg tctctcaatt ccttggaata 1620
gatggcctag agatagacgc gaatgaatac atagagaata tatatgaagc ttctaactct 1680
cccattggga tagctatagg ggactctgaa gactatcagg gtataaatat aaagggcaag 1740
aatataggtt gaaaagctct tgatgtatct agcagcatca atttagccaa cttctctaag 1800
ttcttctaca agctatatga aaagatagat acctataaag atccttccaa ttctgcattg 1860
ggagtatctc aattatggaa cttcacaact cttctacaac aaagaccaat ctccttcata 1920
atacatgcca ttcactccac ttttgatcac caatatctaa agagcggaaa ctccacttcc 1980
gaagataaga gaccctgacc tgtattcttt aaatccctat ttcaagatcc tataactctt 2040
aaacataagc aagtattcgt aggatatagt ggggctttct ttgatgtaaa ggaatgattc 2100
cgtagtgaaa ctaaatcaag tgagcaatac tctacctcat gagatatctc taccaagaag 2160
caaagggatg agtgagagat actctcccct aagaatgagg atgtagcttt aataaatcag 2220
aaattcgcac ttaactactc atccttctct cctgagcaac caataatcat taattccgaa 2280
gaaaataaga gtcaatacga tgccttcttg gccaaagaag gaagtaccag tataggatta 2340
gtaaatcact acgatcgtct taaatctgta ttcagagata ataacaagag caatatttac 2400
tatcccaata tagattggga aaatatgaaa gtctcctatg cccagttaaa tctcgagaag 2460
gcaattaaat cagtattggc cataaggcat accttccaag gattctcatc tttaacctta 2520
acagcattag gaatagaaat ccacaagata cttggggagg cactaataag gaatccattc 2580
tgaataaata tgaacttcat gaaggaaata ggatcttgat ccaagaatga aattcccttt 2640
aaatatatga gctactcagt ttacagtgag gaatccctat atataactcc acagctagat 2700
aagacaaagc taaatctagg tagattcatt aagctttag 2739

<210> SEQ ID NO 81
<211> LENGTH: 1125
<212> TYPE: DNA
<213> ORGANISM: Mycoplasma haemofelis

<400> SEQUENCE: 81
atggatggac aggaaaaggg taagaaagat atagcaaatg atcccgaagt tagaaaagag 60
ttagaggctt acgaaaagta catacttcaa cagaagcatg agatcttcaa taggataatt 120
ttaaatgcaa tacatacttt aaagattcag cagccaataa ttagttgttg caagagaata 180
gacctttctt ccctcccagg ttttaacgaa gaaactatag gacagttact aggtaaagac 240
ggacagcata agcagcattt tataaatctg acgaaggtag atttacaagt cgatcagaag 300
tgccctaatc atggaatagt actatctaag tacaattccg taaatgttga gaaggctgta 360
gagttagtga agaagctctt ggagcttaag tcatggaatt tagagaagat gaaaagcctt 420
tatgaaaagg taaataagga gtttgaagat aaatgtaaca agattggagg gcaatgactg 480
gagcagttct tagggtatga gaactatcca gacttcttgg caactcatgt gggaactctt 540
caatttgtat actccttcag tcagaacata ctcgagcata gtatagaggt agctcaactc 600
tctgccaata tagcctttca attaggatta gatcctttga aagctaaaag agccggtttt 660
ttccatgaca ttgggaaggc taaagccaac ttgggagatc atgtagatga gggtttaaaa 720
atagggcaag aagccaattt cgaggaatat atacttaatg ccattgaatc ccaccatgga 780
cgagtccctc ctaataatcc ttactccatc atagtcaaag cagcagataa gttatctgct 840
gggagggaag gagcacgtcc aaggcagata gaacttatag ataagaggag gaagatgatt 900
gaggataaga taatgagtat cccatggata gaaaagacaa taattaagaa tgctggtaat 960
ttaattcaga tctttattaa gcctgcagaa ttccacgggg ataagattct cgagatgaag 1020
gaggaagtta gagctaagtt aaaggagcta aaggcagaat attcttacaa ctatcaaata 1080
gagtttcact tagtgttcaa agaggaattt aaattttctg aataa 1125

<210> SEQ ID NO 82
<211> LENGTH: 660
<212> TYPE: DNA
<213> ORGANISM: Mycoplasma haemofelis

<400> SEQUENCE: 82
gtgagctcgt attctattat ttttgagaat aaaaattttt taatagtcaa taaagcctct 60
ggaattgccg ttcataagaa tatctatgac agggaattta atctcattaa tgaggtaaat 120
aaagaccaga aagcaaacta ctctctagtt catagaatcg acaagtacac ctcgggcgct 180

-continued

```
gtacttattg ctaaaaataa ggaaaccctg ttgcttctac agaatctatt cctaaacaat    240

gaagttgaga agcattactt agctctcact tccaaggaat tgcctgctaa gaaacttaag    300

ataactctat ccttagggag aagcaagaac gataaacttc gctttactaa taggaatgct    360

aagaactata aacccgcctg tactgaggtg gaggttatag accgctactt cttaaagatt    420

ctactaaaaa ccggaagaac tcatcaaatt agagcccact tattctccat aaattgtcca    480

gtcttgaatg atccaatata tggcaatcga tgtttcaatc ctgagtttgg acaatatcta    540

cacgcctata aattagagtt tacttgtccc attaccaacg agttcatatc tgttactgcc    600

ccattacctc aggaattcaa agataagcta tccgaactta atattgaata cacagaatag    660
```

<210> SEQ ID NO 83
<211> LENGTH: 609
<212> TYPE: DNA
<213> ORGANISM: Mycoplasma haemofelis

<400> SEQUENCE: 83

```
atggctctag caggagctac tggtgcagcc ggaggaggcg ttcttgtcca taaactcata     60

aataaagggg aggacacaaa gtccaacacc atctctaatc acattaagcc tgaatatcta    120

ttaactaata ctcatgcaag tcaatgaact catagattaa atctgctagg taaagcgcag    180

gagacagact tatctgaagc cttactctcc tttaagaaag ggaaatcttc tctaactaca    240

gaggacttaa agggatgatg tgaatcgagt ttgaaatcgg agtttaagag caaggaagat    300

aagaagtttt taaatactag actttactgt ggcttgaata tgggagatag tattcaggaa    360

aataaggtgt cttcaaccac agagaacggg aacacaggct taaagtccca gtttgaaaaa    420

ctaaaaacca agaaagttac ggaattggtt tcagcattat tcgccattaa ggacaaaaac    480

aatgccgata gttcttgaga agggaacgta gctcttaaag attgatgtac taaagctctt    540

gatatgccta tggaagaggg attaacttat gataatgcca aagaatattg cgttctaact    600

gctagctaa                                                            609
```

<210> SEQ ID NO 84
<211> LENGTH: 123
<212> TYPE: DNA
<213> ORGANISM: Mycoplasma haemofelis

<400> SEQUENCE: 84

```
gtggctgctg ttccggtagc cgcaaatgca cctaaccctt ttaaaagtga tgttttcatg     60

acaaaaaggg tggacaaata taagactcct aaattaccat gtaagccttt tcatctctat    120

taa                                                                  123
```

<210> SEQ ID NO 85
<211> LENGTH: 867
<212> TYPE: DNA
<213> ORGANISM: Mycoplasma haemofelis

<400> SEQUENCE: 85

```
atgaaaacat cacttttaaa agggttaggt gcatttgcgg ctaccggaac agcagccaca     60

ggtggctttg tcgcttggaa gcaagctact aaacctacag atgttaagag tagattggtt    120

tgagaagggt tgacagttgc tgacgtaaat ggaaagggag tatggggggc tatctattta    180

gccaagaagg atgtctctgg atttttggat tttgcaacca ccaaggataa taaggaaact    240

gcgtcagctc aactgaagaa gaagtgttct gaattgttta atgtgtctgc cggtgatgag    300

aaatatgaag agtcttatga gaaggcgaag aagtgatgtt taaatcctga gttaacaacc    360
```

attgaaattc aatttgagtt tgaagatagg gaatttgctt ctggggatga tgactttaag 420
aacttattta ccttatacaa gggaacttcc agttttgtgg atgttgtaaa gacatctgct 480
agagacttca cagctcaaac cgctcttgaa acagctaagg gtaatgtgca aacgtgatgt 540
aactctatga aatcaaaatc cccaaaagga gatgacttaa agaatgctat ctcttggtgc 600
actaaaccgg agtctaactt taaatcattt atggagaaga agggatttcg gttgcttgcg 660
gatggagaat gagggaatca tttttcaagt ttgaaatcta agggcggaga tactgcttta 720
gatggtgata ttaaaagcga aaccggaagc gatgatggaa gcaagttaaa gagttggtgt 780
gataagaaga acgtaggaac ggttcagata catactttga gtgcagattt agaaaagata 840
gaaggtaggt gttttgttag gaagtaa 867

<210> SEQ ID NO 86
<211> LENGTH: 744
<212> TYPE: DNA
<213> ORGANISM: Mycoplasma haemofelis

<400> SEQUENCE: 86
ttgatttggg atggtttatc tgttgcagat agtaagtcct taggggtata taaagctatt 60
tatctggcta atagcgataa ggccggattc tcttcttttg taagtgctag tgataaagag 120
aaagctgctc cacttttgaa gaccaaatgt gatgacttat tgggcataag tgcttcttcc 180
gataagtatg cccagtcttt ggaagaagct aagaagtggt gtttagttcc caaaaagaca 240
accatagaga ttagtcttct tgtggatggt atggagcttt cgtctgcaga cgatgattac 300
aagaacacct ttgctttaag cagatctagt caagacttta taaatgccat caagaagggt 360
agtgatggct tgaccactag ttctgatgtt aatactggat tttcgaaagt taaagagtgg 420
tgtgcagagg taattaagaa atctgcattt gataaagatg cacagaatgc caagttgtga 480
tgcgttaagc cagattctaa gcttggcgat ttcatggata aacaaggatt taagccggtt 540
gaatcaacgg gttgagattc tcactttact tctttaagct cagataatac tttgacatcc 600
gatatgtctt ccgtgtccgg aactgaaggc aatggaaata agttgaagtc ttgatgtgaa 660
ggtaaaaatc tagcgaatgt tcagatacat actctgttaa ctgatttgga gaagattaag 720
agtaggtgct ttgttaggaa ataa 744

<210> SEQ ID NO 87
<211> LENGTH: 855
<212> TYPE: DNA
<213> ORGANISM: Mycoplasma haemofelis

<400> SEQUENCE: 87
atgagctcag ctttagttaa agggcttgct ggagtttctg ctgttggggg agtttcggcg 60
ggaggattct ttgcttacaa aaactttcag tcacagaata ttagggatgt tctggtaggt 120
aaaggattga ctgttgctaa tgttaattct gttggtgctt gaaaggtgat tgccatgggc 180
aataaggata atgatgcttt ctttaccttc ttaggaataa ctaagacttc cgataggaaa 240
gttgctggct ctaaattaca ggagaggtgt ggaagtattt tgaatgcctc aattaaggat 300
gagaattatt ccagcttgct ttccaaggct gaatcgtggt gtattcagcc tactcctaag 360
aatttagaag agcaattatt aatggatgag ttggagactg acttgtccga tgatgatttt 420
aagaatgttc ataagatact agctcaggat aaggctttta cagatgctat agaggttact 480
aaagggactg aaagtgatgg ctataagaag gttaagaaat gatgtgaagt agagttgaag 540

```
aagcctgcca actctcccaa agatgccgct aaatctagat gtgctactcc attcaagaac    600

cttagagagg ctttaaatag tggcggactt agtttaattt cctctgcaga agattggagt    660

agcaggtatt caagtattaa gggtacggat acttctctaa gtagtgatca gataactgat    720

tctgatggga agggaggaac gtctctaagt acttgatgct ctacagaggt ggataagaag    780

atacatgagc ttactagcaa ctatacagag cacttagata aagttaagaa gcgctgcgta    840

acggttaaac tttaa                                                     855


<210> SEQ ID NO 88
<211> LENGTH: 603
<212> TYPE: DNA
<213> ORGANISM: Mycoplasma haemofelis

<400> SEQUENCE: 88

ttgaatctaa atttggaggg taaagcctct aagttagctt ggggtttggg aattgtgggc     60

tccctagttc ttattatttc ctctatttat tgaatttctc caactgtaca agattcccta    120

gaagatcaag aacttcagtt aatttctaaa tcgaatgaaa gtatagatct ctataagaga    180

tccttcaaaa ggcataagaa cactcttata tctattggtg tggatgattt tataaatgag    240

aatactgttg aagatgaggg atccgttgcc cttcatattt gatgtgatgc taacttaaga    300

agtaagcgtt gattggtgaa tttagatgga tataagaggt tctgtgccct ttctatggga    360

gatgttttgt ggctagataa gaaggatgag ggattattta attcacatag gttttttata    420

ttggaggaag aagataaaag atttagtagt aggctattct ctaagtttgg attaacttgg    480

aaaaatgaca agcacataga taactatgag atttgaaaga gtaggtgtga atctgagcta    540

tctgaacctt attcttattt aaataagcat ttaaagacgg atatcaagga taactgcttt    600

taa                                                                  603


<210> SEQ ID NO 89
<211> LENGTH: 609
<212> TYPE: DNA
<213> ORGANISM: Mycoplasma haemofelis

<400> SEQUENCE: 89

atgaatacct tagctaaagg agctattgca ctaactggag ccggaggggc tgctgggggc     60

ggttttctaa tatctcagaa tttaggcaaa acagacacta ttgccaatca tataaagaaa    120

gaatacctat taacatcgga gcagactgac aaatggaatc atagagttgg tcttcttaag    180

aaagctcagg agggaggtct tgattccagc ttactccctc taaagaaaga gggcttaact    240

aatagtgaac ttcaaacttg atgtgctaac cagttgaagg agaagtttga aggtctgggg    300

agtaataaat ttctaaatgt gagactctat tgtggattga acatgggcaa taagattgct    360

ggtaataagg tatcctctag cacctccgat agcgaaaata aattagctac taacttcggt    420

aaattgaatg gcaaaactga gcaagagttg ggaagtgcct tgcttgaaat tggaaagaag    480

acaaatcaat caagtggatg ggaagggaat aaggctttga aagagtgatg ccttaaaacg    540

tttgatctag cttttgagga aacttcaaaa gattacgcaa acgctaagac ttactgcgta    600

ctagtttag                                                            609


<210> SEQ ID NO 90
<211> LENGTH: 618
<212> TYPE: DNA
<213> ORGANISM: Mycoplasma haemofelis

<400> SEQUENCE: 90
```

```
atggaaataa gcggcttatt taaggcattt ctagctttgg ctggagttac gggagctgct     60

gggggtggag ttcttttaca taaggtaata aacaaagata ccatatccaa gcatatagat    120

cccaagaacc tcttaacctc tgcacaacaa gataagtgaa cccataggtt aggcttgctt    180

aataaagctg cagatacaga tttatcaaag gacttactct ccgcaaagaa aagcaaaact    240

accttgacta tagatgacct aaagtcatga tgtgcaagta atttagagtc tgaatttcta    300

ggtacaaagg ataagaaatt taagaatata aagctctact gtggactgaa tatgggagat    360

aagatacaag gaactaaagt agcttccact acagggggag ataattccag tcttaagact    420

aattttggaa aactaaagaa taagacgagt tcggaattgg tttcccaatt attctccatc    480

cggaacgcag acaataccaa tagcccctga agtggaagca catctcttag agattgatgt    540

ctttcagctt ttgacatgcc atttgaatct ggattgactt acgacaatgc caaagactat    600

tgtgtaatta ctgattaa                                                  618
```

<210> SEQ ID NO 91
<211> LENGTH: 864
<212> TYPE: DNA
<213> ORGANISM: Mycoplasma haemofelis

<400> SEQUENCE: 91

```
atgagcgcta aaacaacact tttaaaagga ttgggggctt cggcaacagc tggaacagtt     60

gctactggag gattcttcgc ttgaaagggt ctttctcaga catctgatat tactagtcgt    120

cttacagggg aaggattgag tgttgcagat gtaaataaga aagggccgtg aagggtcatc    180

tatttaacga agaaggatgt tgagggattc tcggattttg tggacgcttc tgatcaggag    240

aatgcagttt ctcaattgca gaaaaagtgt tctgaattac taagtgcatc tccacaggat    300

gagaattatg aaaagtccta tgagcaggtt aagaagtggt gtgtaaatcc agagttgaaa    360

acgattgaaa tgcaatttgt atttgatgaa cgagaatgag ccgctgcagg agatgacttt    420

aagagcttat ttacgttaca tcagaatgat ggcaacttca ttaatgctgt ccagtcctct    480

acaggcttct tcaatgcaag catggtttta gatgaagcaa agacggaagt tgaaacatgg    540

tgtaattcct taaagtcaaa gactccagag ggagatgatt tgcaaaatgc cgtgtcttga    600

tgcactaaac cagaatctaa tttcaagtcg tttatggata agaagggatt caggatgttg    660

aatgaatcag aatgagcttc cagattttct tctttaaagg gtggacaaga ttctgattta    720

tctactgatg tgagtgatga tgatagtgat ggaagtaaat tgaagggttg atgtgagggt    780

aagaaattag atactgttca gatacatact ctggggtcag atcttaataa gatagaagct    840

agatgctttg ttaaaaagga atag                                           864
```

<210> SEQ ID NO 92
<211> LENGTH: 645
<212> TYPE: DNA
<213> ORGANISM: Mycoplasma haemofelis

<400> SEQUENCE: 92

```
atggagttat cttttgctgc caaaatgtct actggagcaa taggagcagg ctctattgct     60

ggaggaggag cttttgcggc ttataagttt cttaatcagg aaacaataga gaagtatttg    120

aactccttgc atcgagagtt agctacttcc aatgaggatt gagaattaat aaagaataat    180

tacgcagcag ataaagagga caatccaata cctaacatcc ccaaagcttc cattggagat    240

aaattaaacg atcttaagaa gtgatgtagt gatcatttaa atgaagaatt ctcccaagag    300
```

-continued aaggcaagta aaggagatta caacctaatc caatcttgat gcaccaaaca agtaaaaata 360
tcatcttacc taaagcacct aaaacttgaa gctctagaaa ctatcggaac caaagataat 420
gagagatgaa caaaattaaa ggattcctat ccaaatggca gcttgaaggt gcatgaaata 480
aatacttccg gcaacactaa atccgaagga aacgcagtag ataacttatc tggaagtgat 540
caaaagataa aggattgatg ttcttgagct tccgatcaat actttagata caaagaagat 600
accctattta aaagatacga atacttctgt actaagcccg cttaa 645

<210> SEQ ID NO 93
<211> LENGTH: 648
<212> TYPE: DNA
<213> ORGANISM: Mycoplasma haemofelis

<400> SEQUENCE: 93
atggtatcta aggctggagt agctgctgtt ggggcgttgg gggcaggaac tgcttcctat 60
atgggctatg aatacgtatt taactctaaa gaggaagtga agaaaactac gataagggag 120
aggttgggag atcttctgct tgatacttca tcgtcagata aatgggctgc taggaagact 180
aagctttctc aagccgagga tacttctttg gttgaggagt taaagtcttt gaagaacggg 240
gtaagcgagg atcaagttaa gggttgatgt tctggggcgg caaccaagac ttatgaagat 300
gtgagtgctt tgtatttcga gaatgtcaga acttattgta ccttttatat tgaagataag 360
ttgcctgagg ggtatattac gaaagattct caagattgga gcaaagcaag tgatcgtctt 420
aagaatgtac aaaccggagt tgccttatct gatcaaatga aggctattaa ggataaatta 480
acaactcaag gatcatcagg aaccaatgat gacttaaaga attggtgtgt aggtgtttat 540
gagaagcctt tcttagggga agataatcag gactttgtag atgctaaggt ttactgcgct 600
aagatagaga cgacttccac aggatcagta tctccagctg cagcttaa 648

<210> SEQ ID NO 94
<211> LENGTH: 594
<212> TYPE: DNA
<213> ORGANISM: Mycoplasma haemofelis

<400> SEQUENCE: 94
atgttaatgc tcggagtagc tggaactacc ggcacagcgg gacttggttt tctaattgcc 60
aagaatcaaa aggatgaatc tcagaagtta agaagtaagt atccacacgc cttattaact 120
ctggatagtg acagttcttg gagcgataaa ttcaatcttc taaagaccaa aactccgtct 180
catccaattc tcaaacaagc aaaaacacag ttttccaata ctcagcaatc tcaatctctc 240
tacaagaaag gatgcaacgc tatttatgac tctgaaggaa ctcaatattt ggaagacttc 300
aagactttct gcgcaaagac caataaagat ggaattactg gcacttgaat aaagggtggt 360
gctgatgtga atactaagtg ggatgaaaag cttactaact taaagaaaag cacagacaag 420
ttaagctcta gatttctaga ggtacaacaa tccttaagtt ctgatagctt taacgatgag 480
atgcgaacca acatacagaa agcatgcgat aatgcaaatt ccgaaattta tctaggctct 540
gaatctgtgg aaactaggaa tattaaaaac ttctgcttaa cgtccgaaag ctaa 594

<210> SEQ ID NO 95
<211> LENGTH: 603
<212> TYPE: DNA
<213> ORGANISM: Mycoplasma haemofelis

<400> SEQUENCE: 95
atgaatccag aaatgatgaa gggggcttac gccttgggtg ctgcttccgc tataggtgga 60
ggagctttca ccgctaagta catatatgac cgatcatcat ccatttcaat tgaaagccat 120
ttgaaatcta agaatctaac cgtaatctcc tccctcaata gcacttccca atgggaggaa 180
gaatacaagt tagataagga tgccataaag gcagaaatcc aaatcaccaa tgacaatgaa 240
ggcggaacta aattaaagga atgatgctcc caacagctct ccaagccctt taaagaggga 300
gaggatttat cgaagataga aaggtgatgt accgttggaa agatatctca aagaattcct 360
aagggaaaag agctcttaca ggatggagct gaaagctctg aatgagaaaa actctacaac 420
aagaatactg atcaaagtga aaggagtaag ctctctttgg caagtagcaa agaagatgga 480
actaagaata gcgatttaac tgcaatcaag aaattttgct ccgacaataa agacaagcct 540
ttcttggccg atagaaaagc aaccgaatac gatctagtta tcttgtgatg tattaagcaa 600
tag 603

<210> SEQ ID NO 96
<211> LENGTH: 1428
<212> TYPE: DNA
<213> ORGANISM: Mycoplasma haemofelis

<400> SEQUENCE: 96
atgtcgtgtt cttgtgaaaa gccttctgtt tcaaatgtac acctagattt agggtattgg 60
ttccaagtat actctgcata ttttaggtat tttttaatta aaggccgtat aggggaggat 120
actttcgaat cttttatcaa gaaatttgaa tctttaggtc tcaaatttgg gtgtgaagct 180
agtctggatt ttaaatcttt aaatagagaa ttagattccg aattatctcc ggaagagaga 240
gatcttcttt ctcaaataaa tgaggttgag gctaccgaag cagcagagaa gttagctatt 300
aaagatatat gtgattacca agttcgtgac ttttacgatc acctgaataa cttcaagaag 360
ctagcttttg actttcgata tctatcagag aattcagatt cgtctaatcc cttaggaatt 420
caattctcca tctatttcaa agacctgcaa ttgcttgtag ataaatttca atccaataga 480
agattcgtag agagctttaa ctttgaaact gatatcaatg gatctgactc ttttgaaatc 540
cttaacttcc taactagaga actggatctt ttcccagttc aattccaaag ctattcttcc 600
tgcaattgat tcttcctcgc tattagagaa ctagctagat ttgcaagaga agtggctggc 660
tttgttcaac tgcacggatt ttctctttcc ttgggtgata tggacgaata cttgttatcg 720
aatgttattg aggcgtgtga tagagtggag aagaattcag agaatgtttc ttgctctttg 780
gagtccttca agatcatgat gattgatatc agtaatctat tctctaactt aaataaggtg 840
tgtttaaata taaagcccga tgaagagttt tgaaaaccgt gtgaatccaa tgagcattta 900
gactccttat atctgaagat atttagcccc catctgttgg aagaaaattt gaattacata 960
ttcctgaatg agcccgagat caggaatata gtaaataagc tctcttccaa aataaacgaa 1020
gggtgtgcgc accatgggga tccagtgtgt ttaatttttg agcaaaggga atccattccg 1080
ttcataggac aactccttcc ctatttggat tttccatgca cattggttcc ccttgaggat 1140
ctaagtaaag aatccgtaga gaggtgcgag ggggttttag atggcagaaa agctatattc 1200
ctaggaactc tcttgagaga agctagctat atagacaaga ttaaagagag cataatgaag 1260
gaggatctga agattggatt cctattcgtt tttgattctc tagcttccac ccctatagat 1320
atagatttct taggagaatg tattcctgat gaggattggg taggatttgg tctgggatcc 1380
aaacataagt gttgtaattt aaatgccatt ggagttttaa gggaataa 1428

<210> SEQ ID NO 97

<211> LENGTH: 705
<212> TYPE: DNA
<213> ORGANISM: Mycoplasma haemofelis

<400> SEQUENCE: 97
atgcataacg atatcagagt tcaccttaag tacctagcag aaattctaaa ggatacctta 60
aataagatgg tttttatggg gaaaatagaa tttcccaaga aactggaggc ttacgcgaat 120
ttatgaaaag aggaatttaa agatcccttc accatcccct taactgaagc ggagtgacaa 180
gatattaaag ggatagctcc ccaattcagg ggaaataggg agcttcaaag ttcaataaag 240
aatgtcaaaa gaactttgga aagacagcaa ttcagaaatc tttctattct taatttaatg 300
gatgagaaat tgaatctata catgcacata ttggagacca ataggcagtt atcccttctt 360
acaagatcat ctcaagatga ggtggcctat atttctaagg acttcaagaa gagaaggtta 420
atgggttgtc aatatataca tagggaagta aagaacgtta caaagctaac taagaagcat 480
gtgatagtga atgatatagg gagctatata aatatgttcg tggacttctc cgttaaggaa 540
ctggagcact taacccactt cataaagata attagaggga ttgtggatga gacaattgtg 600
ggagagaaat tggctctttt gaaaacaaga atcagggaag gaagctttga cttgccatcc 660
ttcagacaat atatgaaact agagtcctcc gtgaataaga agtaa 705

<210> SEQ ID NO 98
<211> LENGTH: 3080
<212> TYPE: DNA
<213> ORGANISM: Mycoplasma haemofelis

<400> SEQUENCE: 98
atggcaagga ggagttctag tgcttttaaa tcacaaagca gtcctaatga tttcaccatt 60
aaggctttac agatctcttt agcttctccg gagtacgtaa gatctctatc taagggtgaa 120
gttacttctt ttgaaaccat taactataag tctctaaggc cagagaaggg agggttattc 180
tgtgaaagta tttttgggcc tatcaaggat tatgagtgtt cttgtggtaa atataagcag 240
gtaaagtaca agggtaagaa atgtgagaag tgtaaggtat acatcaccca gtccttagtg 300
cgtcgtgact ggatgggtca catagaattg gcttgtccgg ttgctcacat ctggatgata 360
aaggagcttc ctcttcctgc caaaatctcc cttatattag gtattaagta caagcacgta 420
gaagaggttg tttactttgt aaactacata gttttagatc cggggcatct tcaagtagag 480
ggtaagactt tatttgatcc ccttgaaatc atagatgttt ccaactccaa gagttctatc 540
gcttcacttg ctaaattaag aactcttctt agaactatat acgagactat tcagaaggag 600
aatccggagt cctacttaac tgacttaaat taccaacaag gtagagcata ttataaagcc 660
ctttctaact caaacttgcc attctccatc atggacatgt ttgagtatat tgagaaacac 720
acagggctta aagttgggat aggtgcggaa gcaatttacg aacttcttaa gaaggttgat 780
cttgaaagtt tggaatataa attgactcag gagcttaatg taaacttccc tagtggtctg 840
aattatgcag atcctaaggt tagaaagatt ctttcaagac ttcaggttat tagatggttc 900
aaggaatcca agaatagacc agagtggatg atcttaaagg ttatccccgt tatacctcct 960
aatcttcgtc ctattattca actttccggt ggtagattta cgtcttctga tatcaacacc 1020
ttttatagaa gaattattgt tagaaatgac aggcttgcca gaattctgaa ctttaatgtt 1080
gcgcatatca tctccaataa tgaaaagaga atgttgcaag aggctgtgga ctccttgatt 1140
gataactcca gtagaaagaa acctttaact gctagggata gacatcctct taaatctatt 1200
acagatcatc ttaaaggtaa gcaaggtctc ttccgtcaaa accttttagg taagagggtt 1260

```
gactattccg gtcgttccgt tattgttgta gggtctgaac tgaaaatgta tcaggtaggg   1320
ttgcctatcc tgatgattct gtctctattt aagccattta ttattaggga cttaattaga   1380
aaggttgatg acaatggagt tgaatgtgtt cctattgcag ccaatattaa gaccgcttct   1440
aagatgatta tggagcagtc tgatgaaatc tgaccagttg ttcacaaggt tataaaagaa   1500
aggccagttc ttctaaaccg tgctcctact cttcaccgtt taagtattca agcttttgag   1560
cctatccttg ttgaaggtaa ggctatctgc ttacaccctc ttgttacaac cgcctttaac   1620
gctgacttcg acggtgacca aatggctgtt cacttacctc tgtctgctga agcggttcat   1680
gaggcgagat ctatgttatt ggctccttga caaattcttg gccctaagga tggtaagcct   1740
attgttactc catcccaaga tatggtgttg ggtatctatc acttaactac tgaggacaag   1800
gaagctattg gttttgggtc tttatttgca actcccgatg aagttgttca tgcttaccaa   1860
ctaggtaaag ttgatctgtc ttctattatt gcgattggga cttctggttt tcctaagaag   1920
agatttccaa aatcaggtat cttgatcacc actgtaggga agatcatatt caacagtagg   1980
ctcccagagg attacaagtt tattaatcaa agtgaaggga tgtgggtgtc agagaatgat   2040
atcttggatt acggagtaag taggttggat tacattaatg cttatcaaga gaaggagcca   2100
ttcgcaaagt ctgttattgg tagattgata gaggatcttt atgacaacta ttcttgtcaa   2160
gatttagctc cggttctgga ctccattaaa gatatggggt ttgagtattc caccaagtcc   2220
tgtacaacta tttccgcttt cgatgttcct aagttctccg ataagcaatc cctcctagaa   2280
gaggctgata agttagttga gcaacagaaa tccttcttta ggaagggtct tgtcactgac   2340
gatgagaaat ataagaacgt tattgccatt tggtcttccg ttaaggacaa ggtttctgat   2400
cacattaaga atgctcttaa atctaaggaa tttcaaagta accctattgt tatcatggcc   2460
agatctggtg ctaggggtaa tgtatctaac tttattcagc tatccggaat gaggggtctg   2520
atgaacaagt cctataacta tgaccagaat acaaatacca aggtagttag ggatattatt   2580
gaggttccta ttaagcactc cttcattgaa gggcttacag ttattgaata ctttaactcc   2640
tcctatggtg ccagaaaagg tatgaccgat accgccatga aaacagctaa atctggttat   2700
acaactagga agttggtgga tgctgctcaa gaggttattg ttaaggttga ggactgtgga   2760
tccaataagg gattgattgt tgaagagctt agagataagg agcattcaat gccgattaag   2820
acccttaaag atagaatcgt atttaaatgt gctcatattg atattcttca ccctgaaacc   2880
ggagaagtta ttgttggtgc aaatgaggta attactaagg aagctgcaga caagatagtg   2940
gctgctggga ttactaaggt acaggttaga tccgttcttc actgtagatt gaaacagggt   3000
atttgtcaaa aatgctttgg ttacgacttg accacaaaac aaatgattga tgtgggaact   3060
actatcggtg ttatcgcggc                                                3080
```

<210> SEQ ID NO 99
<211> LENGTH: 826
<212> TYPE: DNA
<213> ORGANISM: Mycoplasma haemofelis

<400> SEQUENCE: 99

```
tcaatccatc ggtgagccag ctgttcagtt gaccatgaga acgttccact ccggtggggt     60
tgctggtgag tctaatattt cccaaggttt tgagagattg agacaactat ttgaaatagt    120
ggctcctaaa aaatgggaga cttctgtgat ctctgaaatt actggtacag ttgaaaatat    180
agaaattagg gatgatgaga gggttgttac tgtttcaagt gatatcaaca gaagggagta    240
```

-continued

```
caactgtgat ttgaacctgc cgatattagt taagaaaggg cagaagatta atttcggtga    300

cagaatatgt gatggatctg tagatcttaa aaagctgtta gaggtttctg gtgttgaggc    360

tgtaaggcaa tatatagttc aagagatttg gaaggtttat tggattcaag gtatcgatgt    420

ttccgagaag tatattgaga tcatagtaag acaattgaca tctagactta aagtgctttc    480

tccgaatgac tctaaatgag ctatgggtga ggttgtagac tactcttcct ttgttgatga    540

atgtgctaaa ttgcttttgg atgggaaaac ccctcctatt gccacaagca tcatcttcgg    600

tcttgaggag gtgcctgaaa agacaaactc cttcttggct gccgcttctt tccaagatac    660

caagaagatc ttgacagatg cttgtgttag aggtcagatt gattacttga attccttgaa    720

agagaatatc atggttggta acttgattcc tgctggaaca ggacttaaat ctgctgatga    780

agttatttct gatgagagat ctaatagaaa tgtctttaat tattag                826
```

<210> SEQ ID NO 100
<211> LENGTH: 681
<212> TYPE: DNA
<213> ORGANISM: Mycoplasma haemofelis

<400> SEQUENCE: 100

```
atgacaacag cagtaaagac ttctctattg gcgggaggcg ctgctgccgc ttcaggaatt     60

ggagctattg cttatggaga tttactttct ttccaaacac aaaaagaggc catttcttcc    120

ttgctttcca aagatccagc caagagagca ataggaacta cggaagagga ggaatgaaag    180

aagacttggg cgagatatag ggactccaag gaggatatat gaaagctggg tgatttaagt    240

ggagatgctc ctacagaatt caagaatgca tgtaaatcta aattggattt agaagtatct    300

ggatcagatt ctaaagaata caaggacttc ttactttatt gctctaggga tactttaatt    360

agtgatctca ttaaggagaa tagcaaaggc agagttctat tagagggaac tgacgtctct    420

tctacggatt ggcaaaatgc ctgaaaggca tattccgaag attcaagaaa ccagaaaggg    480

gagagtgaaa ctaatatttg aaatttaagt gattggaaaa ctcagaattc ccaacagaat    540

gcccctcaga gctttattac taagtgctct tccaatatta aacatccatc ccacgacatt    600

catgaccctc tctatataga tactgtcaaa ttctgcacca aggataagac aacagctccc    660

gcatcaacga ataatggcta a                                              681
```

<210> SEQ ID NO 101
<211> LENGTH: 651
<212> TYPE: DNA
<213> ORGANISM: Mycoplasma haemofelis

<400> SEQUENCE: 101

```
atggcagtta gttctctata caaaggagcc gctcttcttg gtggggcagg gagtgttgcg     60

ggaggatacg ccttagcaac acatttatct tctgacaaga aacaagagaa taaagtgacc    120

tctacagaag acagactcag aagtgaaggc tacacacctt tagacttcac caatactaat    180

ggggatggat gaagcaaaat taaggaggca tacaagttag agaattccga agataagaga    240

ttttctggcg ttgaaaagga gggaaataat acattatctg ggatcagaga ttcctgctta    300

cgatatctaa aggaagactc caccaacgag tctaattaca agatgtctag aaggtgatgt    360

gtggttccta tatcggtgaa ggataaatta ggagctagta atttactcaa atccggaacc    420

aacgagtccg atgatcattc caaatgggat gaagtagtta agaagaacga taaggacgcc    480

aataagttcg taactttttc ggaaagcgga aagagcagcg atgataagag agctgaaata    540

aagaagcaat gtgaagccaa agccgccata gagaccacta aggaagaatt tgaagaatct    600
```

-continued ttaaaccaag taaatttatg gtgcactcaa gcggccggaa cagcaggtta a 651

<210> SEQ ID NO 102
<211> LENGTH: 630
<212> TYPE: DNA
<213> ORGANISM: Mycoplasma haemofelis

<400> SEQUENCE: 102
atgaaaggag gggtggctgc tgccactgta ggaacaacag ctacaggagc ttatgtaggt 60
tctcgttact taactaatac aacttcagta tccaaacacc tgaccagctc tggatacaaa 120
ttgatctctt ccataaagaa tcctgatcat cttaagcttc agtggaaaga agaatttaag 180
tcggataagg catcaatcaa atcccttctc aacttgaagg aagatgatga aagtaaaggt 240
ggtgaagcat taggaaagtg atgcacttct aaattagcag aagaatactc agataaggtt 300
gacggcttag aaagcgtcaa aaagtattgc gttatcaaga ccataaagga ctgattaatt 360
agaaacggaa ataaggctat tcttactgaa aatcaggacg ataactctaa atgggaagct 420
acctataaca aacgcaaaca agccaaaact ccacgaaccc aaacaggatt aactgaaacg 480
tgacccgcag attccggcac agataagaaa gataccgatt taccaataat taagcgctga 540
tgtaaggaga agaatgattc agatttctta gcttacgaag acacatacag tcatgtaaaa 600
gactgatgta ccgaaagtgc taacgcttag 630

<210> SEQ ID NO 103
<211> LENGTH: 588
<212> TYPE: DNA
<213> ORGANISM: Mycoplasma haemofelis

<400> SEQUENCE: 103
atgcctactc ttaagacttt agttacgttc cctattgttg gtgtgtctgg ggcttttata 60
gtttctaatc tggacttaat atttcacgat gagcctgtca atatcaggag taagttaatt 120
agggatggct ttagattgct gtcaagtgat tctagttatt gggaattgct attgagtaag 180
catgaagaag agtcgagtct aaaggagaag ttgcccattc tagttaataa tctagaaagc 240
ttcaaggtag cttgcgaaga ggtgattcaa tttactgatt tgaataccta ttattctcaa 300
gctagtaggt gatgtgtagt tccacaaggc tttgaagata gattgaaatt tataggaaat 360
aaggagatct tggaatctga tgggatttgg ggagacttag tctctaagta tgagaaggat 420
agtaataatt cctttgtctc ttccctaggg agtcaaagta ctcaggaatt gaagataaag 480
gaacttcaga agttttgtaa ggatactaaa gagaaggagc tgaaaactta tgacaaagac 540
ttctccaagg atttcccttt gttcttaatg tgatgtacta agcgttag 588

<210> SEQ ID NO 104
<211> LENGTH: 624
<212> TYPE: DNA
<213> ORGANISM: Mycoplasma haemofelis

<400> SEQUENCE: 104
atgagcatca ttccaaaaat agccatggga actcttggct taggtggagt cgccggagga 60
ggtattcttc ttgctcgtaa tctaggcaat aagaatacct tagccagcaa attagaatca 120
gagggattca ctctgatggg agaaggtcat gatcaatgga gtaaaactct cgcagaatac 180
aataaggtca agggaacggc ggaagaggca tttaagattg cctctataga tttaacagta 240
gatcaactca aagaacaatg cctatctatt ctcaaatctg aaagctactc agagacggat 300

```
aagaataagg cctcaaggtg atgtactatt ccaatcacca ttcaatccag aatagaaaag    360

caagggagga gggtacttaa tgatgtcgat gacaatcaag atgataaaga tacttgagtc    420

tccctagtga ggaagcatct tacatctccg gaaagtagca gaatgtctgt cagcataact    480

gatcttcaaa atgatacagt tgatgatgaa agaataaagg ccatgaaagg cgggtgccgt    540

tccttgaaat ctaaaacgtc cctagaaaag acctacttaa atgactattc caaattccaa    600

gattgatgtt ctgcccctaa ataa                                           624
```

<210> SEQ ID NO 105
<211> LENGTH: 645
<212> TYPE: DNA
<213> ORGANISM: Mycoplasma haemofelis

<400> SEQUENCE: 105

```
atggcactaa gcacattaac caagggctcc attctcttgg gtggagttgg tagttcagtt     60

ggtggttatt tcttagtcaa caacttaact tcaggggaca agaaggaagc taaggccata    120

acttcaataa gagataagct cacccaagaa ggatacactc ctttgaattt tgaaaatacc    180

gcaggcagcg attgggagaa aataaagact gagtataaaa aggaaaatac ggacaccaag    240

agattctctg gagtcaataa ggatgatgat gctactgtat tagagggaat aaagaattct    300

tgtttgcaat atctactggg agactcgtct aacgaagata actaccaact atctaggaga    360

tggtgcgttg ttcccgtatc agttcagaat aagctaaaag gtagaacttt tctaaatacc    420

gaagctggtc aacccaataa cgacggagaa tgagacaaga tagtaaccaa gcatgattct    480

catcccaata agtggataat ttttgaagcc agcaaaagca aagaggaaaa gagaaccaag    540

atcaaggaga aatgctccgc tcaagctaaa ttagaaacga ctcatacaga tttcgaagac    600

gccttaagga atgtagatct ttgatgtact aaagaatctg tttaa                    645
```

<210> SEQ ID NO 106
<211> LENGTH: 639
<212> TYPE: DNA
<213> ORGANISM: Mycoplasma haemofelis

<400> SEQUENCE: 106

```
atgagtaagt taattccggc ctctttgggc gccatgggag ttagtggggc tggagtggga     60

agttacatat atctaacctc atcagaaaat aagaaagagg agaaggtcat gactttcaaa    120

gagaagtatt ctcatgcccc tctggattta gagggaaata caaatgacac aatatgatcc    180

tctaaattaa ctgctttaaa aacaggatcc ccccatcatc cagatttaat ttccgccaag    240

aatgccatca ctcctcaagg agaagataag gcaaagcctt tacataaaga agcttgtagg    300

aagatatatg gctcctcttc agataatcaa gactacttcc atgactttaa gaagtattgt    360

tctaagctat taggggatct agttacagga acttgaatat cctcagattc caactccaat    420

agctcatgag atggaaagct aaatgatttg attagtaaga aaagtgaatt ggtttcacaa    480

acactaaaga gcttcgctga aagcttaaaa acaggcagtt taaccgaaga acaaaggaaa    540

actattaagg attgatgttc tacccagaag gatcagttat tttctggaga aggagataac    600

gtaatacaag agatcaagag ttattgcact tcgaattaa                           639
```

<210> SEQ ID NO 107
<211> LENGTH: 171
<212> TYPE: DNA
<213> ORGANISM: Mycoplasma haemofelis

<400> SEQUENCE: 107

```
ttgacatccc cctccaaatt caataatgct gaaggatatt tagatcttat ggaagtaata     60

cctcccgctc cagctgttcc tagtgctgca aaggcgccct ttcccatgtt aattcgaagt    120

gcaataactc ttgatctctt gtattacgtt atctccttct ccagaaaata a             171


<210> SEQ ID NO 108
<211> LENGTH: 660
<212> TYPE: DNA
<213> ORGANISM: Mycoplasma haemofelis

<400> SEQUENCE: 108

atgggaaagg gcgcctttgc agcactagga acagctggag cgggaggttt aggagctggg     60

ggattgattg ctctcaagcc atggcaatct actcccgacg aagctcctat tacttccata    120

agatctaaat atccttcagc attattgaat ttggaggggg atgtcaatat atgggaaaag    180

aaatataaag ctctggagac gaaaacccca catcacccaa cactgcaaaa ggcacttagt    240

actggcaaag gtacaggagc taatttaacg gaggctaaga gtcttcttaa atctggatgc    300

agggcgattt atgagtctga ctcagataac tccaataact tccaagactt taaatccttc    360

tgctccaaaa caaatgaaga tgctactaag tctgggaaac aatgaattgc agatgccact    420

tccaaggcag atggaaacaa gtgagacact gtcttaacta gcttgaaagg ccataatact    480

tggtctctag atagtgtctt agagactttg aaaaagggag tccaaggaga ttccagctcc    540

tttccggaag cacgcagaaa agaacttaag gattgatgtg ataaggcaaa gctggaagta    600

tttgtaggag aatcatcatc agaattccaa agtcaagaag ccttttgtaa agcggattag    660


<210> SEQ ID NO 109
<211> LENGTH: 912
<212> TYPE: DNA
<213> ORGANISM: Mycoplasma haemofelis

<400> SEQUENCE: 109

atgattactg gtgcagctca aattgatgct gccatcctag ttgtttccgc aacagatggt     60

accatgcctc aaactagaga acacattctt cttgcaagac aagtgggtgt tgaaagaatg    120

gttgttttcc taaacaagtg tgacatggtt gaggatgttg aaatgcaaga cttggttgag    180

atggaagtta gggatcttct tacatcctat ggttatgacg gttctgcaac tcctgttgtt    240

agaggttccg ctcttaaggc tttagagggt gacgagaagt atgttcaatc cataaaggat    300

cttcttggca acttggatga atacgttcct ttacctgtaa gggaggttga taaacctttc    360

cttctttcaa ttgaggacgt attgactatt acaggtcgtg gtactgttgt tactggtcgt    420

tgtgaaagag gtactcttaa ggttaacgaa gaggttgaaa ttgttgggct taaagaaaca    480

agtaaagctg ttgttaccgg tattgagatg tttagaaaac ctcttgacga agttctggca    540

ggcgacaatg ctggggttct tctgaggggt gttaacaagg atgaagtttc tcgtggtcaa    600

gtgttagcta aacctaaatc cattactcct cataagaagt ttcacgctca aatttatgct    660

cttaagaagg aagagggtgg aaggcatact gccttcacta aggggtataa gcctcagttc    720

tactttagaa caactgacgt taccggaact attgatcttc ctgaaggttc agagatggtt    780

atgcctgggg ataatgctaa gatccttgtt gagttgataa acgtggttgc tattgaaaaa    840

ggttctaagt tctcaattag agaaggaggt aaaaccattg gtgctggtac ggttgtagat    900

atcgtcgagt ag                                                        912


<210> SEQ ID NO 110
```

<211> LENGTH: 1251
<212> TYPE: DNA
<213> ORGANISM: Mycoplasma haemofelis

<400> SEQUENCE: 110
gtgtcctgtg gggaagggca gattgtttct gttcttggtg ttttctttgg agacgaagga 60
aaggctaaga tagttgacta catctctaag gactttgatt acgtagtacg ttatcaaggt 120
ggggataatg ctgggcacac tgtatgcata ggggatagga agtacatatt tcagttaatt 180
ccctgcggaa tattacaaac taaggcattt atagctcacg gagtagtttt aaatcccgaa 240
agccttctta aggaaataca ggatcttagt gaatgtgttg aaatcaaaga taggctcttc 300
atctctgatc acgcccatgt tatttgcgat tgaaatatag cctatgataa attccttgag 360
aacttacgag gctctcaagc aataggaact accaatagag gtattggtcc cacttattcc 420
aataaggctc taagattagg aattagagtt aaagatcttc tggattacga ttcccttcgt 480
gagaagatag atctgaattt aaagatatac aacgtccttt tcaagagtta tggacatccc 540
acatttgatt tagaagttga gaccaagaaa tactttgaat atggacagaa gataaaaccc 600
tacttagtgg attcttacca ttgaatatat ggggagctat ctaaaggcaa gagatttcta 660
tttgaaggaa gtcaaggtct gatgctagat ctggacttgg gaacttatcc ttttgttact 720
tcttcaaata ttactggatc tttaatttct gggacttccc tatcttttag gcattttaaa 780
aggatagttg gggttgtgaa gacctatagt agtagggtcg gaaatggtga gtttattact 840
gagatccatg atcaagatct ttctggatat atcaggaaag tagggaatga gttcggatct 900
gtaactggga gaccgagaaa gataggatga ctagatttag tggcactgaa gtacgtagtt 960
actatttcag ggattacaga gatagttctg actttagtgg atgttttgaa taatttgggg 1020
gaagtgaagg tatgtaactc atatgagtac tcttcaaagg agcctattcc tgtgtacaag 1080
tcttttaagg gatggaagga ggattactct tccataaaga ggtattccga cttctccgat 1140
gagttcaaga acttcgtaaa gtatatagag gactttgttg gagttccggt aactataatc 1200
tcctacggaa gaagtagaga ggatacctta gttcgtatga atgaaaatta a 1251

<210> SEQ ID NO 111
<211> LENGTH: 789
<212> TYPE: DNA
<213> ORGANISM: Mycoplasma haemofelis

<400> SEQUENCE: 111
atgaaaatta aactagagct accatcccac gtcaaacact ccatctctaa tttaaatagg 60
ttcaagaagg aggtagactt agtcataaat gtcgttgatg ctagggctag taagaccagc 120
aatttaaatc tttatatatc taggatattt tctaaatcta agatactaga tatatttagt 180
aagtccgatt tagcaagctc cgaaggacta gagaattcct ttaatttcaa aattcagagc 240
aatagaaatc gaattcttca tttaataaag aaggctttac aagaggagag aaatagactt 300
caggaatcgg gatatttaaa tcctcacttt aagatactag tagttggaat gcccaatact 360
gggaagtcta cacttattaa tctacttaag aataagaaaa tctctaaggc cgctaatact 420
cccggaatta ctagaaagat tacccagtat tatcttggag ataacttatg actctttgat 480
tctcctggaa ttttcttcta tcaggatata tctcccgagt tgctttgaaa gctcattgtt 540
ataaatgccg ttccttccaa tttcaaggag tactcggaga tattagaaat tactttttga 600
tatttaaagg ataagtatcc aaattcgatg gatgagcttt ctgccgatag ctatttatcc 660
tttatagagt tacttgcaaa gcgatataac ttcaagaata gagggggtac ttttgatcta 720
gaaagagccg aggagaaatt tttgtttctc cttaggaacg gcggaataag ggacgtatct 780
tgggactaa 789

<210> SEQ ID NO 112
<211> LENGTH: 894
<212> TYPE: DNA
<213> ORGANISM: Mycoplasma haemofelis

<400> SEQUENCE: 112
ttgtctaact cttcacaaaa ttgactttcc ctcaacttaa agacaagttt attagtgggg 60
gcagcttcta tatctgctgc aggaaccact tctagtgttc tctctaatgc tagcggaggc 120
gttttagagg cggttaagaa ttcctcccaa ccaattattg atccttttca gaaggggtat 180
tctaagttat cagagcagct ggatagtttc tctaagcagg gatataacgc aggagtagat 240
gctaagtctt gagtaacaga gaatttaagt aagtctaaga taaagactgg cgaaactaat 300
atctaccaga acttaagtga ttgatacaga gcagttaaag ggtttgctga tagtgcgcgc 360
actacaatct cagagttctt tcagaaatgg agtgagcata gggagactat gcatgtggtc 420
tttaaggcat taggtaactc cttctcccta ttgggaggat taatgggttc ttttgaatct 480
gatggggagt ccggacttaa gatattgttc gaagtaattg ggaagcctaa attcaaggat 540
ttcatgactc aagtttcttc attggtgtcc aagaacccca atctgatgtc ttctcttgag 600
ggtaatgatg taatggatgt tctttctgcc tttaggcaag atgaggatac agttgttgat 660
actttgaagg gattaagcga gaaggatgcg ggaacagttg acaaggctac tcttatgaat 720
gccttgaagc tttattctct aatggataaa gcccgaaatc ttatgagtaa ggctagaacc 780
attcttgagt cgaaggataa agagaaagct aaacaactaa ttcaagaaat aaccgaggct 840
cacaaacaaa tggaagcctt aataaaggct aatgaagggc aagctaccga gtaa 894

<210> SEQ ID NO 113
<211> LENGTH: 657
<212> TYPE: DNA
<213> ORGANISM: Mycoplasma haemofelis

<400> SEQUENCE: 113
ttggggagta tgtcattatc tttagcctct aaagcaacag cgggcatagc tggaactgga 60
gcggttgctg ggggaggggc ttttgcagct tataaatttc ttaatcagga aacaatagag 120
aagtacttga actccctaca cagggagtta gctgtttcca atgaagattg agaattaata 180
aagaataatt atgccgcgga caaagcagag aatccaatcc ctaacattcc caaatctacc 240
attaaagata aattaaacga tcttaagaag tggtgtagtg atcgtttaaa cgaagaattc 300
tcccaagaga aggcaagtaa aggggattac aacctaatcc aagcttgatg tactaagcaa 360
gtaaaaatat ccgattattt aaaacactta aagttggctt ctctagatac ctccggaact 420
aaagacgata ctacttgaaa taagttgaaa gatgagtatt caactagtgg gggcttaaaa 480
gtaaatgaaa taaccggaca agaaggtagc aaaacggaag ggggtgaggt aagcacctta 540
tccgacaata caaaactcaa aacttggtgt tcttggtctg tgagccaata cttcaagcac 600
caagaagatt ccctatttaa aagatataaa cacttctgta ctaagcaggc aaactag 657

<210> SEQ ID NO 114
<211> LENGTH: 651
<212> TYPE: DNA
<213> ORGANISM: Mycoplasma haemofelis

<400> SEQUENCE: 114
atgttatcta aggcgggagt ggctgctgtt ggagcgttag gggctggcac ggcctcctat 60
atgggttatg aatatgtatt taatgctaaa gaagaggtaa agaaggtaac tataggggaa 120
gctttagagc ctttcctact taatactgag tcttcagata agtgagcttc cagaaaggat 180
aagctttcta aagctaatga ggattctttg gtggaagaat tgaaatcttt gaagagtgga 240
gtaactgagg atcaagttaa gaattggtgc tctgtagcct ctactaaggt ttattctgaa 300
gttagtggtt tgtatttaga gaatgtaagg agttattgta ctttccatat tgaagataaa 360
ttaccatcag gatatataaa ggatactgaa gattgggaga aggccaattc gagacttaaa 420
gaagttaatc ctgatacagg actatctagt catatgaaag aggtaaaaga taagttgtct 480
aagcaggatt ctcccgatac taatgcctta aaggattgat gtatgggggc gtatgggaag 540
ccttatttgg gagacgataa tcaggacttt gtagatgcta gaacttactg ttctaaagta 600
gcggaagcat ctccttccgg atccactcag gcagctagtt tgcctgctta g 651

<210> SEQ ID NO 115
<211> LENGTH: 609
<212> TYPE: DNA
<213> ORGANISM: Mycoplasma haemofelis

<400> SEQUENCE: 115
atgagtaaat tagctgcatt aatattaggg atagcgggaa ctgctgggac tgcaggactc 60
ggtttcctaa ttgccaagaa tcaaaaggat gaaactaaga aaataaaaaa taactatccc 120
catgcaatct tgaccttttc aaataacgaa ggatgaaatt ctaaatttca acttctaaac 180
tcaaaagaga caactcaccc tactctcaaa aaagcaaagg ctcaattttc aaacacttcg 240
caatctcaag agctttataa aaagggggtgt aatgagattt atgactctga aggaacccaa 300
tatctcgatg atttcaaaac attctgttcc aaaaccaaca aggatgcaat tacaggttca 360
tgaataagcg atgcagctag tgtaaatact aattgagata agaagttaac tagcctaaag 420
gaacgaaata gtggattgag ttcggaattc ttagaggttc aaagttcttt gggttccggc 480
agcttcgatg aaacagccag aggaaagata aagaaggctt gcgatgattc ccattcggag 540
atttatttag gtccaaacga tataaaaacc cagagtatta aagacttttg cttgtcagaa 600
cagacttaa 609

<210> SEQ ID NO 116
<211> LENGTH: 870
<212> TYPE: DNA
<213> ORGANISM: Mycoplasma haemofelis

<400> SEQUENCE: 116
atggcactgg ttagcgcaag agagattctt cttaaggctt ataaggaagg ttatgctgtg 60
gctcaaatta acaccaataa ccttgagtga actaaagcta tattgcttac cgttcaagaa 120
ttaaagtctc cagttattat tggtgcttct gagggagcta tcaaatatat gggtggcttc 180
agaactgttg cctccctagt taaagccatg attgaagatt tgggaatcac agtgcctatt 240
attcttcact tagatcatgg aagttatgag ggatgtaaga aggccatgga tgctggattt 300
agttccgtca tgtttgatgg ttctcacttt cctatagatg agaacttcca gaagtctaag 360
gagattgtcg atctagctaa ttctaggggt atttctgtgg aattggaagt tggtactatt 420
ggcggcgaag aggatggagt tattggcgct ggagaaaatg caagtgttga tgaatgtgtg 480
aagattggtg gtcttgattt gtccatgctt gcggcaggaa ttggtaatat ccacggtcct 540

```
tatcccgata actggaaggg tttaaacttc cctcttctta aagagatatc tgatgcagtt    600

aagaaaccta tggttcttca tggaggaact ggaattcccg aagatcaaat taagaaggct    660

atatctttag gtatctccaa gatcaatgtt aataccgagt tacaattggc ttttgcagct    720

gcaactagga agtatataga ggaaaagaat gatttgaata tgtctaagaa gggatttgat    780

cctagaaagc ttcttaagta tggttacgat ggaatctgcc aagtaattaa ggataagtta    840

actatgtttg gttctgttgg aaaagcttag                                    870


<210> SEQ ID NO 117
<211> LENGTH: 573
<212> TYPE: DNA
<213> ORGANISM: Mycoplasma haemofelis

<400> SEQUENCE: 117

atgtcaaagg ataataaaga gcaaaaagag gaagaaatcg ttgaggaggt atcggagtta     60

gatcaactta aagcgaaact taaggaatgg gaggataagt tttctgagtt agagaaggag    120

agtaatcaga ggcttttaga gtttgtagaa aagaagagca aggaggcttc cgatattatt    180

gcgaagaaag aggaggagat aagtcagaga tataagaagg aactggagga agctaaggat    240

tatttgtatg agaagccttt agcttctttg gttggggtaa tttctcaatt tgaagcagtc    300

ataaagatga ctgtggatcc taacatttct caatacttgg tgggttttag gatgttcttg    360

actcaattta atgatctact aagggagttc tccatttcca tcattgaacc aaaggatgga    420

gatgaatttg attcctcctt tatggaagct actgtggtag agaaggtttc tgatgattct    480

ttgaataata aagtgattag tgttttttct aaaggctata ggttaaaaga tagaataatt    540

agattagcgt ctgttaaagt agggaagatt tag                                 573


<210> SEQ ID NO 118
<211> LENGTH: 1047
<212> TYPE: DNA
<213> ORGANISM: Mycoplasma haemofelis

<400> SEQUENCE: 118

atcaagaagg cttataggaa gttagctaag aaatatcatc cggatatcaa taaggaagcc     60

ggagcagaag ctaaatttaa ggatattaat gaagcttacg aaacgttagg agatcctcag    120

aagagaagta attacgataa tttcgggact tctggggatg gaatgggtgg cgccggagga    180

gccaatcctt ttgatatttg aaatagtttc ttctctgggc aagcttcggg gggattctct    240

gagtttgata tattcggagg atcagattcc catcaatcac aaccccagta tgagaattat    300

caggatcgaa tagttatctc ctttctggcc tctataaaag gagttaacca ttcctttacc    360

tatgaatctg aaaagagatg tgaggtttgt aagggtaata aggctttaga tggggattct    420

aagtacataa ttacatgtga taactgtcgc gggacaggat gggagatgct gcgaaagcag    480

accatctttg gagttgtaaa taccaaggca tcttgtagaa ggtgtaatgg acaaggtaag    540

atgatatcta agccttgtaa ggagtgtggg ggaagagggt acaagaagtt tcataagact    600

cagaacttct ccattcctgc cggcgttcaa gataaggatg tcttggtggc atgggataag    660

actggaatag tagataagaa gatctcaatt cacgtttcag taagaccatc cgagatcttc    720

tctaggaagg gaaatgatct ttatacgaga atcgttatta accctttcgt ggccattttt    780

ggaggaacag cttccattcc aacaatcagc ggcattaaat ctataaagat agcggccgga    840

actaattctg ggagaagct aaaacttaag ggattgggag ttaaatcttc tgcagggaga    900
```

```
ggggatttaa taggagaagt ttgctttgcc ccagtcccta agctaactaa agagcaaaaa    960

gaggtgctaa aatcacttag tgatttagaa gttcctgagg ttactaggtg ggtatctaaa   1020

gctaaaaagg cagttgtttc cgattaa                                      1047
```

<210> SEQ ID NO 119
<211> LENGTH: 2022
<212> TYPE: DNA
<213> ORGANISM: Mycoplasma haemofelis

<400> SEQUENCE: 119

```
atggcccaca ttgatgctgg gaagaccact accagcgaga gaatactatt tcacacaggt     60

aagacttaca agatagggga agttcatgat ggtgctgcca ccatggactg gatggaacaa    120

gagaaggaga aaggtattac tattactgct gccgctacat ctgtatcttg aaagaatcat    180

caacttaatc ttattgatac tccaggacac gttgacttca ctgtggaggt ggagaggtct    240

ctaagagttc tagatggagc tgttgctgta ttggattctc agatgggtgt tgaacctcag    300

actgagacag tttggcgtca agcaactaag tactccgttc cccgaattgt ctactgtaat    360

aagatggaca agattggtgc cgacttcttt aagtcagttc aatctttgag ggataagtta    420

aaggttaagg ctgtattagt tcagctgaat attggtaagg agagcgagtt tactggaatt    480

atcgatctta tagctaagaa ggcctattct ttcgatggaa agcaagagga ggaatataaa    540

gagataccta ttccagacaa tctaaagggt gaagttgaca gattacatca agagttatta    600

gatgaagtcc tagtcttcga tgagaagatt atggagaagt atttgggtgg tgaagaggtt    660

actatcgatg agataaagcg atgtattagg ataggaacta tacaaactaa gctattccca    720

gtattttgtg gttcttcctt taagaataag ggagttaaat tcctgcttga tgcaattatt    780

gactaccttc cgagccccgt agatttacct gaaactcccg ctttcgataa agaacagaat    840

cctatttcca ttaagaattc cgcagagggg gagtttgtgg gaatggcctt caagattgcc    900

accgatccat ttgttggtag attgactttt attagggttt attctggaat tctaaagaag    960

ggtagcgcca tatataacac cacccaggat cttccggaga aggctggtag attggttcaa   1020

atgcactcca atcacagaac cgaaatagag agcatacaag cgggtgagat ctgcgccatt   1080

gttggtttga agaatactag aactggggat actcttactg tgaaggggaa tgctgttgtg   1140

ttggaatcta tgaactttgc agaaccagtt atctctctag ccatcgagcc taagactaag   1200

gttgaccaag agaagatgtc tatggttctt tctcgtttgt cggaggagga tcctacattc   1260

aagatatcaa ctaacgttga aactggtcaa accattattt ctggaatggg agagttgcac   1320

ttggaaatcc ttatagaccg tatgaatagg gagtttggat tgcaagttaa tatcggacaa   1380

cctcaagtcg cttttaggga gactttcact caggtttccg atgttgaggg taagtatatt   1440

aagcagagtg gtggtagggg taactatggt cacgtttgga ttaagtttga acctaataag   1500

gataagggtt ttgaatttgt ggacaagatc gttggaggta agattcctaa ggagtacatt   1560

aagtccatta gacagggatt aatagatgct atgaagtctg gtcccttggc cggttatcca   1620

atcatagata ttaaggccac actatttgat ggatccttcc atgaggtgga ctccaacgag   1680

atggccttta gaattgccgc ctccttagct cttaaggatg caagtaagaa gtgtgcttcc   1740

attcttctag agccaattat gaatgttgag ataaccgttc ctcttcaata cttcggaact   1800

gtaatgggag atgtaacttc tagaagggga ttaattgaag gtacggagca agttgagaat   1860

gctcaaatta ttaaatccaa aatccctcta aaagagatgt ttggatacgc aactgttctg   1920

agatccttta cgcagggtag aggtatttac actatgcagt tctctcatta tcaaccactt   1980
```

cctaagtcta taactcaaga gatgttggaa ggtcgaaagt ag 2022

<210> SEQ ID NO 120
<211> LENGTH: 1674
<212> TYPE: DNA
<213> ORGANISM: Mycoplasma haemofelis

<400> SEQUENCE: 120
ttgcaaaaaa taaaagacta cctctctagt gagttcaacc tagcggcaca ggctctgggc 60
tacaggttaa cgggaatcga ggcgtcattc gattttacaa aagattacaa attcggcgat 120
atattcacca acttcgcctg ccgaataagt tctaagtata agaaaaaccc caaagacgtt 180
ggtgaggagc ttcttaagca agttggagag cttaagtatg tttcttcagc taaggtagag 240
aagaatgggt tcataaatat attcttctct cccgaaatat tctccgaata ctactcagag 300
attctggaga agagagagga tatatggaga aagcatccca ttaattcttg atacttcgtt 360
gagatagtct cagccaatcc aactggttta ttgcacatag ggcatgcaag gaatgggata 420
ttctcggata cccttgctaa cctcctagag tatggaggtt acttcgttca cagagagtac 480
ctagtaaata acttagggaa tcaaataaag gagcttcttg agtcaatatg gatcaagtac 540
aaagctaagt taactagtat ccctagggaa tccaatacta aggtagtaaa gtacaacggg 600
aaggagatag atgagtgtgt agattacttg atctccactc atggtcagag atggatattc 660
gatagaaata tctttgaatc taagagctat ccagaacttg agaagcttgt agttagctac 720
ttccttaatg aaattgagaa ggatttagct aggtacaaca tagaggtgaa tgcttggaaa 780
tttgagagta gctttgtgaa ttctgaatcc ataaatgatc tctttaagtc catgaaggaa 840
tacttgaggg tgaaggatgg ggctatttga tttaaagctg gggagatatt ggatgaatgt 900
aaggatgagg tattgataaa gaatgatggg aagcatactt actactgcca agacttaatt 960
tatcacctat ataagctgag cttattgggt aatgagggaa agattattaa tgtactggga 1020
tctgatcact acgggcatat agataagctt aaggctttcc tgaagctgaa ggaagtggat 1080
gatgatagag tgcatttcat atgcatgcag ttggtgaagt taatggagca tagtacatta 1140
gtgaagatat ctaagaggga ttccaaggtt atttatctga gggatttgat gaattacatg 1200
acctacgaag aagctagatg attcctagta tctcagcatc ccgactctcc cctagagata 1260
gatatacagc gattaaagca gaagaactat aacaaccctg ctttctatgt gatgtatgca 1320
tactctagga tattccagat actgagaaag catggagagc cttatttcta ttccaagaaa 1380
gaggtactat tcaagactat tactgatgga atagagaaga ctattatgaa tacccttatg 1440
caatgggatg aagtcataca tgaagctata gagactcttc agccctacag gattactcag 1500
tatctcttca agttagctaa ggagtttcat tccttctatg aggagacgaa gctattacaa 1560
gaagggcatg aagaagagtg attgagagat aggttagctc tgcttaatgc cgctaaatat 1620
acgatacact ctggattaag cattcttaag attaagccaa aaagtgtcat ttaa 1674

<210> SEQ ID NO 121
<211> LENGTH: 583
<212> TYPE: DNA
<213> ORGANISM: Mycoplasma haemofelis

<400> SEQUENCE: 121
atgacttacg caaagcttgg agccgccacc ttgggaactg ctggggcggc aggaggtggg 60
tatctggctt atccacacgt atttcccgaa cgaaccctat tggatgaact taaatctcag 120

```
aataaatcag taataaatgg aaatgagagt caatgaactc tgaaaaagga gctttataac    180

aagggtacca atagctccaa gataactatt gacaacaagg agaaggctag cattacggaa    240

gcggaattaa agaagtgatg ttccgataat ctcaaagcac cttattccaa ggctaaggac    300

tctatccttg gtaaggtcga gaaatgatgt cttaagccta atataaagga agctttatcc    360

aaggagacaa aggaaataat ttccttcacc ggaaccacca ttgatgccgc ttgagaatct    420

aaactaacca caaattcaag tagtgtgaaa ggtgagttaa tagataaatg aaagttaccc    480

gtttcttccg aagggaacga caaagtgagt aaggagtctc tgagggacgc ctgtcaactg    540

aaagtagagg gagagtatat ttccgagaat gatgagaatt aca                      583


<210> SEQ ID NO 122
<211> LENGTH: 65
<212> TYPE: PRT
<213> ORGANISM: Mycoplasma haemofelis

<400> SEQUENCE: 122

Val Lys Ala Ala Ser Gly Leu Gly Val Ala Ala Ala Thr Val Gly Gly
1               5                   10                  15

Gly Ile Phe Val Ala Lys Gly Met Glu Gly Ser Pro Ser Thr Pro Lys
            20                  25                  30

Ser Thr Val Gln Asp Lys Leu Lys Gln Asn Gly Tyr Ser Pro Leu Asp
        35                  40                  45

Leu Glu Lys Ser Asp Gly Trp Ser Glu Val Leu Glu Ala Tyr Asn Gln
    50                  55                  60

His
65


<210> SEQ ID NO 123
<211> LENGTH: 171
<212> TYPE: PRT
<213> ORGANISM: Mycoplasma haemofelis

<400> SEQUENCE: 123

Met Gln Lys Tyr Leu Thr Glu Val Asn Glu Glu Asp Ile Lys Glu Gly
1               5                   10                  15

His Tyr Ser Ser Lys Lys Lys Glu Leu Leu Asp Leu Ile His Tyr Lys
            20                  25                  30

Lys Glu Trp Ile Leu Thr Ser Asp Lys Glu Ile Ser Tyr Lys Ser Gly
        35                  40                  45

Tyr Phe Gln Glu Lys Leu Asn Asn Phe Gly Asp Asn Lys Leu Val Gln
    50                  55                  60

Asp Ile Leu Trp Ser Leu Val Glu Glu Ser Gln Val Asn Ala Thr Leu
65                  70                  75                  80

Ile Arg Pro Glu Ser Ile Thr Ile Asn Phe Lys Arg Glu Lys Val Gly
                85                  90                  95

Tyr Gln Lys Asn Pro Leu Leu Asp Lys Ser Asp Val Ile Lys Asn Leu
            100                 105                 110

His Ile Lys Phe Arg Ile Phe Asn Pro Asn Arg Gln Lys Thr Phe Val
        115                 120                 125

Phe Lys Ser Ile Glu Ile Asp Pro Thr Ser Glu Thr Asp Val Glu Ile
    130                 135                 140

Thr Leu Arg Glu Gly Glu Leu Lys Pro Val Ser Thr Ala Leu Ala Ala
145                 150                 155                 160

Leu Ala Ala His Lys Leu Ser Ala Ser Ser Trp
                165                 170
```

<210> SEQ ID NO 124
<211> LENGTH: 150
<212> TYPE: PRT
<213> ORGANISM: Mycoplasma haemofelis

<400> SEQUENCE: 124

```
Leu Gly Ile Asp Gly Leu Glu Ile Asp Ala Asn Glu Tyr Ile Glu Asn
1               5                   10                  15

Ile Tyr Glu Ala Ser Asn Ser Pro Ile Gly Ile Ala Ile Gly Asp Ser
            20                  25                  30

Glu Asp Tyr Gln Gly Ile Asn Ile Lys Gly Lys Asn Ile Gly Trp Lys
        35                  40                  45

Ala Leu Asp Val Ser Ser Ser Ile Asn Leu Ala Asn Phe Ser Lys Phe
    50                  55                  60

Phe Tyr Lys Leu Tyr Glu Lys Ile Asp Thr Tyr Lys Asp Pro Ser Asn
65                  70                  75                  80

Ser Ala Leu Gly Val Ser Gln Leu Trp Asn Phe Thr Thr Leu Leu Gln
                85                  90                  95

Gln Arg Pro Ile Ser Phe Ile Ile His Ala Ile His Ser Thr Phe Asp
            100                 105                 110

His Gln Tyr Leu Lys Ser Gly Asn Ser Thr Ser Glu Asp Lys Arg Pro
        115                 120                 125

Trp Pro Val Phe Phe Lys Ser Leu Phe Gln Asp Pro Ile Thr Leu Lys
    130                 135                 140

His Lys Gln Val Phe Val
145                 150
```

<210> SEQ ID NO 125
<211> LENGTH: 159
<212> TYPE: PRT
<213> ORGANISM: Mycoplasma haemofelis

<400> SEQUENCE: 125

```
Met Asp Gly Gln Glu Lys Gly Lys Lys Asp Ile Ala Asn Asp Pro Glu
1               5                   10                  15

Val Arg Lys Glu Leu Glu Ala Tyr Glu Lys Tyr Ile Leu Gln Gln Lys
            20                  25                  30

His Glu Ile Phe Asn Arg Ile Ile Leu Asn Ala Ile His Thr Leu Lys
        35                  40                  45

Ile Gln Gln Pro Ile Ile Ser Cys Cys Lys Arg Ile Asp Leu Ser Ser
    50                  55                  60

Leu Pro Gly Phe Asn Glu Glu Thr Ile Gly Gln Leu Leu Gly Lys Asp
65                  70                  75                  80

Gly Gln His Lys Gln His Phe Ile Asn Leu Thr Lys Val Asp Leu Gln
                85                  90                  95

Val Asp Gln Lys Cys Pro Asn His Gly Ile Val Leu Ser Lys Tyr Asn
            100                 105                 110

Ser Val Asn Val Glu Lys Ala Val Glu Leu Val Lys Lys Leu Leu Glu
        115                 120                 125

Leu Lys Ser Trp Asn Leu Glu Lys Met Lys Ser Leu Tyr Glu Lys Val
    130                 135                 140

Asn Lys Glu Phe Glu Asp Lys Cys Asn Lys Ile Gly Gly Gln Trp
145                 150                 155
```